(12) United States Patent
Radaelli et al.

(10) Patent No.: US 11,542,214 B2
(45) Date of Patent: ***Jan. 3, 2023

(54) OXIDATIVE COUPLING OF METHANE METHODS AND SYSTEMS

(71) Applicant: Lummus Technology LLC, The Woodlands, TX (US)

(72) Inventors: Guido Radaelli, South San Francisco, CA (US); Robert Bridges, Friendswood, TX (US); Humera A. Rafique, Dublin, CA (US); Suchia Duggal, San Rafael, CA (US); Srinivas Vuddagiri, Davis, CA (US); Joel Cizeron, Redwood City, CA (US); Jarod McCormick, San Carlos, CA (US); Bipinkumar Patel, Richmond, TX (US); Satish Lakhapatri, Mountain View, CA (US)

(73) Assignee: Lummus Technology LLC, Houston, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/060,506

(22) Filed: Oct. 1, 2020

(65) Prior Publication Data

US 2021/0024439 A1    Jan. 28, 2021

Related U.S. Application Data

(63) Continuation of application No. 15/690,090, filed on Aug. 29, 2017, now Pat. No. 10,793,490, which is a
(Continued)

(51) Int. Cl.
*C07C 2/84* (2006.01)
*C07C 29/48* (2006.01)
(Continued)

(52) U.S. Cl.
CPC .................. *C07C 2/84* (2013.01); *C01B 3/38* (2013.01); *C07C 4/02* (2013.01); *C07C 5/48* (2013.01);
(Continued)

(58) Field of Classification Search
CPC .... C07C 2/84; C07C 1/04; C07C 1/12; C07C 5/327; C07C 9/04; C07C 11/04; F01K 27/02; C10G 50/00
See application file for complete search history.

(56) References Cited

U.S. PATENT DOCUMENTS 2,324,172 A  7/1943  Parkhurst
2,486,980 A  11/1949  Robinson
(Continued)

FOREIGN PATENT DOCUMENTS

CA    2041874 C    4/1999
CA    2765769 A1   1/2011
(Continued)

OTHER PUBLICATIONS

Extended European search report and opinion dated Mar. 11, 2021 for EP Application No. 20199359.9.
(Continued)

*Primary Examiner* — Jafar F Parsa
(74) *Attorney, Agent, or Firm* — Calfee, Halter & Griswold LLP

(57) ABSTRACT

The present disclosure provides natural gas and petrochemical processing systems including oxidative coupling of methane reactor systems that integrate process inputs and outputs to cooperatively utilize different inputs and outputs of the various systems in the production of higher hydrocarbons from natural gas and other hydrocarbon feedstocks.

17 Claims, 30 Drawing Sheets

Related U.S. Application Data continuation of application No. PCT/US2016/022891, filed on Mar. 17, 2016, which is a continuation-in-part of application No. 14/789,953, filed on Jul. 1, 2015, now Pat. No. 9,334,204.

(60) Provisional application No. 62/195,237, filed on Jul. 21, 2015, provisional application No. 62/190,182, filed on Jul. 8, 2015, provisional application No. 62/141,177, filed on Mar. 31, 2015, provisional application No. 62/152,706, filed on Apr. 24, 2015, provisional application No. 62/134,508, filed on Mar. 17, 2015, provisional application No. 62/300,287, filed on Feb. 26, 2016.

(51) Int. Cl.
| | | |
|---|---|---|
| *C01B 3/38* | (2006.01) | |
| *C07C 4/02* | (2006.01) | |
| *C07C 29/151* | (2006.01) | |
| *C25B 15/08* | (2006.01) | |
| *C25B 1/04* | (2021.01) | |
| *C07C 5/48* | (2006.01) | |
| *C25B 1/26* | (2006.01) | |

(52) U.S. Cl.
CPC .......... *C07C 29/1518* (2013.01); *C07C 29/48* (2013.01); *C25B 1/04* (2013.01); *C25B 1/26* (2013.01); *C25B 15/08* (2013.01); *C01B 2203/0233* (2013.01); *C01B 2203/0283* (2013.01); *C01B 2203/043* (2013.01); *C01B 2203/0445* (2013.01); *C01B 2203/0465* (2013.01); *C01B 2203/0475* (2013.01); *C01B 2203/061* (2013.01); *C01B 2203/068* (2013.01); *C01B 2203/0811* (2013.01); *C01B 2203/0827* (2013.01); *C01B 2203/0833* (2013.01); *C01B 2203/0872* (2013.01); *C01B 2203/1241* (2013.01); *C01B 2203/84* (2013.01)

(56) References Cited

U.S. PATENT DOCUMENTS

| | | |
|---|---|---|
| 2,577,701 A | 12/1951 | Philip et al. |
| 2,579,601 A | 12/1951 | Nelson et al. |
| 2,621,216 A | 12/1952 | White |
| 2,643,216 A | 6/1953 | Findlay |
| 2,673,221 A | 3/1954 | Schrader et al. |
| 2,880,592 A | 4/1959 | Davison et al. |
| 2,906,795 A | 9/1959 | Ballard et al. |
| 2,926,751 A | 3/1960 | Kohl et al. |
| 2,943,125 A | 6/1960 | Ziegler et al. |
| 3,094,569 A | 6/1963 | Thomas |
| 3,128,317 A | 4/1964 | Arkell et al. |
| 3,325,556 A | 6/1967 | De Rosset |
| 3,413,817 A | 12/1968 | Kniel |
| 3,459,678 A | 8/1969 | Hagemeyer, Jr. et al. |
| 3,516,262 A | 6/1970 | Bernstein |
| 3,584,071 A | 6/1971 | McNulty et al. |
| 3,596,473 A | 8/1971 | Streich |
| 3,660,519 A | 5/1972 | Takaaki et al. |
| 3,686,334 A | 8/1972 | Britton |
| 3,686,350 A | 8/1972 | Ono et al. |
| 3,702,886 A | 11/1972 | Argauer et al. |
| 3,709,669 A | 1/1973 | Marion et al. |
| 3,751,878 A | 8/1973 | Collins |
| 3,754,052 A | 8/1973 | Hoffman et al. |
| 3,761,540 A | 9/1973 | Carter et al. |
| 3,862,257 A | 1/1975 | Buben et al. |
| 3,900,526 A | 8/1975 | Johnson et al. |
| 3,931,349 A | 1/1976 | Kuo |
| 3,966,644 A | 6/1976 | Gustafson |
| 3,994,983 A | 11/1976 | Webers et al. |
| 4,012,452 A | 3/1977 | Frampton |
| 4,090,949 A | 5/1978 | Owen et al. |
| 4,101,600 A | 7/1978 | Zhukov et al. |
| 4,107,224 A | 8/1978 | Dwyer |
| 4,115,086 A | 9/1978 | Jordan et al. |
| 4,126,645 A | 11/1978 | Collins |
| 4,132,745 A | 1/1979 | Amigues et al. |
| 4,140,504 A | 2/1979 | Campbell et al. |
| 4,211,885 A | 7/1980 | Banks |
| 4,232,177 A | 11/1980 | Smith, Jr. |
| 4,311,851 A | 1/1982 | Jung et al. |
| 4,314,090 A | 2/1982 | Shewbart et al. |
| 4,328,130 A | 5/1982 | Kyan |
| 4,329,530 A | 5/1982 | Irvine et al. |
| RE31,010 E | 8/1982 | Gelbein |
| 4,347,392 A | 8/1982 | Cosyns et al. |
| 4,367,353 A | 1/1983 | Inglis |
| 4,370,156 A | 1/1983 | Goddin, Jr. et al. |
| 4,375,566 A | 3/1983 | Kawamata et al. |
| 4,394,303 A | 7/1983 | Gibson |
| 4,418,045 A | 11/1983 | Sato et al. |
| 4,433,185 A | 2/1984 | Tabak |
| 4,439,213 A | 3/1984 | Frey et al. |
| 4,440,956 A | 4/1984 | Couvillion |
| 4,465,887 A | 8/1984 | Schammel |
| 4,469,905 A | 9/1984 | Inwood et al. |
| 4,481,305 A | 11/1984 | Jorn et al. |
| 4,489,215 A | 12/1984 | Withers |
| 4,511,747 A | 4/1985 | Wright et al. |
| 4,519,824 A | 5/1985 | Huebel |
| 4,523,049 A | 6/1985 | Jones et al. |
| 4,551,438 A | 11/1985 | Miller |
| 4,552,644 A | 11/1985 | Johnson et al. |
| 4,554,395 A | 11/1985 | Jones et al. |
| 4,567,307 A | 1/1986 | Jones et al. |
| 4,605,488 A | 8/1986 | Chester et al. |
| 4,629,718 A | 12/1986 | Jones et al. |
| 4,673,664 A | 6/1987 | Bambrick |
| 4,717,782 A | 1/1988 | Garwood et al. |
| 4,751,336 A | 6/1988 | Jezl et al. |
| 4,754,091 A | 6/1988 | Jezl et al. |
| 4,754,093 A | 6/1988 | Jezl et al. |
| 4,769,047 A | 9/1988 | Dye |
| 4,777,313 A | 10/1988 | Sofranko et al. |
| 4,814,539 A | 3/1989 | Jezl et al. |
| 4,822,477 A | 4/1989 | Avidan et al. |
| 4,822,944 A | 4/1989 | Brazdil, Jr. et al. |
| 4,831,203 A | 5/1989 | Owen et al. |
| 4,835,331 A | 5/1989 | Hammershaimb et al. |
| 4,849,571 A | 7/1989 | Gaffney |
| 4,855,524 A | 8/1989 | Harandi et al. |
| 4,855,528 A | 8/1989 | Young et al. |
| 4,861,934 A | 8/1989 | Suzuki et al. |
| 4,865,820 A | 9/1989 | Dunster et al. |
| 4,882,400 A | 11/1989 | Dumain et al. |
| 4,889,545 A | 12/1989 | Campbell et al. |
| 4,891,457 A | 1/1990 | Owen et al. |
| 4,895,823 A | 1/1990 | Kolts et al. |
| 4,900,347 A | 2/1990 | McCue, Jr. et al. |
| 4,935,568 A | 6/1990 | Harandi et al. |
| 4,939,311 A | 7/1990 | Washecheck et al. |
| 4,939,312 A | 7/1990 | Baerns et al. |
| 4,950,311 A | 8/1990 | White, Jr. |
| 4,962,261 A | 10/1990 | Abrevaya et al. |
| 4,966,874 A | 10/1990 | Young et al. |
| 5,003,124 A | 3/1991 | Smith, Jr. et al. |
| 5,004,852 A | 4/1991 | Harandi |
| 5,012,028 A | 4/1991 | Gupta et al. |
| 5,015,799 A | 5/1991 | Walker et al. |
| 5,024,984 A | 6/1991 | Kaminsky et al. |
| 5,025,108 A | 6/1991 | Cameron et al. |
| 5,026,934 A | 6/1991 | Bains et al. |
| 5,034,565 A | 7/1991 | Harandi et al. |
| 5,041,405 A | 8/1991 | Lunsford et al. |
| 5,055,627 A | 10/1991 | Smith, Jr. et al. |
| 5,057,468 A | 10/1991 | Adams |
| 5,057,638 A | 10/1991 | Sweeney |
| 5,066,629 A | 11/1991 | Lukey et al. |
| 5,080,872 A | 1/1992 | Jezl et al. |

(56) References Cited

U.S. PATENT DOCUMENTS

| | | |
|---|---|---|
| 5,082,819 A | 1/1992 | Boeck et al. |
| 5,095,161 A | 3/1992 | Abrevaya et al. |
| 5,113,032 A | 5/1992 | Cameron et al. |
| 5,118,898 A | 6/1992 | Tyler et al. |
| 5,132,472 A | 7/1992 | Durante et al. |
| 5,137,862 A | 8/1992 | Mackrodt et al. |
| 5,168,090 A | 12/1992 | Ebner et al. |
| 5,179,056 A | 1/1993 | Bartley |
| 5,196,634 A | 3/1993 | Washecheck et al. |
| 5,198,596 A | 3/1993 | Kaminsky et al. |
| 5,240,474 A | 8/1993 | Auvil et al. |
| 5,245,099 A | 9/1993 | Mitariten |
| 5,254,781 A | 10/1993 | Calamur et al. |
| 5,263,998 A | 11/1993 | Mackrodt et al. |
| 5,288,935 A | 2/1994 | Alario et al. |
| 5,292,979 A | 3/1994 | Chauvin et al. |
| 5,306,854 A | 4/1994 | Choudhary et al. |
| 5,312,795 A | 5/1994 | Kaminsky et al. |
| 5,316,995 A | 5/1994 | Kaminsky et al. |
| 5,326,915 A | 7/1994 | Viola et al. |
| 5,328,883 A | 7/1994 | Washecheck et al. |
| 5,336,825 A | 8/1994 | Choudhary et al. |
| 5,336,826 A | 8/1994 | Brophy et al. |
| 5,345,023 A | 9/1994 | Chauvin et al. |
| 5,348,642 A | 9/1994 | Serrand et al. |
| 5,371,306 A | 12/1994 | Woo et al. |
| 5,395,981 A | 3/1995 | Marker |
| 5,414,157 A | 5/1995 | Durante et al. |
| 5,414,170 A | 5/1995 | McCue et al. |
| 5,430,219 A | 7/1995 | Sanfilippo et al. |
| 5,449,850 A | 9/1995 | Young et al. |
| 5,457,256 A | 10/1995 | Mitariten et al. |
| 5,462,583 A | 10/1995 | Wood et al. |
| 5,473,027 A | 12/1995 | Batchelor et al. |
| 5,500,149 A | 3/1996 | Green et al. |
| 5,523,493 A | 6/1996 | Cameron et al. |
| 5,568,737 A | 10/1996 | Campbell et al. |
| 5,599,510 A | 2/1997 | Kaminsky et al. |
| 5,633,422 A | 5/1997 | Murray |
| 5,659,090 A | 8/1997 | Cameron et al. |
| 5,670,442 A | 9/1997 | Fornasari et al. |
| RE35,632 E | 10/1997 | Leyshon |
| RE35,633 E | 10/1997 | Leyshon |
| 5,679,241 A | 10/1997 | Stanley et al. |
| 5,702,589 A | 12/1997 | Tsang et al. |
| 5,712,217 A | 1/1998 | Choudhary et al. |
| 5,714,657 A | 2/1998 | deVries |
| 5,723,713 A | 3/1998 | Maunders |
| 5,736,107 A | 4/1998 | Inomata et al. |
| 5,744,015 A | 4/1998 | Mazanec et al. |
| 5,749,937 A | 5/1998 | Detering et al. |
| 5,750,821 A | 5/1998 | Inomata et al. |
| 5,763,722 A | 6/1998 | Vic et al. |
| 5,792,895 A | 8/1998 | Commereuc et al. |
| 5,811,618 A | 9/1998 | Wu |
| 5,811,619 A | 9/1998 | Commereuc et al. |
| 5,817,904 A | 10/1998 | Vic et al. |
| 5,817,905 A | 10/1998 | Commereuc et al. |
| 5,819,555 A | 10/1998 | Engdahl |
| 5,830,822 A | 11/1998 | Euzen |
| 5,849,973 A | 12/1998 | Van Der Vaart |
| 5,856,257 A | 1/1999 | Freeman et al. |
| 5,861,353 A | 1/1999 | Viola et al. |
| 5,866,737 A | 2/1999 | Hagemeyer et al. |
| 5,877,363 A | 3/1999 | Gildert et al. |
| 5,877,368 A | 3/1999 | Kiyama et al. |
| 5,897,945 A | 4/1999 | Lieber et al. |
| 5,917,136 A | 6/1999 | Gaffney et al. |
| 5,935,293 A | 8/1999 | Detering et al. |
| 5,935,897 A | 8/1999 | Trubenbach et al. |
| 5,935,898 A | 8/1999 | Trubenbach et al. |
| 5,936,135 A | 8/1999 | Choudhary et al. |
| 5,959,170 A | 9/1999 | Withers, Jr. |
| 6,005,121 A | 12/1999 | Ebner et al. |
| 6,013,851 A | 1/2000 | Verrelst et al. |
| 6,020,533 A | 2/2000 | Lewis et al. |
| 6,030,598 A | 2/2000 | Topham et al. |
| 6,031,145 A | 2/2000 | Commereuc et al. |
| 6,087,545 A | 7/2000 | Choudhary et al. |
| 6,096,934 A | 8/2000 | Rekoske |
| 6,103,654 A | 8/2000 | Commereuc et al. |
| 6,110,979 A | 8/2000 | Nataraj et al. |
| 6,114,400 A | 9/2000 | Nataraj et al. |
| 6,140,535 A | 10/2000 | Williams |
| 6,146,549 A | 11/2000 | MacKay et al. |
| 6,153,149 A | 11/2000 | Rabitz et al. |
| 6,221,986 B1 | 4/2001 | Commereuc et al. |
| 6,328,945 B1 | 12/2001 | Hufton et al. |
| 6,342,149 B1 | 1/2002 | K?ster et al. |
| 6,355,093 B1 | 3/2002 | Schwartz et al. |
| 6,380,451 B1 | 4/2002 | Kreischer et al. |
| 6,403,523 B1 | 6/2002 | Cantrell et al. |
| RE37,853 E | 9/2002 | Detering et al. |
| 6,444,869 B2 | 9/2002 | Senetar et al. |
| 6,447,745 B1 | 9/2002 | Feeley et al. |
| 6,455,015 B1 | 9/2002 | Kilroy |
| 6,468,501 B1 | 10/2002 | Chen et al. |
| 6,486,373 B1 | 11/2002 | Abichandani et al. |
| 6,492,571 B1 | 12/2002 | He et al. |
| 6,509,292 B1 | 1/2003 | Blankenship et al. |
| 6,518,220 B2 | 2/2003 | Walsdorff et al. |
| 6,518,476 B1 | 2/2003 | Culp et al. |
| 6,538,169 B1 | 3/2003 | Pittman et al. |
| 6,576,803 B2 | 6/2003 | Cantrell et al. |
| 6,596,912 B1 | 7/2003 | Lunsford et al. |
| 6,602,920 B2 | 8/2003 | Hall et al. |
| 6,610,124 B1 | 8/2003 | Dolan et al. |
| 6,660,812 B2 | 12/2003 | Kuechler et al. |
| 6,660,894 B1 | 12/2003 | Wu et al. |
| 6,683,019 B2 | 1/2004 | Gartside et al. |
| 6,703,429 B2 | 3/2004 | O'Rear et al. |
| 6,713,657 B2 | 3/2004 | O'Rear et al. |
| 6,726,832 B1 | 4/2004 | Baldassari et al. |
| 6,726,850 B1 | 4/2004 | Reyes et al. |
| 6,730,808 B2 | 5/2004 | Bitterlich et al. |
| 6,747,066 B2 | 6/2004 | Wang et al. |
| 6,759,562 B2 | 7/2004 | Gartside et al. |
| 6,761,838 B2 | 7/2004 | Zeng et al. |
| 6,764,602 B2 | 7/2004 | Shutt et al. |
| 6,768,035 B2 | 7/2004 | O'Rear et al. |
| 6,821,500 B2 | 11/2004 | Fincke et al. |
| 6,841,708 B1 | 1/2005 | Benje |
| 6,891,001 B2 | 5/2005 | Kuhlburger |
| 6,914,165 B2 | 7/2005 | Flego et al. |
| 6,964,934 B2 | 11/2005 | Brady et al. |
| 7,093,445 B2 | 8/2006 | Corr, II et al. |
| 7,105,147 B2 | 9/2006 | Kurimura et al. |
| 7,129,195 B2 | 10/2006 | Felder et al. |
| 7,157,612 B2 | 1/2007 | Ewert et al. |
| 7,164,052 B2 | 1/2007 | Carati et al. |
| 7,176,342 B2 | 2/2007 | Bellussi et al. |
| 7,183,451 B2 | 2/2007 | Gattis et al. |
| 7,196,238 B2 | 3/2007 | Nurminen et al. |
| 7,199,273 B2 | 4/2007 | Molinier et al. |
| 7,208,647 B2 | 4/2007 | Peterson et al. |
| 7,214,841 B2 | 5/2007 | Gartside et al. |
| 7,250,543 B2 | 7/2007 | Bagherzadeh et al. |
| 7,291,321 B2 | 11/2007 | Bagherzadeh et al. |
| 7,316,804 B2 | 1/2008 | Taheri et al. |
| 7,361,622 B2 | 4/2008 | Benderly et al. |
| 7,473,814 B2 | 1/2009 | Basset et al. |
| 7,485,595 B2 | 2/2009 | Long et al. |
| 7,525,002 B2 | 4/2009 | Umansky et al. |
| 7,547,813 B2 | 6/2009 | Smith et al. |
| 7,550,644 B2 | 6/2009 | Pfefferle |
| 7,566,428 B2 | 7/2009 | Warner et al. |
| 7,576,296 B2 | 8/2009 | Fincke et al. |
| 7,579,509 B2 | 8/2009 | Benje et al. |
| 7,589,246 B2 | 9/2009 | Iaccino et al. |
| 7,659,437 B2 | 2/2010 | Iaccino et al. |
| 7,663,011 B2 | 2/2010 | Shan et al. |
| 7,667,085 B2 | 2/2010 | Gattis et al. |
| 7,671,244 B2 | 3/2010 | Hafenscher et al. |
| 7,683,227 B2 | 3/2010 | Iaccino et al. |

(56) References Cited

U.S. PATENT DOCUMENTS

| | | |
|---|---|---|
| 7,687,041 B2 | 3/2010 | Singh |
| 7,687,048 B1 | 3/2010 | Schultz et al. |
| 7,728,186 B2 | 6/2010 | Iaccino et al. |
| 7,781,636 B2 | 8/2010 | Iaccino et al. |
| 7,790,012 B2 | 9/2010 | Kirk et al. |
| 7,790,776 B2 | 9/2010 | Christensen et al. |
| 7,793,517 B2 | 9/2010 | Patel et al. |
| 7,795,490 B2 | 9/2010 | Iaccino et al. |
| 7,799,209 B2 | 9/2010 | Petri |
| 7,799,730 B2 | 9/2010 | Ringer et al. |
| 7,838,710 B2 | 11/2010 | Ryu |
| 7,868,216 B2 | 1/2011 | Chodorge et al. |
| 7,879,119 B2 | 2/2011 | Abughazaleh et al. |
| 7,888,541 B2 | 2/2011 | Gartside et al. |
| 7,888,543 B2 | 2/2011 | Iaccino et al. |
| 7,902,113 B2 | 3/2011 | Zarrinpashne et al. |
| 7,915,461 B2 | 3/2011 | Gattis et al. |
| 7,915,462 B2 | 3/2011 | Gattis et al. |
| 7,915,463 B2 | 3/2011 | Gattis et al. |
| 7,915,464 B2 | 3/2011 | Gattis et al. |
| 7,915,465 B2 | 3/2011 | Gattis et al. |
| 7,915,466 B2 | 3/2011 | Gattis et al. |
| 7,932,296 B2 | 4/2011 | Malhotra et al. |
| 7,968,020 B2 | 6/2011 | Behelfer et al. |
| 7,968,759 B2 | 6/2011 | Iaccino et al. |
| 7,977,519 B2 | 7/2011 | Iaccino et al. |
| 7,993,500 B2 | 8/2011 | Gilliam et al. |
| 7,993,599 B2 | 8/2011 | Leveson |
| 8,021,620 B2 | 9/2011 | Nicholas et al. |
| 8,071,836 B2 | 12/2011 | Butler |
| 8,080,215 B2 | 12/2011 | Taheri et al. |
| 8,119,848 B2 | 2/2012 | Cross, Jr. et al. |
| 8,129,305 B2 | 3/2012 | Bagherzadeh et al. |
| 8,137,444 B2 | 3/2012 | Farsad et al. |
| 8,153,851 B2 | 4/2012 | Gartside et al. |
| 8,163,070 B2 | 4/2012 | Hees et al. |
| 8,192,709 B2 | 6/2012 | Reyes et al. |
| 8,227,650 B2 | 7/2012 | Putman et al. |
| 8,232,415 B2 | 7/2012 | Taheri et al. |
| 8,258,358 B2 | 9/2012 | Gartside et al. |
| 8,269,055 B2 | 9/2012 | Fritz et al. |
| 8,277,525 B2 | 10/2012 | Dalton |
| 8,293,805 B2 | 10/2012 | Khan et al. |
| 8,399,527 B1 | 3/2013 | Brown et al. |
| 8,399,726 B2 | 3/2013 | Chinta et al. |
| 8,404,189 B2 | 3/2013 | Andresen et al. |
| 8,435,920 B2 | 5/2013 | White et al. |
| 8,450,546 B2 | 5/2013 | Chinta et al. |
| 8,524,625 B2 | 9/2013 | Dight et al. |
| 8,552,236 B2 | 10/2013 | Iaccino |
| 8,557,728 B2 | 10/2013 | Birdsall et al. |
| 8,575,410 B2 | 11/2013 | Nicholas et al. |
| 8,624,042 B2 | 1/2014 | Grasset et al. |
| 8,658,750 B2 | 2/2014 | Lattner et al. |
| 8,669,171 B2 | 3/2014 | Perraud et al. |
| 8,710,286 B2 | 4/2014 | Butler |
| 8,729,328 B2 | 5/2014 | Chinta et al. |
| 8,742,189 B2 | 6/2014 | Kiesslich et al. |
| 8,742,192 B2 | 6/2014 | Godsmark et al. |
| 8,748,681 B2 | 6/2014 | Nicholas et al. |
| 8,748,682 B2 | 6/2014 | Nicholas et al. |
| 8,759,598 B2 | 6/2014 | Hayashi et al. |
| 8,765,660 B1 | 7/2014 | Li et al. |
| 8,796,497 B2 | 8/2014 | Chinta et al. |
| 8,865,780 B2 | 10/2014 | Bogild Hansen |
| 8,912,109 B2 | 12/2014 | Chinta et al. |
| 8,912,381 B2 | 12/2014 | Chinta et al. |
| 8,921,256 B2 | 12/2014 | Cizeron et al. |
| 8,962,517 B2 | 2/2015 | Zurcher et al. |
| 8,993,473 B2 | 3/2015 | Melde et al. |
| 9,040,762 B2 | 5/2015 | Cizeron et al. |
| 9,079,815 B2 | 7/2015 | Mukherjee et al. |
| 9,133,079 B2 | 9/2015 | Weinberger et al. |
| 9,321,702 B2 | 4/2016 | Nyce et al. |
| 9,321,703 B2 | 4/2016 | Nyce et al. |
| 9,328,297 B1 | 5/2016 | Nyce et al. |
| 9,334,204 B1* | 5/2016 | Radaelli ............... B01J 8/001 |
| 9,352,295 B2* | 5/2016 | Rafique ............... C07C 4/02 |
| 9,371,257 B2 | 6/2016 | Chinta et al. |
| 9,376,324 B2 | 6/2016 | Senderov et al. |
| 9,446,343 B2 | 9/2016 | Elliott et al. |
| 9,446,397 B2 | 9/2016 | Gamoras et al. |
| 9,469,577 B2 | 10/2016 | Schammel et al. |
| 9,512,047 B2 | 12/2016 | Nyce et al. |
| 9,527,784 B2 | 12/2016 | Weinberger et al. |
| 9,556,086 B2 | 1/2017 | Schammel et al. |
| 9,567,269 B2* | 2/2017 | Radaelli ............... C07C 1/04 |
| 9,598,328 B2 | 3/2017 | Nyce et al. |
| 9,670,113 B2 | 6/2017 | Iyer et al. |
| 9,682,900 B2 | 6/2017 | Keusenkothen et al. |
| 9,701,597 B2 | 7/2017 | Rafique et al. |
| 9,718,054 B2 | 8/2017 | Scher et al. |
| 9,738,571 B2 | 8/2017 | Schammel et al. |
| 9,751,079 B2 | 9/2017 | Freer et al. |
| 9,751,818 B2 | 9/2017 | Zurcher et al. |
| 9,790,144 B2 | 10/2017 | Radaelli et al. |
| 9,944,573 B2 | 4/2018 | Radaelli et al. |
| 9,950,971 B2 | 4/2018 | Henao et al. |
| 9,956,544 B2 | 5/2018 | Schammel et al. |
| 9,969,660 B2 | 5/2018 | Iyer et al. |
| 9,975,767 B2 | 5/2018 | Farnell |
| 10,047,020 B2 | 8/2018 | Cizeron et al. |
| 10,195,603 B2 | 2/2019 | Scher et al. |
| 10,300,465 B2 | 5/2019 | Freer et al. |
| 10,301,234 B2 | 5/2019 | Nyce et al. |
| 10,308,565 B2 | 6/2019 | Schammel et al. |
| 10,377,682 B2 | 8/2019 | Rafique et al. |
| 10,407,361 B2 | 9/2019 | Radaelli et al. |
| 10,787,398 B2 | 9/2020 | Nyce et al. |
| 10,787,400 B2 | 9/2020 | Radaelli et al. |
| 10,793,490 B2 | 10/2020 | Radaelli et al. |
| 2002/0007101 A1 | 1/2002 | Senetar et al. |
| 2002/0015670 A1 | 2/2002 | Shah et al. |
| 2002/0150522 A1 | 10/2002 | Heim et al. |
| 2002/0182735 A1 | 12/2002 | Kibby et al. |
| 2003/0033932 A1 | 2/2003 | Sirkar et al. |
| 2003/0045761 A1 | 3/2003 | Kuechler et al. |
| 2003/0072700 A1 | 4/2003 | Goebel et al. |
| 2003/0094398 A1 | 5/2003 | Porter et al. |
| 2003/0189202 A1 | 10/2003 | Li et al. |
| 2003/0233019 A1 | 12/2003 | Sherwood |
| 2004/0158113 A1 | 8/2004 | Srinivas et al. |
| 2004/0220053 A1 | 11/2004 | Bagherzadeh et al. |
| 2004/0231586 A1 | 11/2004 | Dugue et al. |
| 2004/0242940 A1 | 12/2004 | Takahashi et al. |
| 2005/0065391 A1 | 3/2005 | Gattis et al. |
| 2005/0065392 A1 | 3/2005 | Peterson et al. |
| 2005/0107650 A1 | 5/2005 | Sumner |
| 2005/0154228 A1 | 7/2005 | Nakajima et al. |
| 2005/0239634 A1 | 10/2005 | Ying et al. |
| 2006/0018821 A1 | 1/2006 | Suzuki et al. |
| 2006/0021379 A1 | 2/2006 | Ronczy |
| 2006/0063955 A1 | 3/2006 | Lacombe et al. |
| 2006/0155157 A1 | 7/2006 | Zarrinpashne et al. |
| 2006/0194995 A1 | 8/2006 | Umansky et al. |
| 2006/0235246 A1 | 10/2006 | Smith et al. |
| 2006/0283780 A1 | 12/2006 | Spivey et al. |
| 2007/0027030 A1 | 2/2007 | Cheung et al. |
| 2007/0073083 A1 | 3/2007 | Sunley |
| 2007/0083073 A1 | 4/2007 | Bagherzadeh et al. |
| 2007/0112236 A1 | 5/2007 | Bridges et al. |
| 2007/0135668 A1 | 6/2007 | Sumner |
| 2007/0244347 A1 | 10/2007 | Ying et al. |
| 2008/0121383 A1 | 5/2008 | Birk |
| 2008/0138274 A1 | 6/2008 | Garcia-Martinez |
| 2008/0141713 A1 | 6/2008 | Verma |
| 2008/0154078 A1 | 6/2008 | Bozzano et al. |
| 2008/0194900 A1 | 8/2008 | Bhirud |
| 2008/0207975 A1 | 8/2008 | Crone et al. |
| 2008/0267852 A1 | 10/2008 | Schumacher et al. |
| 2008/0275143 A1 | 11/2008 | Malhotra et al. |
| 2008/0281136 A1 | 11/2008 | Bagherzadeh et al. |
| 2008/0293980 A1 | 11/2008 | Kiesslich et al. |
| 2008/0300436 A1 | 12/2008 | Cheung et al. |

(56) References Cited

U.S. PATENT DOCUMENTS

| | | |
|---|---|---|
| 2009/0005236 A1 | 1/2009 | Ying et al. |
| 2009/0042998 A1 | 2/2009 | Hashimoto et al. |
| 2009/0043141 A1 | 2/2009 | Mazanec et al. |
| 2009/0087496 A1 | 4/2009 | Katusic et al. |
| 2009/0105066 A1 | 4/2009 | Kang et al. |
| 2009/0110631 A1 | 4/2009 | Garcia-Martinez et al. |
| 2009/0202427 A1 | 8/2009 | Katusic et al. |
| 2009/0203946 A1 | 8/2009 | Chuang |
| 2009/0209412 A1 | 8/2009 | Parent et al. |
| 2009/0209794 A1 | 8/2009 | Lauritzen et al. |
| 2009/0216059 A1 | 8/2009 | Reyes et al. |
| 2009/0259076 A1 | 10/2009 | Simmons et al. |
| 2009/0264693 A1 | 10/2009 | Xie et al. |
| 2009/0267852 A1 | 10/2009 | Tahmisian, Jr. et al. |
| 2009/0277837 A1 | 11/2009 | Liu et al. |
| 2009/0312583 A1 | 12/2009 | Sigl et al. |
| 2009/0312591 A1 | 12/2009 | Schubert et al. |
| 2010/0000153 A1 | 1/2010 | Kurkjian et al. |
| 2010/0003179 A1 | 1/2010 | Katusic et al. |
| 2010/0028735 A1 | 2/2010 | Basset et al. |
| 2010/0140144 A1 | 6/2010 | Clinton et al. |
| 2010/0185034 A1 | 7/2010 | Nishimura et al. |
| 2010/0191031 A1 | 7/2010 | Sundaram |
| 2010/0197482 A1 | 8/2010 | Basset et al. |
| 2010/0197986 A1 | 8/2010 | Midorikawa et al. |
| 2010/0222203 A1 | 9/2010 | Baba et al. |
| 2010/0249473 A1 | 9/2010 | Butler |
| 2010/0256245 A1 | 10/2010 | Iaccino et al. |
| 2010/0331174 A1 | 12/2010 | Chinta et al. |
| 2010/0331593 A1 | 12/2010 | Chinta et al. |
| 2010/0331595 A1 | 12/2010 | Chinta et al. |
| 2011/0036728 A1 | 2/2011 | Farsad |
| 2011/0049132 A1 | 3/2011 | Lee |
| 2011/0052466 A1 | 3/2011 | Liu |
| 2011/0071331 A1 | 3/2011 | Basset et al. |
| 2011/0124488 A1 | 5/2011 | Neltner et al. |
| 2011/0160508 A1 | 6/2011 | Ma et al. |
| 2011/0171121 A1 | 7/2011 | Senderov et al. |
| 2011/0189559 A1 | 8/2011 | De Miranda et al. |
| 2011/0230690 A1 | 9/2011 | Tiita et al. |
| 2011/0240926 A1 | 10/2011 | Schellen et al. |
| 2011/0257453 A1 | 10/2011 | Chinta et al. |
| 2011/0257454 A1 | 10/2011 | Thorman et al. |
| 2011/0263917 A1 | 10/2011 | Van Hal et al. |
| 2011/0315012 A1 | 12/2011 | Kuznicki et al. |
| 2012/0006054 A1 | 1/2012 | Keller |
| 2012/0041246 A1 | 2/2012 | Scher et al. |
| 2012/0065412 A1 | 3/2012 | Abdallah et al. |
| 2012/0095275 A1 | 4/2012 | Coleman et al. |
| 2012/0129690 A1 | 5/2012 | Larcher et al. |
| 2012/0172648 A1 | 7/2012 | Seebauer |
| 2012/0197053 A1 | 8/2012 | Cantrell et al. |
| 2012/0198769 A1 | 8/2012 | Schirrmeister et al. |
| 2012/0202986 A1 | 8/2012 | Hassan et al. |
| 2012/0204716 A1 | 8/2012 | Schirrmeister et al. |
| 2012/0215045 A1 | 8/2012 | Butler |
| 2012/0222422 A1 | 9/2012 | Nunley et al. |
| 2012/0258852 A1 | 10/2012 | Martinez et al. |
| 2012/0277474 A1 | 11/2012 | Graham Ronald et al. |
| 2012/0302807 A1 | 11/2012 | Elseviers |
| 2013/0023708 A1 | 1/2013 | Majumder et al. |
| 2013/0023709 A1 | 1/2013 | Cizeron et al. |
| 2013/0025201 A1 | 1/2013 | Dalton |
| 2013/0040806 A1 | 2/2013 | Dismukes et al. |
| 2013/0042480 A1 | 2/2013 | Turulin |
| 2013/0142707 A1 | 6/2013 | Chinta et al. |
| 2013/0158322 A1 | 6/2013 | Nyce et al. |
| 2013/0165728 A1 | 6/2013 | Zurcher et al. |
| 2013/0172649 A1 | 7/2013 | Chinta et al. |
| 2013/0178680 A1 | 7/2013 | Ha et al. |
| 2013/0183231 A1 | 7/2013 | Senderov et al. |
| 2013/0225880 A1 | 8/2013 | Brown et al. |
| 2013/0225884 A1 | 8/2013 | Weinberger et al. |
| 2013/0253248 A1 | 9/2013 | Gamoras et al. |
| 2013/0270180 A1 | 10/2013 | Zhang et al. |
| 2013/0289324 A1 | 10/2013 | Price et al. |
| 2013/0291720 A1 | 11/2013 | Blood et al. |
| 2013/0292300 A1 | 11/2013 | Ying et al. |
| 2014/0012053 A1 | 1/2014 | Iyer et al. |
| 2014/0018589 A1 | 1/2014 | Iyer et al. |
| 2014/0061540 A1 | 3/2014 | Long et al. |
| 2014/0080699 A1 | 3/2014 | Ghose et al. |
| 2014/0107385 A1 | 4/2014 | Schammel et al. |
| 2014/0121433 A1 | 5/2014 | Cizeron et al. |
| 2014/0128484 A1 | 5/2014 | Hassan et al. |
| 2014/0128485 A1 | 5/2014 | Hassan et al. |
| 2014/0135552 A1 | 5/2014 | Nicholas et al. |
| 2014/0135553 A1 | 5/2014 | Nicholas et al. |
| 2014/0135554 A1 | 5/2014 | Nicholas et al. |
| 2014/0171707 A1 | 6/2014 | Nyce et al. |
| 2014/0181877 A1 | 6/2014 | Haykinson et al. |
| 2014/0194663 A1 | 7/2014 | Butler |
| 2014/0194664 A1 | 7/2014 | Sawyer et al. |
| 2014/0235911 A1 | 8/2014 | Laha |
| 2014/0249339 A1 | 9/2014 | Simanzhenkov et al. |
| 2014/0274671 A1 | 9/2014 | Schammel et al. |
| 2014/0275619 A1 | 9/2014 | Chen et al. |
| 2014/0377137 A1 | 12/2014 | Mignon et al. |
| 2014/0378728 A1 | 12/2014 | Davis et al. |
| 2015/0010467 A1 | 1/2015 | Ito et al. |
| 2015/0038750 A1 | 2/2015 | Weiss et al. |
| 2015/0045599 A1 | 2/2015 | Frey et al. |
| 2015/0065767 A1 | 3/2015 | Henao et al. |
| 2015/0099914 A1 | 4/2015 | Garza et al. |
| 2015/0152025 A1 | 6/2015 | Cizeron et al. |
| 2015/0210610 A1 | 7/2015 | Rafique et al. |
| 2015/0218786 A1 | 8/2015 | Cullen |
| 2015/0232395 A1 | 8/2015 | Nyce et al. |
| 2015/0246856 A1 | 9/2015 | Schmigalle et al. |
| 2015/0307415 A1 | 10/2015 | Rafique et al. |
| 2015/0314267 A1 | 11/2015 | Schammel et al. |
| 2015/0321974 A1 | 11/2015 | Schammel et al. |
| 2015/0329438 A1 | 11/2015 | Nyce et al. |
| 2015/0329439 A1 | 11/2015 | Nyce et al. |
| 2015/0368167 A1 | 12/2015 | Weinberger et al. |
| 2015/0376527 A1 | 12/2015 | Xu |
| 2016/0074844 A1 | 3/2016 | Freer et al. |
| 2016/0089637 A1 | 3/2016 | Chang et al. |
| 2016/0167973 A1 | 6/2016 | Boorse et al. |
| 2016/0200643 A1 | 7/2016 | Nyce et al. |
| 2016/0237003 A1 | 8/2016 | Mammadov et al. |
| 2016/0250618 A1 | 9/2016 | Long et al. |
| 2016/0272556 A1 | 9/2016 | Rafique et al. |
| 2016/0272557 A1 | 9/2016 | Radaelli et al. |
| 2016/0289143 A1 | 10/2016 | Duggal et al. |
| 2016/0318828 A1 | 11/2016 | Washburn et al. |
| 2016/0368834 A1 | 12/2016 | Nyce et al. |
| 2016/0376148 A1 | 12/2016 | Mamedov et al. |
| 2017/0014807 A1 | 1/2017 | Liang et al. |
| 2017/0022125 A1 | 1/2017 | Fichtl |
| 2017/0057889 A1 | 3/2017 | Sarsani et al. |
| 2017/0106327 A1 | 4/2017 | Sadasivan Vijayakumari et al. |
| 2017/0107162 A1 | 4/2017 | Duggal et al. |
| 2017/0113980 A1 | 4/2017 | Radaelli et al. |
| 2017/0190638 A1 | 7/2017 | Liang et al. |
| 2017/0247803 A1 | 8/2017 | Sofranko |
| 2017/0260114 A1 | 9/2017 | Nyce et al. |
| 2017/0267605 A1 | 9/2017 | Tanur et al. |
| 2017/0275217 A1 | 9/2017 | Weinberger et al. |
| 2017/0283345 A1 | 10/2017 | Schammel et al. |
| 2017/0297975 A1 | 10/2017 | Radaelli et al. |
| 2017/0320793 A1 | 11/2017 | Fritz |
| 2017/0341997 A1 | 11/2017 | Nyce et al. |
| 2018/0118637 A1 | 5/2018 | Zurcher et al. |
| 2018/0162785 A1 | 6/2018 | Liang et al. |
| 2018/0169561 A1 | 6/2018 | Jonnavittula et al. |
| 2018/0179125 A1 | 6/2018 | Radaelli et al. |
| 2018/0186707 A1 | 7/2018 | Abudawoud et al. |
| 2018/0215682 A1 | 8/2018 | Rafique et al. |
| 2018/0222818 A1 | 8/2018 | Radaelli et al. |
| 2018/0272303 A1 | 9/2018 | Simanzhenkov et al. |
| 2018/0282658 A1 | 10/2018 | Takahama et al. |
| 2018/0305273 A1 | 10/2018 | Patel et al. |
| 2018/0305274 A1 | 10/2018 | Rafique et al. |

(56) References Cited

U.S. PATENT DOCUMENTS

| | | |
|---|---|---|
| 2018/0327334 A1 | 11/2018 | Radaelli et al. |
| 2018/0353940 A1 | 12/2018 | Liang et al. |
| 2019/0010096 A1 | 1/2019 | Schammel et al. |
| 2019/0062642 A1 | 2/2019 | Wei et al. |
| 2019/0119182 A1 | 4/2019 | McCormick et al. |
| 2019/0143288 A1 | 5/2019 | Bao et al. |
| 2019/0169089 A1 | 6/2019 | Cizeron et al. |
| 2019/0169090 A1 | 6/2019 | Sarsani et al. |
| 2019/0177246 A1 | 6/2019 | Nyce et al. |
| 2019/0389788 A1 | 12/2019 | Mamedov et al. |
| 2020/0031734 A1 | 1/2020 | Cizeron et al. |
| 2020/0031736 A1 | 1/2020 | Weinberger et al. |
| 2020/0048165 A1 | 2/2020 | Duggal et al. |
| 2020/0054983 A1 | 2/2020 | Jonnavittula et al. |
| 2020/0055796 A1 | 2/2020 | Nyce et al. |
| 2020/0071242 A1 | 3/2020 | Patel et al. |
| 2020/0131100 A1 | 4/2020 | Schammel et al. |
| 2020/0172452 A1 | 6/2020 | Duggal et al. |
| 2020/0189994 A1 | 6/2020 | Radaelli et al. |
| 2020/0207684 A1 | 7/2020 | Rafique et al. |
| 2020/0207685 A1 | 7/2020 | Nyce et al. |
| 2020/0216370 A1 | 7/2020 | Rafique et al. |
| 2020/0231519 A1 | 7/2020 | Abudawoud et al. |

FOREIGN PATENT DOCUMENTS

| | | |
|---|---|---|
| CA | 2800142 C | 6/2018 |
| CN | 1403375 A | 3/2003 |
| CN | 1432550 A | 7/2003 |
| CN | 101224432 A | 7/2008 |
| CN | 101387019 A | 3/2009 |
| CN | 101747927 A | 6/2010 |
| CN | 102093157 A | 6/2011 |
| CN | 102125825 A | 7/2011 |
| CN | 102950017 A | 3/2013 |
| DE | 1905517 A1 | 8/1970 |
| DE | 2540257 A1 | 4/1977 |
| DE | 3406751 A1 | 8/1985 |
| DE | 4039960 A1 | 9/1991 |
| DE | 4338414 C1 | 3/1995 |
| DE | 4338416 C1 | 4/1995 |
| DE | 102011080294 A1 | 2/2013 |
| EP | 106392 A1 | 4/1984 |
| EP | 177327 A2 | 4/1986 |
| EP | 253522 A2 | 1/1988 |
| EP | 303438 A2 | 2/1989 |
| EP | 336823 A1 | 10/1989 |
| EP | 608447 A1 | 8/1994 |
| EP | 634211 A1 | 1/1995 |
| EP | 722822 A1 | 7/1996 |
| EP | 761307 A1 | 3/1997 |
| EP | 764467 A1 | 3/1997 |
| EP | 716064 B1 | 7/1998 |
| EP | 1110930 A1 | 6/2001 |
| EP | 1632467 A1 | 3/2006 |
| EP | 1749807 A1 | 2/2007 |
| EP | 1749806 B1 | 10/2008 |
| EP | 3081292 A1 | 10/2016 |
| FR | 649429 A | 12/1928 |
| FR | 2600556 A1 | 12/1987 |
| GB | 733336 A | 7/1955 |
| GB | 2191212 A | 12/1987 |
| JP | 2005161225 A | 6/2005 |
| RU | 2412147 C2 | 2/2011 |
| RU | 2447048 C1 | 4/2012 |
| WO | 8607351 A1 | 12/1986 |
| WO | 0204119 A1 | 1/2002 |
| WO | 2004033488 A2 | 4/2004 |
| WO | 2004056479 A1 | 7/2004 |
| WO | 2004103936 A1 | 12/2004 |
| WO | 2005067683 A2 | 7/2005 |
| WO | 2007125360 A1 | 11/2007 |
| WO | 2007130515 A2 | 11/2007 |
| WO | 2008005055 A2 | 1/2008 |
| WO | 2008014841 A1 | 2/2008 |
| WO | 2008022147 A1 | 2/2008 |
| WO | 2008073143 A2 | 6/2008 |
| WO | 2008150451 A2 | 12/2008 |
| WO | 2008150451 A3 | 3/2009 |
| WO | 2009071463 A2 | 6/2009 |
| WO | 2009074203 A1 | 6/2009 |
| WO | 2009115805 A1 | 9/2009 |
| WO | 2010005453 A2 | 1/2010 |
| WO | 2011008464 A1 | 1/2011 |
| WO | 2011041184 A2 | 4/2011 |
| WO | 2011050359 A1 | 4/2011 |
| WO | 2010069488 A8 | 5/2011 |
| WO | 2011149996 A2 | 12/2011 |
| WO | 2012047274 A2 | 4/2012 |
| WO | 2012047274 A3 | 5/2012 |
| WO | 2012162526 A2 | 11/2012 |
| WO | 2013106771 A2 | 7/2013 |
| WO | 2013169462 A1 | 11/2013 |
| WO | 2013175204 A1 | 11/2013 |
| WO | 2013177433 A2 | 11/2013 |
| WO | 2013177461 A2 | 11/2013 |
| WO | 2014011646 A1 | 1/2014 |
| WO | 2014044387 A1 | 3/2014 |
| WO | 2014049445 A2 | 4/2014 |
| WO | 2014089479 A1 | 6/2014 |
| WO | 2013177433 A3 | 8/2014 |
| WO | 2014131435 A1 | 9/2014 |
| WO | 2014143880 A1 | 9/2014 |
| WO | 2015000061 A1 | 1/2015 |
| WO | 2015003193 A2 | 1/2015 |
| WO | 2015021177 A1 | 2/2015 |
| WO | 2015048295 A1 | 4/2015 |
| WO | 2015066693 A1 | 5/2015 |
| WO | 2015081122 A2 | 6/2015 |
| WO | 2015105911 A1 | 7/2015 |
| WO | 2015106023 A1 | 7/2015 |
| WO | 2015081122 A3 | 12/2015 |
| WO | 2016012371 A1 | 1/2016 |
| WO | 2016149507 A1 | 9/2016 |
| WO | 2016160563 A1 | 10/2016 |
| WO | 2016205411 A2 | 12/2016 |
| WO | 2016210006 A2 | 12/2016 |
| WO | 2016210006 A3 | 4/2017 |
| WO | 2017065947 A1 | 4/2017 |
| WO | 2016205411 A3 | 9/2017 |
| WO | 2017180910 A1 | 10/2017 |
| WO | 2018009356 A1 | 1/2018 |
| WO | 2018085820 A1 | 5/2018 |
| WO | 2018102601 A1 | 6/2018 |
| WO | 2018114900 A1 | 6/2018 |
| WO | 2018118105 A1 | 6/2018 |
| WO | 2019010498 A1 | 1/2019 |
| WO | 2019055220 A1 | 3/2019 |

OTHER PUBLICATIONS

Examination Report and Search Report dated Mar. 17, 2021 for AE Application No. P6001175/2017.

Duan, et al. Three-dimensional copper (II) metal-organic framework with open metal sites and anthracene nucleus for highly selective $C_2H_2/CH_4$ and $C_2NH_2/CO_2$ gas separation at room temperature. Microporous and Mesoporous Materials. vol. 181, Nov. 15, 2013, pp. 99-104.

He, et al. A microporus metal-organic framework for highly selective separation of acetylene, ethylene, and ethane from methane at room temperature. Chemistry. Jan. 9, 2012; 18(2):613-9. doi 10.1002/chem.201102734. Epub Dec. 8, 2011.

Office Action dated Mar. 15, 2019 for U.S. Appl. No. 15/690,090.

Notice of Allowance dated Oct. 3, 2019 for U.S. Appl. No. 15/690,090.

Notice of Allowance dated Jan. 27, 2020 for U.S. Appl. No. 15/690,090.

Notice of Allowance dated May 14, 2020 for U.S. Appl. No. 15/690,090.

Chemical Engineering—"Separation Processes: Supercritical CO2: a Green Solvent" Feb. 1, 2010.

Office Action dated Sep. 28, 2020 for QA Application No. QA/201709/00391.

(56) References Cited

OTHER PUBLICATIONS

Office Action dated Dec. 18, 2020 for SA Application No. 517382296.
Agarwal, et al., Aqueous Au—Pd colloids catalyze selective CH4 oxidation to CH3OH with O2 under mild conditions, Science 358, Oct. 13, 2017, 223-27.
Ahari, et al. Effects of operating parameters on oxidative coupling of methane over Na—WMn/SiO2 catalyst at elevated pressures. Journal of Natural Gas Chemistry. vol. 20, Issue 2, Mar. 2011, pp. 204-213.
American Petroleum Institute Publication 534 Heat Recovery Steam Generators Jan. 1995 (51 pages).
Autothermal Partial Oxidative Coupling of Methane. IP.com, Prior Art Database Technical Disclosure, Jul. 29, 2008, 5 pages.
Barrett, et al. The determination of pore volume and area distributions in porous substances—Computations from nitrogen isotherms. J. Am. Chem. Soc., 1951, vol. 73, pp. 373-380.
Berstad, D. et al. Low-temperature CO2 removal from natural gas. Energy Procedia (2012) 26:41-48.
Bloch, et al. Hydrocarbon Separations in a Metal-Organic Framework with Open Iron(II) Coordination Sites, Science, 2012, 335:1606-1610.
Bollmann, et al. Ethylene tetramerization: a new route to produce 1-octene in exceptionally high selectivities. J Am Chem Soc. Nov. 17, 2004;126(45):14712-3.
Bottella, et al. Effect of Potassium Doping on the Catalytic Behavior of Mo—V—Sb Mixed Oxide Catalysts in the Oxidation of Propane to Acrylic Acid. Catalysis Letters, Sep. 2003, vol. 89, Issue 3-4, pp. 249-253.
Carter, et al. High activity ethylene trimerisation catalysts based on diphosphine ligands. Chem Commun (Camb). Apr. 21, 2002;(8):858-9.
Caskey, et al., Dramatic Tuning of Carbon Dioxide Uptake via Metal Substitution in a Coordination Polymer with Cylindrical Pores, J. Am. Chern. Soc., (2009), 130(33): 10870-71.
Cavani, et al. Oxidative dehydrogenation of ethane and propane: How far from commercial implementation? Catalysis Today. 2007; 127(1-4):113-131.
Chemsystems PERP Report Ethylene Oxide/Ethylene Glycol 2005.
Chen, et al. M2 Forming—A Process for Aromatization of Light Hydrocarbons. Ind. Eng. Chem. Process. Des. Dev. 1986, 25, 151-155.
Choudhary, et al. Aromatization of dilute ethylene over Ga-modified ZSM-5 type zeolite catalysts. Microporous and Mesoporous Materials 47: 253-267, 2001.
Choudhary, et al. Oxidative conversion of methane/natural gas into higher hydrocarbons. Catalysis Surveys from Asia 8(1): 15-25, Feb. 2004.
Choudhary, et al. Surface Basicity and Acidity of Alkaline Earth-Promoted La2 03 Catalysts and Their Performance in Oxidative Coupling of Methane. Journal of Chemical Technology and Bio technology 72:125-130, 1998.
Christopher, et al. Engineering Selectivity in Heterogeneous Catalysis: Ag Nanowires as Selective Ethylene Epoxidation Catalysts. Journal of the American Chemical Society 130: 11264-11265, 2008.
Corma, From Microporous to Mesoporous Molecular Sieve Materials and Their Use in Catalysis, Chern. Rev., 97, 1997, pp. 2373-2419.
Debart, et al. α-MNO2 Nanowires: A catalyst for the O2 Electrode in Rechargeable Lithium Batteries. Angewandte Chemie International Edition 47: 4521-4524, 2008.
Dietzel, et al., Adsorption properties and structure of CO2 adsorbed on open coordination sites of metal-organic framework Ni2(dhtp) from gas adsorption, IR spectroscopy and X-ray diffraction, Chem. Commun. (2008), 5125-5127.
Ding, X et al. Effect of acid density of HZSM-5 on the oligomerization of ethylene in FCC dry gas. J Nat Gas Chem (2009) 18:156-160.

Enger, et al. A review of catalytic partial oxidation of methane to synthesis gas with emphasis on reaction mechanisms over transition metal catalysts. Applied Catalysis A: General 346 (1-2): 1-27, Aug. 2008.
Fallah, et al., A New Nano—(2Li2O/MgO) Catalyst/Porous Alpha-Alumina Composite for the Oxidative Coupling of Methane Reaction, AlIChE Journal, Mar. 2010, 56(3):717-28.
Gao, et al. A study on methanol steam reforming to CO2 and H2 over the La2 CO4 nanofiber catalyst. Journal of Solid State Chemistry 181: 7-13, 2008.
Gao, et al. The direct decomposition of NO over the La2 CuO4 nanofiber catalyst. Journal of Solid State Chemistry 181: 2804-2807, 2008.
Geier, et al., Selective adsorption of ethylene over ethane and propylene over propane in the metal-organic frameworks M2(dobdc) (M = Mg, Mn, Fe, Co, Ni, Zn), Chem. Sci., 2013, 4:2054-2061.
Ghosh, et al., Absorption of carbon dioxide into aqueous potassium carbonate promoted by boric acid, Energy Procedia, Feb. 2009, pp. 1075-1081.
Godini, et al. Techno-economic analysis of integrating the methane oxidative coupling and methane reforming processes. Fuel processing technology 2013 v 106 pp. 684-694.
Goto et al., Mesoporous Material from Zeolite, Journal of Poruous Materials, 2002, pp. 43-48.
Graves, C.R. Recycling CO2 into Sustainable Hydrocarbon Fuels: Electrolysis of CO2 and H2O. Dissertation, Columbia University (2010).
Guo, et al. Current Status and Some Perspectives of Rare Earth Catalytic Materials. Journal of The Chinese Rare Earth Society 25(1): 1-15, Feb. 2007.
Guo, X. et al. Direct, Nonoxidative Conversion of Methane to Ethylene, Aromatics, and Hydrogen. Science (2014) 344:616-619.
Gupta, M. Review on Heat Recovery Unit with Thermoelectric Generators. Intl J Eng and Innov Tech (IJEIT) (2014) 4 (4):128-131.
Haag, W.O. et al. Aromatics, Light Olefins and Gasoline from Methanol: Mechanistic Pathways with ZSM-5 Zeolite Catalyst. J Mol Catalysis (1982) 17:161-169.
Hosseinpour, Performance of CaX Zeolite for Separation of C2H6, C2H4, and CH4 by Adsorption Process; Capacity, Selectivity, and Dynamic Adsorption Measurements, Separation Science and Technology, 2011, 46:349-355.
Huang, et al. Exploiting shape effects of La2O3 nanocrystals for oxidative coupling of methane reaction. Nanoscale 5 (22): 10844-10848, 2013.
Huang, et al. Exploiting shape effects of La2O3 nanocrystals for oxidative coupling of methane reaction. Nanoscale—Electronic Supplementary Material, 2013, 7 pages.
Iwamoto, M. One step formation of propene from ethene or ethanol through metathesis on nickel ion-loaded silica. Molecules. Sep. 13, 2011;16(9):7844-63.
Kaibe, H. et al. Recovery of Plant Waste Heat by a Thermoelectric Generating System. Komatsu Tech Report (2011) 57(164):26-30.
Kaminsky, M.P. et al. Deactivation of Li-Based Catalysts for Methane Oxidative Coupling. Poster ACS Symposium on Natural Gas Upgrading II (Apr. 5-10, 1992).
Kaminsky, M.P. et al. Oxygen X-Ray Absorption Near-Edge Structure Characterization of the Ba-Doped Yttria Oxidative Coupling Catalyst. J Catalysis (1992) 136:16-23.
Keller, Gas-Adsorption Processes: State of the Art, American Chemical Society, 1983,pp. 145-169.
Keller, et al. Synthesis of Ethylene via Oxidative Coupling of Methane. Journal of Catalysis 73: 9-19, 1982.
Knuuttila, et al. Advanced Polyethylene Technologies—Controlled Material Properties. Long Term Properties of Polyolefins Advances in Polymer Science vol. 169, 2004, pp. 13-28.
Kuang, et al. Grafting of PEG onto lanthanum hydroxide nanowires. Materials Letters 62:4078-4080, 2008.
Labinger. Oxidative coupling of methane: an inherent limit to selectivity? Catal. Lett. 1988; 1:371-376.
Li, B. et al. Advances in CO2 capture technology: A patent review. Applied Energy (2013) 102:1439-1447.
Wikipedia search, Adiabatic Process, Mar. 2011, 10 pages.

(56) References Cited

OTHER PUBLICATIONS

Witek-Krowiak, A. et al. Carbon Dioxide Removal in a Membrane Contactor-Selection of Absorptive Liquid/Membrane System. Intl J Chem Eng and Appl. (2012) 3(6):391-395.
Wong, et al. Oxidative coupling of methane over alkali metal oxide promoted La2 O3/BaCO3 catalysts. J. Chem. Tech. Biotechnol. 65:351-354, 1996.
Wu, et al., High-Capacity Methane Storage in Metal-Organic Frameworks M2(dhtp): The Important Role of Open Metal Sites, J. Am. Chem. Soc. 131 (13):4995-5000, Mar. 10, 2009.
Xu, et al. Maximise ethylene gain and acetylene selective hydrogenation efficiency. Petroleum technology quarterly 18.3 (2013): 39-42.
Xu, G. et al. An Improved CO2 Separation and Purification System Based on Cryogenic Separation and Distillation Theory. Energies (2014) 7:3484-3502.
Yan, D. Modeling and Application of a Thermoelectric Generator. Thesis, Univ. Toronto (2011).
Yang, et al. Anistropic synthesis of boat shaped core shell Au—Ag nanocrystals and nanowires Nanotechnology 17: 2304-2310, 2006.
Yu, et al. Oxidative coupling of methane over acceptor-doped SrTi O3: Correlation between p-type conductivity and C2 selectivity and C2 yield. Journal of Catalysis. 13 (5): 338-344, 1992.
Zhang, Q. Journal of Natural Gas Chem., 12:81, 2003.
Zhao, et al. Technologies and catalysts for catalytic preparation of ethene. Industrial catalysis 12 (Supplement): 285-289, 2004.
Zhou, et al. Functionalization of lanthanum hydroxide nanowires by atom transfer radical polymerization. Nanotechnology 18, 2007, 7 pages.
Zhou. BP-UOP Cyclar Process. Handbook of Petroleum Refining Processes, The McGraw-Hill Companies (2004), pp. 2.29-2.38.
Zhou, et al., Enhanced H2 Adsorption in Isostructural Metal-Organic Frameworks with Open Metal Sites: Strong Dependence of the Binding Strength on Metal Ions, J. Am. Chem. Soc., 2008, 130(46): 15268-69.
Zimmerman, et al. Ethylene. Ulmann's Encyclopedia of Inudstrial Chemisty, Wiley-VCH Verlag GmbH & Co. KGaA, Weinheim, Germany, 2009, 66 pages.
U.S. Appl. No. 62/050,729, filed Sep. 15, 2014.
U.S. Appl. No. 62/073,478, filed Oct. 31, 2014.
International search report and written opinion dated Aug. 18, 2016 for PCT/US2016/022891.
Extended European search report and opinion dated Oct. 10, 2018 for EP Application No. 16765752.7.
Communication under Rule 71(3) EPC dated Feb. 20, 2020 for EP Application No. 16765752.7.
Office Action dated Nov. 4, 2019 for Chinese Patent Application No. 201680025279.6.
Pan, Sharp separation of C2/C3 hydrocarbon mixtures by zeolitic imidazolate framework-8 (ZIF-8) membranes synthesized in aqueous solutions. Chem Commun (Camb). Oct. 7, 2011;47(37):10275-7. doi: 10.1039/c1cc14051e. Epub Aug. 22, 2011.
Li, et al. Combined Single-Pass Conversion of Methane Via Oxidative Coupling and Dehydroaromatization. Catalysis Letters, Sep. 2003, vol. 89, Issue 3-4, pp. 275-279.
Li, et al. Energy and Fuels. 2008, 22: 1897-1901.
Ling, et al. Preparation of Ag core Au shell Nanowires and Their Surface Enhanced Raman Spectroscopic Studies. Acta Chimica Sinica. 65 (9): 779-784, 2007.
Liu, et al. A novel Na2 WO4-Mn.SiC monolithic foam catalyst with improved thermal properties for the oxidative coupling of methane. Catalysis Communications 9: 1302-1306, 2008.
Liu, et al. Increasing the Density of Adsorbed Hydrogen with Coordinatively Unsaturated Metal Centers in Metal-Organic Frameworks Langmuir, 2008, 24:4772-77 .
Lunsford, J.H. Catalytic conversion of methane to more useful chemicals and fuels: a challenge for the 21st century. Catalysis Today (2000) 63:165-174.
Lunsford. The Catalytic Oxidative Coupling of Methane. Angew. Chem Int. Ed. Engl. 1995; 34:970-980.
Lunsford, et al. The oxidative coupling of methane on chlorinated Lithium-doped magnesium oxide. J. Chem. Soc., Chem. Commun., 1991, 1430-1432.
Makal, et al., Methane storage in advanced porous materials, Critical Review, Chem. Soc. Rev., 2012, 41 :7761-7779.
Matherne, et al. Chapter 14, Direct Conversion of Methane to C2's and Liquid Fuels: Process Economics, Methane Conversion by Oxidative Processes (1992), 463-482.
Miltenburg, A.S. Adsorptive Separation of Light Olefin/Paraffin Mixtures: Dispersion of Zeolites. (2007) Ponsen & Looijen B.V., Wageningen, the Netherlands.
Mimoun, H. et al. Oxypyrolysis of Natural Gas. Appl Catalysis (1990) 58:269-280.
Mleczko, et al. Catalytic oxidative coupling of methane—reaction engineering aspects and process schemes. Fuel Processing Technology 42:217-248, 1995.
Mokhatab et al. "Handbook of Natural Gas Transmission and Processing: Principles and Practices" 2015. Chapter 7, pp. 237-242. (Year: 2015).
Morgan, C.R. et al. Gasoline from Alcohols. Ind Eng Chem Prod Res Dev(1981) 20:185-190.
Natural Gas Spec Sheet, 2003, prepared by Florida Power and Light Company.
Neltner, et al. Production of Hydrogen Using Nanocrystalline Protein-templated catalysts on M12 Phage. ACSNano 4(6):3227-3236, 2010.
Neltner. Hybrid Bio-templated Catalysts. Doctoral Thesis, Massachusetts Institute of Technology, Jun. 2010, 156 pages.
Nexant/Chemsystems HDPE Report, PERP 09/10-3, Jan. 2011.
Nghiem, XS. Ethylene Production by Oxidative Coupling of Methane: New Process Flow Diagram based on Adsorptive Separation. Berlin, Mar. 14, 2014.
Nielsen, et al. Treat LPGs with amines. Hydrocarbon Process 79 (1997): 49-59.
Nijem, et al. Tuning the gate opening pressure of Metal-Organic Frameworks (MOFs) for the selective separation of hydrocarbons. J Am Chem Soc. Sep. 19, 2012;134(37):15201-4. Epub Sep. 10, 2012.
Niu, et al. Preparation and characterization of La2 O3CO3 nanowires with high surface areas. Journal of the Chinese Rare Earth Society 23 (Spec. Issue): 33-36, Dec. 2005.
Ogura et al. Formation of Uniform Mesopores in ZSM-5 Zeolite through Treatment in Alkaline Solution, Chemistry Letters, 2000, pp. 882-883.
Ohashi, Y. et al. Development of Carbon Dioxide Removal System from the Flue Gas of Coal Fired Power Plant. Energy Procedia (2011) 4:29-34.
Oil Refinery—Wikipedia, The Free Encyclopedia Website. Jan. 2009.
Olah, G. Hydrocarbon Chemistry. 2nd Edition, John Wiley & Sons, 2003.
Olefins Conversion Technology, Website Accessed Aug. 28, 2014, http:www.CBI.com.
Pak, et al. Elementary Reactions in the Oxidative Coupling of Methane over Mn/NA2 WO4/SiO2 and MN/NA2 WO4/MgO Catalysts. Journal of Catalysis 179:222-230, 1998.
Process Systems; "Steam Tables" Apr. 8, 2017—https://web.archive.org/web/20170408152403/https://valvesonline.com.au/references/steamtables/.
Qiu, et al. Steady-state conversion of methane to aromatics in high yields using an integrated recycle reaction system. Catalysis Letters 48: 11-15, 1997.
Rousseau, Handbook of Separation Process Technology, 1987, p. 682.
Saito, et al. Dehydrogenation of Propane Over a Silica-Supported Gallium Oxide Catalyst. Catalysis Letters, Sep. 2003, vol. 89, Issue 3-4, pp. 213-217.
Schweer, et al. OCM in a fixed bed reactor: limits and perspectives. Catalysis Today, vol. 21, No. 2-3, Dec. 1, 1994, pp. 357-369.
Seeberger, A. et al. Gas Separation by Supported Ionic Liquid Membranes. DGMK-Conference, Hamburg, Germany (2007).
Simons, K. Membrane Technologies For CO2 Capture. Dissertation, U. of Twente (2010).

(56) References Cited

OTHER PUBLICATIONS

Smith, et al. Recent developments in solvent absorption technologies at the CO2CRC in Australia. Energy Procedia 1 (2009): 1549-1555.
Somorjai, et al. High technology catalysts towards 100% selectivity Fabrication, characterization and reaction studies. Catalysis today 100:201-215, 2005.
Sugiyama, et al. Redox Behaviors of Magnesium Vanadate Catalysts During the Oxidative Dehydrogenation of Propane Catalysis Letters, Sep. 2003, vol. 89, Issue 3-4, pp. 229-233.
Suzuki, K. Toshiba's Activity in Clean Coal and Carbon Capture Technology for Thermal Power Plants. APEC Clean Fossil Energy Technical and Policy Seminar (Feb. 22, 2012).
Tabak, S.A. et al. Conversion of Methanol over ZSM-5 to Fuels and Chemicals. Cat Today (1990) 307-327.
Takanabe, et al. Mechanistic Aspects and Reaction Pathways for Oxidative Coupling of Methane on Mn/NA2 WO4/SiO2 Catalysts. Journal of Physical Chemistry C 113(23):10131-10145, 2009.
Takanabe, et al. Rate and Selectivity Enhancements Mediated by OH Radicals in the Oxidative coupling of Methane Catalyzed by Mn/NA2 WO4/SiO2 . Angewandte Chemie International Edition 47:7689-7693, 2008.
Tong, et al. Development strategy research of downstream products of ethene in Tianjin. Tianjin Economy, pp. 37-40,1996.
Trautmann, et al. Cryogenic technology for nitrogen rejection from variable content natural gas. Presented at the XIV Convencion Internacional de Gas, Caracas, Venezuela, May 10-12, 2000, 13 pages.
Wang, et al. Autothermal oxidative coupling of methane on the SrCO3/Sm2 O3 catalysts. Catalysis communications 10: 807-810, 2009.
Wang, et al. Comparative study on oxidation of methane to ethane and ethylene over NA2 WO4-Mn/SiO2 catalysts prepared by different methods. Journal of Molecular Catalysis A: Chemical 245:272-277, 2006.
Wang, et al. Low temperature selective oxidation of methane to ethane and ethylene over BaCO3/La2 O3 catalysts prepared by urea combustion method. Catalysis communications 7: 5963, 2006.
Wang, et al., Critical Influence of BaCO3 on Low Temperature Catalytic Activity of BaCO3/ZrO2 Catalysts for Oxidative Coupling of Methane, Catalysis Letters (2009), 129:156-162.
Water Electrolysis & Renewable Energy Systems. FuelCellToday (May 2013).
Examination Report dated Dec. 15, 2021 for SA Application No. 521421462.
Examination Report dated Dec. 15, 2021 for SA Application No. 521421463.
Communication dated Jan. 31, 2022 for EP Application No. 20199359.9.

\* cited by examiner

OXIDATIVE COUPLING OF METHANE METHODS AND SYSTEMS

CROSS-REFERENCE TO RELATED APPLICATIONS

This application is a continuation of U.S. patent application Ser. No. 15/690,090, filed Aug. 29, 2017, which is a continuation of International Patent Application No. PCT/US2016/022891, filed Mar. 17, 2016, which claims the benefit of U.S. Provisional Patent Application No. 62/141,177, filed Mar. 31, 2015, U.S. Provisional Patent Application No. 62/190,182, filed Jul. 8, 2015, U.S. Provisional Patent Application No. 62/195,237, filed Jul. 21, 2015, and U.S. Provisional Patent Application No. 62/300,287, filed Feb. 26, 2016; and International Patent Application No. PCT/US2016/022891, filed Mar. 17, 2016, is a continuation-in-part of U.S. patent application Ser. No. 14/789,953, filed Jul. 1, 2015, now U.S. Pat. No. 9,334,204, which claims the benefit of U.S. Provisional Patent Application No. 62/134,508, filed Mar. 17, 2015, and U.S. Provisional Patent Application No. 62/152,706, filed Apr. 24, 2015, all of which are incorporated herein by reference in their entireties.

BACKGROUND

There exists an infrastructure for chemical production throughout the world. This infrastructure is deployed on virtually every continent, addresses wide ranging industries, and employs a wide variety of different implementations of similar or widely differing technologies.

SUMMARY

The present disclosure provides systems and methods for reacting methane in an oxidative coupling of methane ("OCM") process to yield products comprising hydrocarbon compounds with two or more carbon atoms (also "$C_{2+}$ compounds" herein). OCM systems and methods of the disclosure can be integrated with various chemical processes, such as methanol (MeOH) production, chlorine ($Cl_2$) and sodium hydroxide (NaOH) production (e.g., chloralkali process), vinylchloride monomer (VCM) production, ammonia ($NH_3$) production, processes having syngas (e.g., mixtures of hydrogen ($H_2$) and carbon monoxide (CO) in any proportion), or olefin derivative production.

An aspect of the present disclosure provides a method for oxidative coupling of methane (OCM) to generate hydrocarbon compounds containing at least two carbon atoms (C2+ compounds), comprising: (a) injecting oxygen ($O_2$), methane ($CH_4$) and ethane ($C_2H_6$) into an OCM reactor, wherein the OCM reactor comprises an OCM catalyst for facilitating an OCM reaction, and wherein the $C_2H_6$ has a concentration of at least about 3 mol % within the OCM catalyst bed; and (b) with the aid of the OCM catalyst in the OCM reactor, performing an OCM reaction to convert the $CH_4$ into C2+ compounds as part of a product stream.

In some embodiments of aspects provided herein, the $C_2H_6$ has a concentration of at least about 3 mol % at an inlet of the OCM catalyst bed. In some embodiments of aspects provided herein, at least a portion of the $C_2H_6$ is injected into the OCM reactor separately from the $CH_4$. In some embodiments of aspects provided herein, the method further comprises increasing or decreasing an amount of $CH_4$ injected in (a) to maintain the concentration of $C_2H_6$ within +/−0.2 mol % during the injecting. In some aspects of aspects provided herein, the product stream comprises ethane. In some embodiments of aspects provided herein, the method further comprises recycling at least a portion of the ethane in the product stream to the OCM reactor.

An aspect of the present disclosure provides an oxidative coupling of methane (OCM) system for generating hydrocarbon compounds containing at least two carbon atoms ($C_{2+}$ compounds), comprising: an OCM reactor that (i) receives oxygen ($O_2$), methane ($CH_4$) and ethane ($C_2H_6$), wherein the $C_2H_6$ has a concentration of at least about 3 mol % at an inlet of the OCM reactor, and (ii) reacts the $CH_4$ and $O_2$ to yield a product stream comprising the $C_{2+}$ compounds.

In some embodiments of aspects provided herein, at least a portion of the $C_2H_6$ is injected into the OCM reactor separately from the $CH_4$. In some embodiments of aspects provided herein, the system further comprises a control system that increases or decreases an amount of $CH_4$ received by the OCM reactor to maintain the concentration of $C_2H_6$ within +/−0.2 mol % during the receiving. In some embodiments of aspects provided herein, the product stream further comprises ethane. In some embodiments of aspects provided herein, at least a portion of the ethane in the product stream is recycled to the OCM reactor.

An aspect of the present disclosure provides a method for oxidative coupling of methane (OCM) to generate hydrocarbon compounds containing at least two carbon atoms ($C_{2+}$ compounds), comprising: (a) injecting oxygen ($O_2$), methane ($CH_4$) and ethane ($C_2H_6$) into an OCM reactor, wherein the $C_2H_6$ has a concentration of at least about 3 mol %; and (b) with the aid of an OCM catalyst in the OCM reactor, performing an OCM reaction to convert the $CH_4$ into $C_{2+}$ compounds as part of a product stream.

In some embodiments of aspects provided herein, at least some of the $C_2H_6$ is injected into the OCM reactor separately from the $CH_4$. In some embodiments of aspects provided herein, the method further comprises increasing or decreasing an amount of $CH_4$ injected in (a) to maintain the concentration of $C_2H_6$ within +/−0.2 mol % during the injecting. In some embodiments of aspects provided herein, the product stream comprises ethane, and wherein at least a portion of the ethane in the product stream is recycled to the OCM reactor.

An aspect of the present disclosure provides a method for producing methanol (MeOH) and hydrocarbon compounds containing at least two carbon atoms ($C_{2+}$ compounds), comprising: (a) directing methane ($CH_4$) and oxygen ($O_2$) into an oxidative coupling of methane (OCM) reactor to produce a product stream comprising the $C_{2+}$ compounds, carbon monoxide (CO) and/or carbon dioxide ($CO_2$), and un-reacted $CH_4$; (b) enriching the CO and/or $CO_2$ from the product stream to generate an enriched CO and/or $CO_2$ stream; (c) directing the enriched CO and/or $CO_2$ stream to an MeOH reactor to produce MeOH; (d) enriching the un-reacted $CH_4$ from the product stream to produce an enriched $CH_4$ stream; and (e) directing at least a portion of the enriched $CH_4$ stream to a steam methane reformer (SMR) that produces hydrogen ($H_2$) and CO and/or $CO_2$.

In some embodiments of aspects provided herein, the method further comprises directing CO and/or $CO_2$ produced in the SMR to the MeOH reactor. In some embodiments of aspects provided herein, all of the CO and/or $CO_2$ from the product stream and all of the CO and/or $CO_2$ from the SMR is converted to MeOH in the MeOH reactor. In some embodiments of aspects provided herein, the un-reacted $CH_4$ is provided as fuel to the SMR. In some embodiments of aspects provided herein, the un-reacted $CH_4$ is provided as feedstock to the SMR, and wherein the SMR converts the un-reacted $CH_4$ into the $H_2$ and the at least one of CO and $CO_2$ for conversion to MeOH in the MeOH reactor. In some embodiments of aspects provided herein, at least about 95% of the methane is converted into MeOH or $C_{2+}$ products. In some embodiments of aspects provided herein, the method further comprises providing the $C_{2+}$ compounds to a cracker that cracks or refines the $C_{2+}$ compounds. In some embodiments of aspects provided herein, at least 80% of the methane consumed by the SMR is from the enriched $CH_4$ stream. In some embodiments of aspects provided herein, the method further comprises directing a portion of the enriched $CH_4$ stream to a cracker. In some embodiments of aspects provided herein, at least 80% of the methane consumed by the SMR and the cracker is from the enriched $CH_4$ stream. In some embodiments of aspects provided herein, the method further comprises directing at least a portion of the enriched $CH_4$ stream to a methane-consuming process. In some embodiments of aspects provided herein, at least 80% of the methane consumed by the SMR, the cracker and the methane-consuming process is from the enriched $CH_4$ stream. In some embodiments of aspects provided herein, the product stream comprises CO. In some embodiments of aspects provided herein, the product stream comprises $CO_2$. In some embodiments of aspects provided herein, the product stream comprises CO and $CO_2$.

An aspect of the present disclosure provides a system for producing methanol (MeOH) and hydrocarbon compounds containing at least two carbon atoms ($C_{2+}$ compounds), comprising: an oxidative coupling of methane (OCM) reactor that (i) receives methane ($CH_4$) and oxygen ($O_2$) and (ii) reacts the $CH_4$ and $O_2$ to yield a product stream comprising the $C_{2+}$ compounds, carbon monoxide (CO) and/or carbon dioxide ($CO_2$), and un-reacted $CH_4$; an MeOH reactor that (i) receives CO and/or $CO_2$ enriched from the product stream and (ii) reacts the CO and/or $CO_2$ to produce MeOH; and a steam methane reformer (SMR) that (i) receives un-reacted $CH_4$ enriched from the product stream and (ii) provides hydrogen ($H_2$) and at least one of carbon monoxide (CO) and $CO_2$ to the MeOH reactor to produce MeOH.

In some embodiments of aspects provided herein, the system further comprises a separation unit downstream of the OCM reactor and upstream of the MeOH reactor, wherein the separation unit enriches the CO and/or $CO_2$ from the product stream. In some embodiments of aspects provided herein, the system further comprises a separation unit downstream of the OCM reactor and upstream of the SMR, wherein the separation unit enriches the un-reacted $CH_4$ from the product stream. In some embodiments of aspects provided herein, the SMR uses the un-reacted $CH_4$ as fuel. In some embodiments of aspects provided herein, the SMR uses the un-reacted $CH_4$ as a feedstock and converts the un-reacted $CH_4$ into the $H_2$ and the at least one of CO and $CO_2$ for conversion to MeOH in the MeOH reactor. In some embodiments of aspects provided herein, the MeOH reactor converts all of the $CO_2$ from the product stream and all of the $CO_2$ from the SMR to MeOH. In some embodiments of aspects provided herein, at least about 95% of the methane is converted into MeOH or $C_{2+}$ products. In some embodiments of aspects provided herein, the system further comprises a cracker that (i) receives the $C_{2+}$ compounds and (ii) cracks or refines the $C_{2+}$ compounds. In some embodiments of aspects provided herein, the un-reacted $CH_4$ directed to the SMR provides at least 80% of the methane consumed by the SMR. In some embodiments of aspects provided herein, the system further comprises a cracker that receives at least a portion of the unreacted $CH_4$. In some embodiments of aspects provided herein, at least 80% of the methane consumed by the SMR and the cracker is from the unreacted $CH_4$. In some embodiments of aspects provided herein, the system further comprises a methane-consuming module that receives the enriched $CH_4$. In some embodiments of aspects provided herein, at least 80% of the methane consumed by the SMR, the cracker and the methane-consuming module is from the unreacted $CH_4$. In some embodiments of aspects provided herein, the product stream comprises CO. In some embodiments of aspects provided herein, the product stream comprises $CO_2$. In some embodiments of aspects provided herein, the product stream comprises CO and $CO_2$.

An aspect of the present disclosure provides a method for producing methanol (MeOH) and hydrocarbon compounds containing at least two carbon atoms ($C_{2+}$ compounds), comprising: (a) directing methane ($CH_4$) and oxygen ($O_2$) into an oxidative coupling of methane (OCM) reactor to produce a product stream comprising the $C_{2+}$ compounds, carbon monoxide (CO) and/or carbon dioxide ($CO_2$), and un-reacted $CH_4$; (b) enriching the CO and/or $CO_2$ from the product stream to generate an enriched CO and/or $CO_2$ stream; and (c) directing the enriched CO and/or $CO_2$ stream to an MeOH reactor to produce MeOH.

In some embodiments of aspects provided herein, all of the CO and/or $CO_2$ from the product stream is converted to MeOH in the MeOH reactor. In some embodiments of aspects provided herein, at least about 95% of the methane is converted into MeOH or $C_{2+}$ products. In some embodiments of aspects provided herein, the method further comprises providing the $C_{2+}$ compounds to a cracker that cracks or refines the $C_{2+}$ compounds. In some embodiments of aspects provided herein, the product stream comprises CO. In some embodiments of aspects provided herein, the product stream comprises $CO_2$. In some embodiments of aspects provided herein, the product stream comprises CO and $CO_2$.

An aspect of the present disclosure provides a system for producing methanol (MeOH) and hydrocarbon compounds containing at least two carbon atoms ($C_{2+}$ compounds), comprising: an oxidative coupling of methane (OCM) reactor that (i) receives methane ($CH_4$) and oxygen ($O_2$) and (ii) reacts the $CH_4$ and $O_2$ to yield a product stream comprising the $C_{2+}$ compounds, carbon monoxide (CO) and/or carbon dioxide ($CO_2$), and un-reacted $CH_4$; an MeOH reactor that (i) receives CO and/or $CO_2$ enriched from the product stream and (ii) reacts the CO and/or $CO_2$ to produce MeOH.

In some embodiments of aspects provided herein, the MeOH reactor converts all of the $CO_2$ from the product stream to MeOH. In some embodiments of aspects provided herein, the system further comprises a separation unit downstream of the OCM reactor and upstream of the MeOH reactor, wherein the separation unit enriches the CO and/or $CO_2$ from the product stream. In some embodiments of aspects provided herein, at least about 95% of the methane is converted into MeOH or $C_{2+}$ products. In some embodiments of aspects provided herein, the system further comprises a cracker that (i) receives the $C_{2+}$ compounds and (ii) cracks or refines the $C_{2+}$ compounds. In some embodiments of aspects provided herein, the system further comprises a cracker that receives at least a portion of the unreacted $CH_4$. In some embodiments of aspects provided herein, the product stream comprises CO. In some embodiments of aspects provided herein, the product stream comprises $CO_2$. In some embodiments of aspects provided herein, the product stream comprises CO and $CO_2$.

An aspect of the present disclosure provides a method for producing methanol (MeOH) and hydrocarbon compounds containing at least two carbon atoms ($C_{2+}$ compounds), comprising: (a) directing methane ($CH_4$) and oxygen ($O_2$) into an oxidative coupling of methane (OCM) reactor to produce a product stream comprising the $C_{2+}$ compounds and un-reacted $CH_4$; (b) enriching the un-reacted $CH_4$ from the product stream to produce an enriched $CH_4$ stream; (c) directing at least a portion of the enriched $CH_4$ stream to a steam methane reformer (SMR) that produces hydrogen ($H_2$) and CO and/or $CO_2$; and (d) directing the CO and/or $CO_2$ to an MeOH reactor to produce MeOH.

In some embodiments of aspects provided herein, all of the CO and/or $CO_2$ from the SMR is converted to MeOH in the MeOH reactor. In some embodiments of aspects provided herein, the un-reacted $CH_4$ is provided as fuel to the SMR. In some embodiments of aspects provided herein, the un-reacted $CH_4$ is provided as feedstock to the SMR, and wherein the SMR converts the un-reacted $CH_4$ into the $H_2$ and the at least one of CO and $CO_2$ for conversion to MeOH in the MeOH reactor. In some embodiments of aspects provided herein, at least about 95% of the methane is converted into MeOH or $C_{2+}$ products. In some embodiments of aspects provided herein, the method further comprises providing the $C_{2+}$ compounds to a cracker that cracks or refines the $C_{2+}$ compounds. In some embodiments of aspects provided herein, at least 80% of the methane consumed by the SMR is from the enriched $CH_4$ stream. In some embodiments of aspects provided herein, the method further comprises directing a portion of the enriched $CH_4$ stream to a cracker. In some embodiments of aspects provided herein, at least 80% of the methane consumed by the SMR and the cracker is from the enriched $CH_4$ stream. In some embodiments of aspects provided herein, the method further comprises directing at least a portion of the enriched $CH_4$ stream to a methane-consuming process. In some embodiments of aspects provided herein, at least 80% of the methane consumed by the SMR, the cracker and the methane-consuming process is from the enriched $CH_4$ stream. In some embodiments of aspects provided herein, the product stream comprises CO. In some embodiments of aspects provided herein, the product stream comprises $CO_2$. In some embodiments of aspects provided herein, the product stream comprises CO and $CO_2$.

An aspect of the present disclosure provides a system for producing methanol (MeOH) and hydrocarbon compounds containing at least two carbon atoms ($C_{2+}$ compounds), comprising: an oxidative coupling of methane (OCM) reactor that (i) receives methane ($CH_4$) and oxygen ($O_2$) and (ii) reacts the $CH_4$ and $O_2$ to yield a product stream comprising the $C_{2+}$ compounds and un-reacted $CH_4$; a steam methane reformer (SMR) that (i) receives un-reacted $CH_4$ enriched from the product stream and (ii) provides hydrogen ($H_2$) and carbon monoxide (CO) and/or $CO_2$; and an MeOH reactor that (i) receives the CO and/or $CO_2$ and (ii) reacts the CO and/or $CO_2$ to produce MeOH.

In some embodiments of aspects provided herein, the system further comprises a separation unit downstream of the OCM reactor and upstream of the SMR, wherein the separation unit enriches the un-reacted $CH_4$ from the product stream. In some embodiments of aspects provided herein, the SMR uses the un-reacted $CH_4$ as fuel. In some embodiments of aspects provided herein, the SMR uses the un-reacted $CH_4$ as a feedstock and converts the un-reacted $CH_4$ into the $H_2$ and the CO and/or $CO_2$ for conversion to MeOH in the MeOH reactor. In some embodiments of aspects provided herein, the MeOH reactor converts all of the $CO_2$ from the product stream and all of the $CO_2$ from the SMR to MeOH. In some embodiments of aspects provided herein, at least about 95% of the methane is converted into MeOH or $C_{2+}$ products. In some embodiments of aspects provided herein, the system further comprises a cracker that (i) receives the $C_{2+}$ compounds and (ii) cracks or refines the $C_{2+}$ compounds. In some embodiments of aspects provided herein, the un-reacted $CH_4$ directed to the SMR provides at least 80% of the methane consumed by the SMR. In some embodiments of aspects provided herein, the system further comprises a cracker that receives at least a portion of the unreacted $CH_4$. In some embodiments of aspects provided herein, at least 80% of the methane consumed by the SMR and the cracker is from the unreacted $CH_4$. In some embodiments of aspects provided herein, the system further comprises a methane-consuming module that receives the enriched $CH_4$. In some embodiments of aspects provided herein, at least 80% of the methane consumed by the SMR, the cracker and the methane-consuming module is from the unreacted $CH_4$. In some embodiments of aspects provided herein, the product stream comprises CO. In some embodiments of aspects provided herein, the product stream comprises $CO_2$. In some embodiments of aspects provided herein, the product stream comprises CO and $CO_2$.

An aspect of the present disclosure provides a method for producing methanol (MeOH) and hydrocarbon compounds containing at least two carbon atoms ($C_{2+}$ compounds), comprising: (a) directing methane ($CH_4$) and oxygen ($O_2$) into an oxidative coupling of methane (OCM) reactor to produce a product stream comprising the $C_{2+}$ compounds, carbon monoxide (CO) and/or carbon dioxide ($CO_2$), and un-reacted $CH_4$; (b) enriching the CO and/or $CO_2$ from the product stream to generate an enriched CO and/or $CO_2$ stream that is directed to an MeOH reactor to produce MeOH; and (c) enriching the un-reacted $CH_4$ from the product stream to produce an enriched $CH_4$ stream that is directed to a steam methane reformer (SMR), which SMR provides hydrogen ($H_2$) and at least one of carbon monoxide (CO) and $CO_2$ to the MeOH reactor to produce MeOH.

In some embodiments of aspects provided herein, the un-reacted $CH_4$ is provided as fuel to the SMR. In some embodiments of aspects provided herein, the un-reacted $CH_4$ is provided as feedstock to the SMR, and wherein the SMR converts the un-reacted $CH_4$ into the $H_2$ and the at least one of CO and $CO_2$ for conversion to MeOH in the MeOH reactor. In some embodiments of aspects provided herein, all of the $CO_2$ from the product stream and all of the $CO_2$ from the SMR is converted to MeOH in the MeOH reactor. In some embodiments of aspects provided herein, at least about 95% of the methane is converted into MeOH or $C_{2+}$ products. In some embodiments of aspects provided herein, the method further comprises providing the $C_{2+}$ compounds to a cracker that cracks or refines the $C_{2+}$ compounds. In some embodiments of aspects provided herein, the un-reacted $CH_4$ directed to the SMR provides at least 80% of the methane consumed by the SMR. In some embodiments of aspects provided herein, the method further comprises directing the $CH_4$ enriched in (c) to a cracker. In some embodiments of aspects provided herein, the un-reacted $CH_4$ directed to the SMR and the cracker provides at least 80% of the methane consumed by the SMR and the cracker. In some embodiments of aspects provided herein, the method further comprises directing the enriched $CH_4$ to a methane-consuming process. In some embodiments of aspects provided herein, the un-reacted $CH_4$ directed to the SMR, the cracker and the methane-consuming process provides at least 80% of the methane consumed by the SMR, the cracker and the methane-consuming process.

An aspect of the present disclosure provides a system for producing methanol (MeOH) and hydrocarbon compounds containing at least two carbon atoms ($C_{2+}$ compounds), comprising: an oxidative coupling of methane (OCM) reactor that (i) receives methane ($CH_4$) and oxygen ($O_2$) and (ii) reacts the $CH_4$ and $O_2$ to yield a product stream comprising the $C_{2+}$ compounds, carbon monoxide (CO) and/or carbon dioxide ($CO_2$), and un-reacted $CH_4$; an MeOH reactor that (i) receives CO and/or $CO_2$ enriched from the product stream and (ii) reacts the CO and/or $CO_2$ to produce MeOH; and a steam methane reformer (SMR) that (i) receives un-reacted $CH_4$ enriched from the product stream and (ii) provides hydrogen ($H_2$) and at least one of carbon monoxide (CO) and $CO_2$ to the MeOH reactor to produce MeOH.

In some embodiments of aspects provided herein, the system further comprises a separation unit downstream of the OCM reactor and upstream of the MeOH reactor, wherein the separation unit enriches the CO and/or $CO_2$ from the product stream. In some embodiments of aspects provided herein, the system further comprises a separation unit downstream of the OCM reactor and upstream of the SMR, wherein the separation unit enriches the un-reacted $CH_4$ from the product stream. In some embodiments of aspects provided herein, the SMR uses the un-reacted $CH_4$ as fuel. In some embodiments of aspects provided herein, the SMR uses the un-reacted $CH_4$ as a feedstock and converts the un-reacted $CH_4$ into the $H_2$ and the at least one of CO and $CO_2$ for conversion to MeOH in the MeOH reactor. In some embodiments of aspects provided herein, the MeOH reactor converts all of the $CO_2$ from the product stream and all of the $CO_2$ from the SMR to MeOH. In some embodiments of aspects provided herein, at least about 95% of the methane is converted into MeOH or $C_{2+}$ products. In some embodiments of aspects provided herein, the system further comprises a cracker that (i) receives the $C_{2+}$ compounds and (ii) cracks or refines the $C_{2+}$ compounds. In some embodiments of aspects provided herein, the un-reacted $CH_4$ directed to the SMR provides at least 80% of the methane consumed by the SMR. In some embodiments of aspects provided herein, the system further comprises a cracker that receives at least a portion of the $CH_4$ enriched in (c). In some embodiments of aspects provided herein, the un-reacted $CH_4$ directed to the SMR and the cracker provides at least 80% of the methane consumed by the SMR and the cracker. In some embodiments of aspects provided herein, the system further comprises a methane-consuming module that receives the enriched $CH_4$. In some embodiments of aspects provided herein, the un-reacted $CH_4$ directed to the SMR, the cracker and the methane-consuming module provides at least 80% of the methane consumed by the SMR, the cracker and the methane-consuming module.

An aspect of the present disclosure provides a method for producing chlorine ($Cl_2$), sodium hydroxide (NaOH) and compounds containing at least two carbon atoms ($C_{2+}$ compounds), comprising: (a) directing sodium chloride (NaCl) and water ($H_2O$) into a chloralkali module that produces chlorine ($Cl_2$), NaOH and hydrogen ($H_2$) from the NaCl and $H_2O$; (b) directing at least a portion of the $H_2$ produced in (a) to a methanation module that reacts the $H_2$ and CO and/or $CO_2$ to produce $CH_4$; and (c) directing at least a portion of the $CH_4$ produced in (b) to an OCM module, which OCM module reacts the $CH_4$ and $O_2$ in an OCM process to yield the $C_{2+}$ compounds and heat.

In some embodiments of aspects provided herein, the OCM module includes an OCM reactor with an OCM catalyst that generates the $C_{2+}$ compounds. In some embodiments of aspects provided herein, the OCM module uses the heat to generate electrical power. In some embodiments of aspects provided herein, the OCM module includes a turbine for generating the electrical power. In some embodiments of aspects provided herein, the method further comprises using the electrical power generated by the OCM module to electrochemically generate the $Cl_2$, NaOH and $H_2$ from the NaCl and $H_2O$. In some embodiments of aspects provided herein, at least 80% of electrical power consumed by the chloralkali module is produced by the OCM module. In some embodiments of aspects provided herein, at least a portion of the CO and/or $CO_2$ is produced in the OCM process in the OCM module. In some embodiments of aspects provided herein, the method further comprises directing at least a portion of the $Cl_2$ produced by the chloralkali module and at least a portion of the $C_{2+}$ compounds produced by the OCM module into an additional module that reacts the at least the portion of the $Cl_2$ with the at least the portion of the $C_{2+}$ compounds to produce vinyl chloride monomer (VCM) and/or ethylene dichloride (EDC). In some embodiments of aspects provided herein, the $C_{2+}$ compounds comprise less than about 99% ethylene when reacted by the additional module.

An aspect of the present disclosure provides a system for producing chlorine ($Cl_2$), sodium hydroxide (NaOH) and compounds containing at least two carbon atoms ($C_{2+}$ compounds), comprising: a chloralkali module that (i) accepts sodium chloride (NaCl) and water ($H_2O$) and (ii) generates chlorine ($Cl_2$), NaOH and hydrogen ($H_2$) from the NaCl and $H_2O$; a methanation module in fluid communication with the chloralkali module, wherein the methanation module (i) accepts the $H_2$ from the chloralkali module and carbon monoxide (CO) and/or carbon dioxide ($CO_2$) and (ii) reacts the $H_2$ and the CO and/or $CO_2$ to produce methane ($CH_4$); and an oxidative coupling of methane (OCM) module in fluid communication with the methanation module, wherein the OCM module (i) accepts the $CH_4$ from the methanation module and oxygen ($O_2$) and (ii) reacts the $CH_4$ and the $O_2$ in an OCM process to yield the $C_{2+}$ compounds and heat.

In some embodiments of aspects provided herein, the OCM module includes an OCM reactor with an OCM catalyst that generates the $C_{2+}$ compounds. In some embodiments of aspects provided herein, the OCM module uses the heat to generate electrical power. In some embodiments of aspects provided herein, the OCM module includes a turbine for generating the electrical power. In some embodiments of aspects provided herein, the chloralkali module uses the electrical power generated by the OCM module to electrochemically generate the $Cl_2$, NaOH and $H_2$ from the NaCl and $H_2O$. In some embodiments of aspects provided herein, at least 80% of electrical power consumed by the chloralkali module is produced by the OCM module. In some embodiments of aspects provided herein, at least a portion of the CO and/or $CO_2$ in reacted by the methanation module is produced by the OCM module. In some embodiments of aspects provided herein, the system further comprises an additional module in fluid communication with the OCM module and the chloralkali module, wherein the additional module reacts at least a portion of the $Cl_2$ produced by the chloralkali module with at least a portion of the $C_{2+}$ compounds produced by the OCM module to produce vinyl chloride monomer (VCM) and ethylene dichloride (EDC). In some embodiments of aspects provided herein, the $C_{2+}$ compounds comprise less than about 99% ethylene when reacted by the additional module.

An aspect of the present disclosure provides a method for producing chlorine ($Cl_2$), sodium hydroxide (NaOH) and compounds containing at least two carbon atoms ($C_{2+}$ compounds), comprising: (a) directing methane ($CH_4$) and oxygen ($O_2$) into an oxidative coupling of methane (OCM) module that (i) reacts the $CH_4$ and $O_2$ in an OCM process to yield the $C_{2+}$ compounds and heat, and (ii) uses the heat to generate electrical power; (b) directing hydrogen ($H_2$) and carbon monoxide (CO) and/or carbon dioxide ($CO_2$) into a methanation module that (i) reacts the $H_2$ and CO and/or $CO_2$ to produce $CH_4$, and (ii) directs at least a portion of the $CH_4$ produced in the methanation module to the OCM module; and (c) directing NaCl and $H_2O$ into a chloralkali module that (i) uses the electrical power produced by the OCM module to electrochemically generate $Cl_2$, NaOH and $H_2$ from the NaCl and $H_2O$, and (ii) direct at least a portion of the $H_2$ to the methanation module.

In some embodiments of aspects provided herein, the OCM module includes an OCM reactor with an OCM catalyst that generates the $C_{2+}$ compounds. In some embodiments of aspects provided herein, the OCM module includes a turbine for generating the electrical power. In some embodiments of aspects provided herein, at least 80% of electrical power consumed by the chloralkali module is produced by the OCM module. In some embodiments of aspects provided herein, at least a portion of the $CO_2$ or the CO in reacted by the methanation module is produced by the OCM module. In some embodiments of aspects provided herein, the method further comprises directing at least a portion of the $Cl_2$ produced by the chloralkali module and at least a portion of the $C_{2+}$ compounds produced by the OCM module into an additional module that reacts the at least a portion of the $Cl_2$ with the at least a portion of the $C_{2+}$ compounds to produce vinyl chloride monomer (VCM) and ethylene dichloride (EDC). In some embodiments of aspects provided herein, the $C_{2+}$ compounds comprise less than about 99% ethylene when reacted by the additional module.

An aspect of the present disclosure provides a system for producing chlorine ($Cl_2$), sodium hydroxide (NaOH) and compounds containing at least two carbon atoms ($C_{2+}$ compounds), comprising: an oxidative coupling of methane (OCM) module that (i) accepts methane ($CH_4$) and oxygen ($O_2$) and reacts the $CH_4$ and $O_2$ in an OCM process that yields the $C_{2+}$ compounds and heat, and (ii) uses the heat to generate electrical power; a methanation module in fluid communication with the OCM module, wherein the methanation module (i) accepts hydrogen ($H_2$) and carbon monoxide (CO) and/or carbon dioxide ($CO_2$), (ii) reacts the $H_2$ and CO and/or $CO_2$ to produce $CH_4$, and (iii) directs at least a portion of the $CH_4$ produced in the methanation module to the OCM module; and a chloralkali module in fluid communication with the methanation module, wherein the chloralkali module (i) accepts NaCl and $H_2O$, (ii) uses the electrical power produced by the OCM module to electrochemically generate $Cl_2$, NaOH and $H_2$ from the NaCl and $H_2O$, and (iii) directs at least a portion of the $H_2$ to the methanation module.

In some embodiments of aspects provided herein, the OCM module includes an OCM reactor with an OCM catalyst that generates the $C_{2+}$ compounds. In some embodiments of aspects provided herein, the OCM module includes a turbine for generating the electrical power. In some embodiments of aspects provided herein, at least 80% of electrical power consumed by the chloralkali module is produced by the OCM module. In some embodiments of aspects provided herein, at least a portion of the $CO_2$ or the CO in reacted by the methanation module is produced by the OCM module. In some embodiments of aspects provided herein, the system further comprises an additional module in fluid communication with the OCM module and the chloralkali module, wherein the additional module reacts at least a portion of the $Cl_2$ produced by the chloralkali module with at least a portion of the $C_{2+}$ compounds produced by the OCM module to produce vinyl chloride monomer (VCM) and ethylene dichloride (EDC). In some embodiments of aspects provided herein, the $C_{2+}$ compounds comprise less than about 99% ethylene when reacted by the additional module.

An aspect of the present disclosure provides a method for producing ammonia ($NH_3$) and hydrocarbon compounds containing at least two carbon atoms ($C_{2+}$ compounds), comprising: (a) directing methane ($CH_4$) and oxygen ($O_2$) into an oxidative coupling of methane (OCM) reactor that reacts the $CH_4$ and the $O_2$ in an OCM process to yield an OCM product stream comprising the $C_{2+}$ compounds, hydrogen ($H_2$), and un-reacted $CH_4$; (b) directing portion of the un-reacted $CH_4$ from the OCM product stream to (i) a steam methane reformer (SMR) that reacts $H_2O$ and the portion of the un-reacted $CH_4$ to yield $H_2$ and CO and/or $CO_2$, and/or (ii) a secondary reformer that reacts $O_2$ and the portion of the un-reacted $CH_4$ to yield $H_2$ and CO and/or $CO_2$; and (c) reacting nitrogen ($N_2$) and the $H_2$ produced in (a) and/or (b) to yield ammonia ($NH_3$).

In some embodiments of aspects provided herein, the method further comprises separating air to produce the $N_2$ reacted in (c) and the $O_2$ reacted in (b). In some embodiments of aspects provided herein, a ratio of (i) all nitrogen atoms in the $NH_3$ produced in (c) to (ii) all nitrogen atoms in $N_2$ produced upon separating the air is at least about 0.50. In some embodiments of aspects provided herein, in (c), the $H_2$ produced in (a) is reacted to yield $NH_3$. In some embodiments of aspects provided herein, in (c), the $H_2$ produced in (b) is reacted to yield $NH_3$. In some embodiments of aspects provided herein, (b) comprises (i). In some embodiments of aspects provided herein, (b) comprises (ii). In some embodiments of aspects provided herein, (b) comprises (i) and (ii).

An aspect of the present disclosure provides a system for producing ammonia ($NH_3$) and hydrocarbon compounds containing at least two carbon atoms ($C_{2+}$ compounds), comprising: an oxidative coupling of methane (OCM) reactor receives methane ($CH_4$) and oxygen ($O_2$) and reacts the $CH_4$ and the $O_2$ in an OCM process to yield an OCM product stream comprising the $C_{2+}$ compounds, hydrogen ($H_2$), and un-reacted $CH_4$; at least one of (i) a steam methane reformer (SMR) that receives $H_2O$ and a portion of the un-reacted $CH_4$ and reacts the $H_2O$ and the portion of the un-reacted $CH_4$ to yield $H_2$ and CO and/or $CO_2$ and (ii) a secondary reformer that receives $O_2$ and a portion of the un-reacted $CH_4$ and reacts the $O_2$ and the portion of the un-reacted $CH_4$ to yield $H_2$ and CO and/or $CO_2$; and an ammonia production module that receives nitrogen ($N_2$) and the $H_2$ produced in the SMR and/or the secondary reformer and reacts the $N_2$ and the $H_2$ to yield ammonia ($NH_3$).

In some embodiments of aspects provided herein, the system further comprises an air separation module that separates air to produce the $N_2$ reacted in the ammonia production module and the $O_2$ reacted in the SMR or the secondary reformer. In some embodiments of aspects provided herein, a ratio of (i) all nitrogen atoms in the $NH_3$ produced in the ammonia production module to (ii) all nitrogen atoms in $N_2$ produced upon separating the air is at least about 0.50. In some embodiments of aspects provided herein, the ammonia production module reacts the $H_2$ produced in the OCM reactor to yield $NH_3$. In some embodiments of aspects provided herein, the ammonia production module reacts the $H_2$ produced in the SMR or the secondary reformer to yield $NH_3$. In some embodiments of aspects provided herein, the system further comprises the SMR. In some embodiments of aspects provided herein, the system further comprises the secondary reformer. In some embodiments of aspects provided herein, the system further comprises the SMR and the secondary reformer.

An aspect of the present disclosure provides a method for producing ammonia ($NH_3$) and hydrocarbon compounds containing at least two carbon atoms ($C_{2+}$ compounds), comprising: (a) separating air to produce an oxygen stream comprising oxygen ($O_2$) and a nitrogen stream comprising nitrogen ($N_2$); (b) directing methane ($CH_4$) and a first portion of the oxygen stream into an oxidative coupling of methane (OCM) reactor that reacts the $CH_4$ and the $O_2$ from the first portion of the oxygen stream in an OCM process to yield an OCM product stream comprising the $C_{2+}$ compounds; (c) reacting hydrogen ($H_2$) and the $N_2$ produced in (a) to yield ammonia ($NH_3$).

In some embodiments of aspects provided herein, the method further comprises converting $CH_4$ to $CO_2$ and $H_2$ in a secondary reformer using a second portion of the oxygen stream. In some embodiments of aspects provided herein, the OCM product stream further comprises un-reacted $CH_4$ and wherein the $CH_4$ converted in the secondary reformer comprises at least a portion of the un-reacted $CH_4$. In some embodiments of aspects provided herein, the $H_2$ reacted in (c) comprises at least a portion of the $H_2$ produced in the secondary reformer. In some embodiments of aspects provided herein, a ratio of (i) all nitrogen atoms in the $NH_3$ produced in (c) to (ii) all nitrogen atoms in $N_2$ produced in (a) is at least about 0.50.

An aspect of the present disclosure provides a system for producing ammonia ($NH_3$) and hydrocarbon compounds containing at least two carbon atoms ($C_{2+}$ compounds), comprising: an air separation module that separates air to produce a nitrogen stream comprising nitrogen ($N_2$) and an oxygen stream comprising oxygen ($O_2$); an oxidative coupling of methane (OCM) module in fluid communication with the air separation module, wherein the OCM module (i) accepts methane ($CH_4$) and a first portion of the oxygen stream and (ii) reacts the $CH_4$ and the $O_2$ from the first portion of the oxygen stream in an OCM process that yields the $C_{2+}$ compounds, carbon monoxide (CO) and/or carbon dioxide ($CO_2$), hydrogen ($H_2$), and un-reacted $CH_4$; and an ammonia production module in fluid communication with the OCM module, wherein the ammonia production module (i) accepts the CO, the $H_2$, and the un-reacted $CH_4$ from the OCM module, and (ii) produces $NH_3$ from the CO, the $H_2$, and the un-reacted $CH_4$.

In some embodiments of aspects provided herein, the system further comprises a secondary reformer that accepts $CH_4$ and a second portion of the oxygen stream and converts the $CH_4$ and the $O_2$ from the second portion of the oxygen stream to $CO_2$ and $H_2$. In some embodiments of aspects provided herein, the OCM product stream further comprises un-reacted $CH_4$ and wherein the $CH_4$ converted in the secondary reformer comprises at least a portion of the un-reacted $CH_4$. In some embodiments of aspects provided herein, the $H_2$ accepted in by the ammonia production module comprises at least a portion of the $H_2$ produced in the secondary reformer. In some embodiments of aspects provided herein, a ratio of (i) all nitrogen atoms in the $NH_3$ produced in the ammonia production module to (ii) all nitrogen atoms in $N_2$ produced in the air separation module is at least about 0.50.

An aspect of the present disclosure provides a method for producing ammonia ($NH_3$) and hydrocarbon compounds containing at least two carbon atoms ($C_{2+}$ compounds), comprising: (a) separating air to produce oxygen ($O_2$) and nitrogen ($N_2$); (b) directing methane ($CH_4$) and a first portion of the oxygen ($O_2$) into an oxidative coupling of methane (OCM) reactor that reacts the $CH_4$ and the first portion of the $O_2$ in an OCM process to yield an OCM product stream comprising the $C_{2+}$ compounds, carbon monoxide (CO), hydrogen ($H_2$), and un-reacted $CH_4$; (c) directing the CO, the $H_2$ and the un-reacted $CH_4$ from the OCM product stream to a steam methane reformer (SMR); (d) in the SMR, converting a first portion of the un-reacted $CH_4$ to CO and Hz; (e) directing a second portion of the un-reacted $CH_4$ and a second portion of the $O_2$ into a secondary reformer that converts the second portion of the un-reacted $CH_4$ and the second portion of the $O_2$ to $CO_2$ and $H_2$; and (f) reacting the $N_2$ produced in (a) and the $H_2$ produced in (d) and/or (e) to yield ammonia ($NH_3$).

In some embodiments of aspects provided herein, the $H_2$ produced in (d) and (e) is reacted to yield ammonia ($NH_3$).

An aspect of the present disclosure provides a method for producing ammonia ($NH_3$) and hydrocarbon compounds containing at least two carbon atoms ($C_{2+}$ compounds), comprising: (a) separating air to produce oxygen ($O_2$) and nitrogen ($N_2$); (b) directing methane ($CH_4$) and a first portion of the oxygen ($O_2$) into an oxidative coupling of methane (OCM) reactor that reacts the $CH_4$ and the first portion of the $O_2$ in an OCM process to yield an OCM product stream comprising the $C_{2+}$ compounds; (c) directing $CH_4$ and a second portion of the oxygen ($O_2$) into a secondary reformer to convert $CH_4$ to $CO_2$ and Hz; and (e) reacting the $H_2$ produced in (c) with $N_2$ to yield ammonia ($NH_3$).

In some embodiments of aspects provided herein, the $H_2$ is reacted with at least a portion of the $N_2$ produced in (a). In some embodiments of aspects provided herein, the OCM product stream further comprises un-reacted $CH_4$, and wherein the $CH_4$ directed into the secondary reformer comprises at least a portion of the un-reacted $CH_4$.

An aspect of the present disclosure provides a method for producing ammonia ($NH_3$) and hydrocarbon compounds containing at least two carbon atoms ($C_{2+}$ compounds), comprising: (a) separating air to produce oxygen ($O_2$) and nitrogen ($N_2$); (b) directing methane ($CH_4$) and a first portion of the oxygen ($O_2$) into an oxidative coupling of methane (OCM) reactor that reacts the $CH_4$ and the first portion of the $O_2$ in an OCM process to yield an OCM product stream comprising the $C_{2+}$ compounds; (c) reacting hydrogen ($H_2$) and the $N_2$ produced in (a) to yield ammonia ($NH_3$).

In some embodiments of aspects provided herein, the method further comprises converting $CH_4$ to $CO_2$ and $H_2$ in a secondary reformer using a second portion of the $O_2$. In some embodiments of aspects provided herein, the OCM product stream further comprises un-reacted $CH_4$ and wherein the $CH_4$ converted in the secondary reformer comprises at least a portion of the un-reacted $CH_4$. In some embodiments of aspects provided herein, the $H_2$ reacted in (c) comprises at least a portion of the $H_2$ produced in the secondary reformer.

An aspect of the present disclosure provides a method for producing ammonia ($NH_3$) and hydrocarbon compounds containing at least two carbon atoms ($C_{2+}$ compounds), comprising: (a) directing methane ($CH_4$) and oxygen ($O_2$) into an oxidative coupling of methane (OCM) reactor that reacts the $CH_4$ and the $O_2$ in an OCM process to yield a product stream comprising the $C_{2+}$ compounds, carbon monoxide (CO), hydrogen ($H_2$), and un-reacted $CH_4$; (b) directing the CO, the $H_2$ and the un-reacted $CH_4$ from the product stream to a steam methane reformer (SMR); (c) converting a first portion of the un-reacted $CH_4$ to CO and $H_2$ in the SMR; and (d) reacting the $H_2$ produced in (c) with $N_2$ to yield ammonia ($NH_3$).

In some embodiments of aspects provided herein, the method further comprises separating air to produce oxygen ($O_2$) and nitrogen ($N_2$) and directing a first portion of the $O_2$ into the OCM reactor. In some embodiments of aspects provided herein, the $N_2$ reacted in (d) comprises at least a portion of the $N_2$ that was separated from the air. In some embodiments of aspects provided herein, the method further comprises converting a second portion of the un-reacted $CH_4$ to $CO_2$ and $H_2$ in a secondary reformer using a second portion of the $O_2$. In some embodiments of aspects provided herein, the $N_2$ reacted in (d) comprises at least a portion of the $N_2$ that was separated from the air.

An aspect of the present disclosure provides a system for producing ammonia ($NH_3$) and hydrocarbon compounds containing at least two carbon atoms ($C_{2+}$ compounds), comprising: (a) an oxidative coupling of methane (OCM) module that accepts methane ($CH_4$) and oxygen ($O_2$) and reacts the $CH_4$ and $O_2$ in an OCM process that yields the $C_{2+}$ compounds, carbon monoxide (CO), hydrogen ($H_2$), and un-reacted $CH_4$; and (b) an ammonia production module in fluid communication with the OCM module, wherein the ammonia production module (i) accepts the CO, the $H_2$, and the un-reacted $CH_4$ from the OCM module, and (ii) produces $NH_3$ from the CO, the $H_2$, and the un-reacted $CH_4$.

In some embodiments of aspects provided herein, the system further comprises (c) an air separation module in fluid communication with the OCM module and the ammonia production module, wherein the air separation module separates air into an oxygen stream and a nitrogen stream and (i) provides a portion of the oxygen stream to the OCM module, (ii) provides a portion of the oxygen stream to the ammonia production module, and/or (iii) provides the nitrogen stream to the ammonia production module.

An aspect of the present disclosure provides a system for producing ammonia ($NH_3$) and hydrocarbon compounds containing at least two carbon atoms ($C_{2+}$ compounds), comprising an air separation module in fluid communication with an OCM module and an ammonia production module, wherein the air separation module separates air into an oxygen stream and a nitrogen stream and (i) provides a portion of the oxygen stream to the OCM module, (ii) provides a portion of the oxygen stream to the ammonia production module, and/or (iii) provides the nitrogen stream to the ammonia production module.

In some embodiments of aspects provided herein, the oxidative coupling of methane (OCM) module accepts methane ($CH_4$) and oxygen ($O_2$) and reacts the $CH_4$ and $O_2$ in an OCM process that yields the $C_{2+}$ compounds, carbon monoxide (CO), hydrogen ($H_2$), and un-reacted $CH_4$. In some embodiments of aspects provided herein, the ammonia production module (i) accepts the CO, the $H_2$, and the un-reacted $CH_4$ from the OCM module, and (ii) produces $NH_3$ from the CO, the $H_2$, and the un-reacted $CH_4$.

An aspect of the present disclosure provides a method for producing hydrocarbon compounds containing at least two carbon atoms ($C_{2+}$ compounds), comprising: (a) directing a methanol product stream comprising methanol into a methanol-to-propylene (MTP) reactor that reacts the methanol to yield an MTP product stream comprising propylene and hydrocarbon compounds containing at least four carbon atoms ($C_{4+}$ compounds); (b) directing the MTP product stream into a separations system that separates the MTP product stream to yield a first stream comprising propylene and a second stream comprising the $C_{4+}$ compounds; (c) directing methane ($CH_4$) and oxygen ($O_2$) into an oxidative coupling of methane (OCM) reactor that reacts the $CH_4$ and the $O_2$ in an OCM process to yield an OCM product stream comprising the $C_{2+}$ compounds, carbon dioxide ($CO_2$), hydrogen ($H_2$), and un-reacted $CH_4$; and (d) directing the OCM product stream into the separations system, and in the separations system, separating the OCM product stream to yield a third stream comprising ethylene.

In some embodiments of aspects provided herein, the method further comprises, before directing the OCM product stream into the separations system, removing $CO_2$ from the OCM product stream in a $CO_2$ removal unit and directing the $CO_2$ into the methanol reactor. In some embodiments of aspects provided herein, the method further comprises, before directing the OCM product stream into the separations system, removing $CH_4$ from the OCM product stream in a de-methanizer unit and directing the $CH_4$ into the syngas reactor. In some embodiments of aspects provided herein, the method further comprises, before directing the OCM product stream into the separations system, removing water ($H_2O$) from the OCM product stream in a drying unit. In some embodiments of aspects provided herein, the method further comprises generating the methanol product stream directing a syngas product stream comprising (i) hydrogen ($H_2$) and (ii) carbon monoxide (CO) and/or carbon dioxide ($CO_2$) into a methanol reactor that reacts the $H_2$ and the CO and/or $CO_2$ to yield the methanol product stream. In some embodiments of aspects provided herein, the method further comprises generating the syngas product stream by directing a syngas feed stream comprising $CH_4$ into a syngas reactor that reacts the $CH_4$ in the syngas feed stream to yield the syngas product stream.

An aspect of the present disclosure provides a system for producing hydrocarbon compounds containing at least two carbon atoms ($C_{2+}$ compounds), comprising: a methanol-to-propylene (MTP) reactor that receives a methanol product stream comprising methanol and reacts the methanol to yield an MTP product stream comprising propylene and hydrocarbon compounds containing at least four carbon atoms ($C_{4+}$ compounds); a separations system in fluid communication with the MTP reactor, wherein the separation system receives the MTP product stream and separates the MTP product stream to yield a first stream comprising propylene and a second stream comprising the $C_{4+}$ compounds; and an oxidative coupling of methane (OCM) reactor that (i) receives methane ($CH_4$) and oxygen ($O_2$), (ii) reacts the $CH_4$ and the $O_2$ in an OCM process to yield an OCM product stream comprising the $C_{2+}$ compounds, carbon dioxide ($CO_2$), hydrogen ($H_2$), and un-reacted $CH_4$, and (iii) directs the OCM product stream into the separations system to yield a third stream comprising ethylene.

In some embodiments of aspects provided herein, the system further comprises a $CO_2$ removal unit located downstream of the OCM reactor and upstream of the separations system that removes $CO_2$ from the OCM product stream and directs the $CO_2$ into the methanol reactor. In some embodiments of aspects provided herein, the system further comprises a de-methanizer unit located downstream of the OCM reactor and upstream of the separations system that removes $CH_4$ from the OCM product stream directs the $CH_4$ into the syngas reactor. In some embodiments of aspects provided herein, the system further comprises a drying unit located downstream of the OCM reactor and upstream of the separations system that removes water ($H_2O$) from the OCM product stream. In some embodiments of aspects provided herein, the system further comprises a methanol reactor that receives a syngas product stream comprising (i) hydrogen ($H_2$) and (ii) carbon monoxide (CO) and/or carbon dioxide ($CO_2$) and reacts the $H_2$ and the CO and/or $CO_2$ to yield the methanol product stream. In some embodiments of aspects provided herein, the system further comprises a syngas reactor that receives a syngas feed stream comprising $CH_4$ and reacts the $CH_4$ in the syngas feed stream to yield the syngas product stream.

An aspect of the present disclosure provides a method for producing liquid natural gas (LNG), comprising: (a) directing methane ($CH_4$) from a gas processing plant and oxygen ($O_2$) into an oxidative coupling of methane (OCM) reactor that reacts the $CH_4$ and the $O_2$ in an OCM process to yield an OCM product stream comprising hydrocarbon compounds containing at least two carbon atoms ($C_{2+}$ compounds); (b) directing the OCM product stream into an ethylene-to-liquids (ETL) reactor that reacts the $C_{2+}$ compounds in an ETL process to yield an ETL product stream comprising compounds containing at least five carbon atoms ($C_{5+}$ compounds); and (c) directing the $C_{5+}$ compounds from the ETL product stream to a liquid petroleum gas (LPG) module of the gas processing plant, which LPG module produces condensate from petroleum gas.

In some embodiments of aspects provided herein, the method further comprises directing $C_2$ compounds from an LPG extraction unit of the gas processing plant into the OCM reactor. In some embodiments of aspects provided herein, the method further comprises directing the $C_{5+}$ compounds along with condensate from the LPG module. In some embodiments of aspects provided herein, the method further comprises directing at least a portion of the ETL product stream into a gas treatment unit of the gas processing plant.

An aspect of the present disclosure provides a system for producing liquid natural gas (LNG), comprising: an oxidative coupling of methane (OCM) reactor that receives methane ($CH_4$) from a gas processing plant and oxygen ($O_2$) and reacts the $CH_4$ and the $O_2$ in an OCM process to yield an OCM product stream comprising hydrocarbon compounds containing at least two carbon atoms ($C_{2+}$ compounds); and an ethylene-to-liquids (ETL) module in fluid communication with the OCM reactor, wherein the ETL module (i) receives the OCM product stream, (ii) reacts the $C_{2+}$ compounds in an ETL process to yield an ETL product stream comprising compounds containing at least five carbon atoms ($C_{5+}$ compounds), and (iii) directs the $C_{5+}$ compounds from the ETL product stream to a liquid petroleum gas (LPG) module of the gas processing plant, which LPG module produces condensate from petroleum gas.

In some embodiments of aspects provided herein, the system further comprises an LPG extraction unit of the gas processing plant that directs $C_2$ compounds into the OCM reactor. In some embodiments of aspects provided herein, the ETL modules directs the $C_{5+}$ compounds along with condensate from the LPG module. In some embodiments of aspects provided herein, the ETL modules directs at least a portion of the ETL product stream into a gas treatment unit of the gas processing plant.

An aspect of the present disclosure provides a method for producing polyethylene, comprising: (a) directing $C_2$ compounds from a liquid petroleum gas (LPG) extraction unit of a gas processing plant into a $C_2$ splitting unit that separates the $C_2$ compounds to yield an ethane stream comprising ethane and an ethylene stream comprising ethylene; (b) directing the ethylene stream into a polyethylene reactor that reacts the ethylene in the ethylene stream to yield a polyethylene product stream comprising polyethylene; and (c) directing the ethane stream, methane ($CH_4$) from the LPG extraction unit, and oxygen ($O_2$) into an oxidative coupling of methane (OCM) reactor that reacts the $CH_4$ and the $O_2$ in an OCM process to yield an OCM product stream comprising hydrocarbon compounds containing at least two carbon atoms ($C_{2+}$ compounds).

In some embodiments of aspects provided herein, the method further comprises directing the OCM product stream into a gas treatment unit of the gas processing plant.

An aspect of the present disclosure provides a system for producing polyethylene, comprising: a $C_2$ splitting unit that receives $C_2$ compounds from a liquid petroleum gas (LPG) extraction unit of a gas processing plant and separates the $C_2$ compounds to yield an ethane stream comprising ethane and an ethylene stream comprising ethylene; a polyethylene reactor that receives the ethylene stream and reacts the ethylene in the ethylene stream to yield a polyethylene product stream comprising polyethylene; and an oxidative coupling of methane (OCM) reactor that receives the ethane stream, methane ($CH_4$) from the LPG extraction unit, and oxygen ($O_2$) and reacts the $CH_4$ and the $O_2$ in an OCM process to yield an OCM product stream comprising hydrocarbon compounds containing at least two carbon atoms ($C_{2+}$ compounds).

In some embodiments of aspects provided herein, the system further comprises a gas treatment unit of the gas processing plant that receives the OCM product stream.

An aspect of the present disclosure provides a method for producing oxalate compounds, comprising: (a) directing methane ($CH_4$) and oxygen ($O_2$) into an oxidative coupling of methane (OCM) reactor that reacts the $CH_4$ and the $O_2$ in an OCM process to yield an OCM product stream comprising hydrocarbon compounds containing at least two carbon atoms ($C_{2+}$ compounds) and carbon monoxide (CO) and/or carbon dioxide ($CO_2$); and (b) directing the CO and/or $CO_2$ from the OCM product stream into an oxalate reactor that reacts the CO and/or $CO_2$ to yield an oxalate product stream comprising oxalic acid and/or an oxalate.

In some embodiments of aspects provided herein, the method further comprises directing the oxalate product stream into a hydrogenation reactor that reacts the oxalic acid and/or the oxalate to yield an oxalate derivate product. In some embodiments of aspects provided herein, the oxalate derivative product is selected from the group consisting of glycolic acid, ethylene glycol, diglycolic acid, nitriloacetic acid, glyoxylic acid, acetic acid, salts thereof, and combinations thereof. In some embodiments of aspects provided herein, the oxalate reactor is an electrochemical reactor. In some embodiments of aspects provided herein, the method further comprises directing $H_2$ from the OCM product stream, from a propane dehydrogenation unit, from a steam reformer, from a water electrolysis unit, from a steam electrolysis unit, or any combination thereof into the oxalate reactor. In some embodiments of aspects provided herein, at least 50% of the $CO_2$ produced by the OCM reactor is converted into oxalic acid and/or an oxalate.

An aspect of the present disclosure provides a system for producing oxalate compounds, comprising: an oxidative coupling of methane (OCM) reactor that receives methane ($CH_4$) and oxygen ($O_2$) and reacts the $CH_4$ and the $O_2$ in an OCM process to yield an OCM product stream comprising hydrocarbon compounds containing (i) at least two carbon atoms ($C_{2+}$ compounds) and (ii) carbon monoxide (CO) and/or carbon dioxide ($CO_2$); and an oxalate reactor that receives the CO and/or $CO_2$ from the OCM product stream and reacts the CO and/or $CO_2$ to yield an oxalate product stream comprising oxalic acid and/or an oxalate.

In some embodiments of aspects provided herein, the system further comprises a hydrogenation reactor that receives the oxalate product stream and reacts the oxalic acid and/or the oxalate to yield an oxalate derivate product. In some embodiments of aspects provided herein, the oxalate derivative product is selected from the group consisting of glycolic acid, ethylene glycol, diglycolic acid, nitriloacetic acid, glyoxylic acid, acetic acid, salts thereof, and combinations thereof. In some embodiments of aspects provided herein, the oxalate reactor is an electrochemical reactor. In some embodiments of aspects provided herein, the oxalate reactor receives $H_2$ from the OCM product stream. In some embodiments of aspects provided herein, at least 50% of the $CO_2$ produced by the OCM reactor is converted into oxalic acid and/or an oxalate.

An aspect of the present disclosure provides a method for producing ethylene derivatives, comprising: (a) directing a methane ($CH_4$) stream comprising $CH_4$ and a first oxygen ($O_2$) stream comprising $O_2$ into an oxidative coupling of methane (OCM) reactor that reacts the $CH_4$ and the $O_2$ in the $CH_4$ stream and $O_2$ stream, respectively, in an OCM process to yield an OCM product stream comprising hydrocarbon compounds containing at least two carbon atoms ($C_{2+}$ compounds) including ethylene; and (b) directing the ethylene from the OCM product stream and a second $O_2$ stream comprising $O_2$ into an oxidation reactor that reacts the ethylene and the $O_2$ in the second $O_2$ stream to yield an oxidation product stream comprising ethylene oxide.

In some embodiments of aspects provided herein, the method further comprises directing the oxidation product stream into a hydration reactor that reacts the ethylene oxide to yield ethylene glycol.

An aspect of the present disclosure provides a system for producing ethylene derivatives, comprising: an oxidative coupling of methane (OCM) reactor that receives a methane ($CH_4$) stream comprising $CH_4$ and a first oxygen ($O_2$) stream comprising $O_2$ and reacts the $CH_4$ and the $O_2$ in the $CH_4$ stream and $O_2$ stream, respectively, in an OCM process to yield an OCM product stream comprising hydrocarbon compounds containing at least two carbon atoms ($C_{2+}$ compounds) including ethylene; and an oxidation reactor that receives the ethylene from the OCM product stream and a second $O_2$ stream comprising $O_2$ and reacts the ethylene and the $O_2$ in the second $O_2$ stream to yield an oxidation product stream comprising ethylene oxide.

In some embodiments of aspects provided herein, the system further comprises a hydration reactor that receives the oxidation product stream and reacts the ethylene oxide to yield ethylene glycol.

An aspect of the present disclosure provides a method for producing propylene, comprising: (a) directing methane ($CH_4$) and oxygen ($O_2$) into an oxidative coupling of methane (OCM) reactor that reacts the $CH_4$ and the $O_2$ to yield an OCM product stream comprising hydrocarbon compounds containing at least two carbon atoms ($C_{2+}$ compounds) including ethylene; (b) directing the OCM product stream into a separations unit that yields an ethylene stream comprising ethylene from the OCM product stream; (c) directing a first portion of ethylene from the ethylene stream into a dimerization reactor that reacts the ethylene in a dimerization reaction to yield a butene stream comprising butene compounds; (d) directing the butene stream into a $C_4$ separations unit that yields a butene-2 stream comprising butene-2 from the butene stream; and (e) directing the butene-2 stream and a second portion of ethylene from the ethylene stream into a metathesis reactor that reacts the butene-2 and the ethylene to yield a metathesis product stream comprising $C_{2+}$ compounds including propylene.

In some embodiments of aspects provided herein, the method further comprises directing the metathesis product stream into a $C_2$ separations unit that separates the metathesis product stream to yield a $C_2$ stream comprising $C_2$ compounds and a $C_{3+}$ stream comprising $C_{3+}$ compounds including propylene. In some embodiments of aspects provided herein, the method further comprises directing the $C_2$ stream into the separations unit. In some embodiments of aspects provided herein, the method further comprises directing the $C_{3+}$ stream into a $C_3$ separations unit that separates the $C_{3+}$ stream to yield a $C_3$ stream comprising propylene and a $C_{4+}$ stream comprising $C_{4+}$ products. In some embodiments of aspects provided herein, the method further comprises directing the $C_{4+}$ stream into the $C_4$ separations unit. In some embodiments of aspects provided herein, the method further comprises directing the propylene from the metathesis product stream into a polypropylene unit that reacts the propylene to yield a polypropylene product stream comprising polypropylene. In some embodiments of aspects provided herein, the method further comprises directing ethylene from the separations unit to the polypropylene unit, wherein the polypropylene unit reacts the ethylene as a co-monomer with the propylene. In some embodiments of aspects provided herein, the ratio of ethylene co-monomer to total monomer and co-monomer is from about 0.01:0.99 to about 0.15:0.85 In some embodiments of aspects provided herein, the ratio of ethylene co-monomer to total monomer and co-monomer is from about 0.08:0.92 to about 0.15:0.85. In some embodiments of aspects provided herein, step (a) further comprises directing ethane ($C_2H_6$) into the OCM reactor.

An aspect of the present disclosure provides a system for producing propylene, comprising: an oxidative coupling of methane (OCM) reactor that receives methane ($CH_4$) and oxygen ($O_2$) and reacts the $CH_4$ and the $O_2$ to yield an OCM product stream comprising hydrocarbon compounds containing at least two carbon atoms ($C_{2+}$ compounds) including ethylene; a separations unit that receives the OCM product stream and yields an ethylene stream comprising ethylene from the OCM product stream; a dimerization reactor that receives a first portion of ethylene from the ethylene stream and reacts the ethylene in a dimerization reaction to yield a butene stream comprising butene compounds; a $C_4$ separations unit that receives the butene stream and yields a butene-2 stream comprising butene-2 from the butene stream; and a metathesis reactor that receives the butene-2 stream and a second portion of ethylene from the ethylene stream and reacts the butene-2 and the ethylene to yield a metathesis product stream comprising $C_{2+}$ compounds including propylene.

In some embodiments of aspects provided herein, the system further comprises a $C_2$ separations unit that receives the metathesis product stream and separates the metathesis product stream to yield a $C_2$ stream comprising $C_2$ compounds and a $C_{3+}$ stream comprising $C_{3+}$ compounds including propylene. In some embodiments of aspects provided herein, the separations unit receives the $C_2$ stream. In some embodiments of aspects provided herein, the system further comprises a $C_3$ separations unit that receives the $C_{3+}$ stream and separates the $C_{3+}$ stream to yield a $C_3$ stream comprising propylene and a $C_{4+}$ stream comprising $C_{4+}$ products. In some embodiments of aspects provided herein, the $C_4$ separations unit receives the $C_{4+}$ stream. In some embodiments of aspects provided herein, the system further comprises a polypropylene unit that receives the propylene from the metathesis product stream and reacts the propylene to yield a polypropylene product stream comprising polypropylene. In some embodiments of aspects provided herein, the polypropylene unit receives ethylene from the separations unit and reacts the ethylene as a co-monomer with the propylene. In some embodiments of aspects provided herein, the ratio of ethylene co-monomer to total monomer and co-monomer is from about 0.01:0.99 to about 0.15:0.85 In some embodiments of aspects provided herein, the ratio of ethylene co-monomer to total monomer and co-monomer is from about 0.08:0.92 to about 0.15:0.85. In some embodiments of aspects provided herein, the OCM reactor receives ethane ($C_2H_6$).

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE FIGURES

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings or figures (also referred to herein as "FIG." and "FIGS."), of which:

DETAILED DESCRIPTION

Figure 1A:
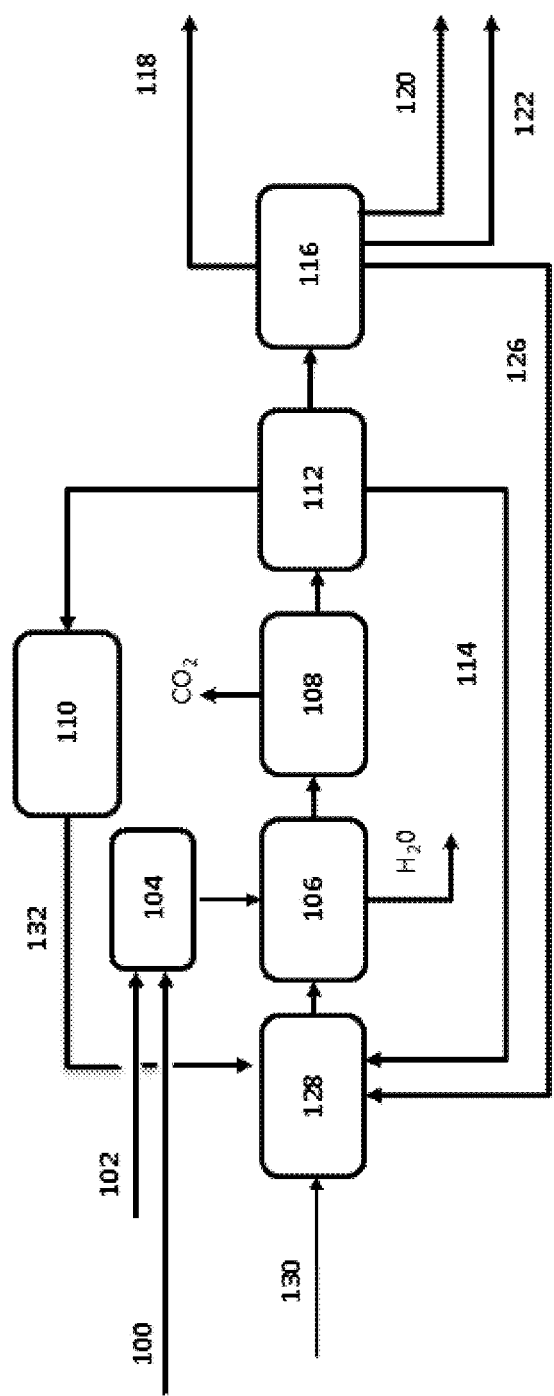
FIG. 1A is a schematic illustration of an oxidative coupling of methane (OCM) process.

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

The term "higher hydrocarbon," as used herein, generally refers to a higher molecular weight and/or higher chain hydrocarbon. A higher hydrocarbon can have a higher molecular weight and/or carbon content that is higher or larger relative to starting material in a given process (e.g., OCM or ETL). A higher hydrocarbon can be a higher molecular weight and/or chain hydrocarbon product that is generated in an OCM or ETL process. For example, ethylene is a higher hydrocarbon product relative to methane in an OCM process. As another example, a $C_{3+}$ hydrocarbon is a higher hydrocarbon relative to ethylene in an ETL process. As another example, a $C_{5+}$ hydrocarbon is a higher hydrocarbon relative to ethylene in an ETL process. In some cases, a higher hydrocarbon is a higher molecular weight hydrocarbon.

The term "OCM process," as used herein, generally refers to a process that employs or substantially employs an oxidative coupling of methane (OCM) reaction. An OCM reaction can include the oxidation of methane to a higher hydrocarbon and water, and involves an exothermic reaction. In an OCM reaction, methane can be partially oxidized and coupled to form one or more $C_{2+}$ compounds, such as ethylene. In an example, an OCM reaction is $2CH_4+O_2 \rightarrow C_2H_4+2H_2O$. An OCM reaction can yield $C_{2+}$ compounds. An OCM reaction can be facilitated by a catalyst, such as a heterogeneous catalyst. Additional by-products of OCM reactions can include CO, $CO_2$, $H_2$, as well as hydrocarbons, such as, for example, ethane, propane, propene, butane, butene, and the like.

The term "non-OCM process," as used herein, generally refers to a process that does not employ or substantially employ an oxidative coupling of methane reaction. Examples of processes that may be non-OCM processes include non-OCM hydrocarbon processes, such as, for example, non-OCM processes employed in hydrocarbon processing in oil refineries, a natural gas liquids separations processes, steam cracking of ethane, steam cracking or naphtha, Fischer-Tropsch processes, and the like.

The terms "$C_{2+}$" and "$C_{2+}$ compound," as used herein, generally refer to a compound comprising two or more carbon atoms. For example, $C_{2+}$ compounds include, without limitation, alkanes, alkenes, alkynes and aromatics containing two or more carbon atoms. $C_{2+}$ compounds can include aldehydes, ketones, esters and carboxylic acids. Examples of $C_{2+}$ compounds include ethane, ethene, acetylene, propane, propene, butane, and butene.

The term "non-$C_{2+}$ impurities," as used herein, generally refers to material that does not include $C_{2+}$ compounds. Examples of non-$C_{2+}$ impurities, which may be found in certain OCM reaction product streams, include nitrogen ($N_2$), oxygen ($O_2$), water ($H_2O$), argon (Ar), hydrogen ($H_2$) carbon monoxide (CO), carbon dioxide ($CO_2$) and methane ($CH_4$).

The term "small scale," as used herein, generally refers to a system that generates less than or equal to about 250 kilotons per annum (KTA) of a given product, such as an olefin (e.g., ethylene).

The term "world scale," as used herein, generally refers to a system that generates greater than about 250 KTA of a given product, such as an olefin (e.g., ethylene). In some examples, a world scale olefin system generates at least about 1000, 1100, 1200, 1300, 1400, 1500, or 1600 KTA of an olefin.

The term "item of value," as used herein, generally refers to money, credit, a good or commodity (e.g., hydrocarbon). An item of value can be traded for another item of value.

The term "carbon efficiency," as used herein, generally refers to the ratio of the number of moles of carbon present in all process input streams (in some cases including all hydrocarbon feedstocks, such as, e.g., natural gas and ethane and fuel streams) to the number of moles of carbon present in all commercially (or industrially) usable or marketable products of the process. Such products can include hydrocarbons that can be employed for various downstream uses, such as petrochemical or for use as commodity chemicals. Such products can exclude CO and $CO_2$. The products of the process can be marketable products, such as $C_{2+}$ hydrocarbon products containing at least about 99% $C_{2+}$ hydrocarbons and all sales gas or pipeline gas products containing at least about 90% methane. Process input streams can include input streams providing power for the operation of the process, such as with the aid of a turbine (e.g., steam turbine). In some cases, power for the operation of the process can be provided by heat liberated by an OCM reaction.

The term "nitrogen efficiency," as used herein, generally refers to the ratio of the number of moles of nitrogen present in all process input streams (in some cases including all nitrogen feedstocks, such as, e.g., air or purified nitrogen) to the number of moles of nitrogen present in all commercially (or industrially) usable or marketable products of the process. Such products can include ammonia and other nitrogen products that can be employed for various downstream uses, such as petrochemical use, agricultural use, or for use as commodity chemicals. Such products can exclude nitrogen oxides (NOx), such as NO and $NO_2$. The products of the process can be marketable products, such as ammonia and derivatives thereof containing at least about 90% or 99% ammonia or ammonia derivatives. Process input streams can include input streams providing power for the operation of the process, such as with the aid of a turbine (e.g., steam turbine). In some cases, power for the operation of the process can be provided by heat liberated by a reaction, such as an OCM reaction.

The term "$C_{2+}$ selectivity," as used herein, generally refers to the percentage of the moles of methane that are converted into $C_{2+}$ compounds.

The term "specific oxygen consumption," as used herein, generally refers to the mass (or weight) of oxygen consumed by a process divided by the mass of $C_{2+}$ compounds produced by the process.

The term "specific $CO_2$ emission," as used herein, generally refers to the mass of $CO_2$ emitted from the process divided by the mass of $C_{2+}$ compounds produced by the process.

OCM Processes

In an OCM process, methane ($CH_4$) reacts with an oxidizing agent over a catalyst bed to generate $C_{2+}$ compounds. For example, methane can react with oxygen over a suitable catalyst to generate ethylene, e.g., $2 CH_4+O_2 \rightarrow C_2H_4+2 H_2O$ (See, e.g., Zhang, Q., *Journal of Natural Gas Chem.*, 12:81, 2003; Olah, G. "Hydrocarbon Chemistry", Ed. 2, John Wiley & Sons (2003)). This reaction is exothermic ($\Delta H=-280$ kJ/mol) and has typically been shown to occur at very high temperatures (e.g., >450° C. or >700° C.). Non-selective reactions that can occur include (a) $CH_4+2O_2 \rightarrow CO_2+2 H_2O$ and (b) $CH_4+\frac{1}{2} O_2 \rightarrow CO+2 H_2$. These non-selective reactions are also exothermic, with reaction heats of $-891$ kJ/mol and $-36$ kJ/mol respectively. The conversion of methane to $CO_x$ products is undesirable due to both heat management and carbon efficiency concerns.

Experimental evidence suggests that free radical chemistry is involved. (Lunsford, *J. Chem. Soc., Chem. Comm.*, 1991; H. Lunsford, *Angew. Chem., Int. Ed. Engl.*, 34:970, 1995). In the reaction, methane ($CH_4$) is activated on the catalyst surface, forming methyl radicals which then couple on the surface or in the gas phase to form ethane ($C_2H_6$), followed by dehydrogenation to ethylene ($C_2H_4$). The OCM reaction pathway can have a heterogeneous/homogeneous mechanism, which involves free radical chemistry. Experimental evidence has shown that an oxygen active site on the catalyst activates the methane, removes a single hydrogen atom and creates a methyl radical. Methyl radicals react in the gas phase to produce ethane, which is either oxidative or non-oxidatively dehydrogenated to ethylene. The main reactions in this pathway can be as follows: (a) $CH_4+O^-$ →$CH_3^* + OH^-$; (b) $2\ CH_3^* \rightarrow C_2H_6$; (c) $C_2H_6 + O^- \rightarrow C_2H_4 + H_2O$. In some cases, to improve the reaction yield, ethane can be introduced downstream of the OCM catalyst bed and thermally dehydrogenated via the following reaction: $C_2H_6 \rightarrow C_2H_4 + H_2$. This reaction is endothermic ($\Delta H = 144$ kJ/mol), which can utilize the exothermic reaction heat produced during methane conversion. Combining these two reactions in one vessel can increase thermal efficiency while simplifying the process.

Several catalysts have shown activity for OCM, including various forms of iron oxide, $V_2O_5$, $MoO_3$, $Co_3O_4$, Pt—Rh, $Li/ZrO_2$, Ag—Au, $Au/Co_3O_4$, Co/Mn, $CeO_2$, MgO, $La_2O_3$, $Mn_3O_4$, $Na_2WO_4$, MnO, ZnO, and combinations thereof, on various supports. A number of doping elements have also proven to be useful in combination with the above catalysts.

Since the OCM reaction was first reported over thirty years ago, it has been the target of intense scientific and commercial interest, but the fundamental limitations of the conventional approach to C—H bond activation appear to limit the yield of this attractive reaction under practical operating conditions. Specifically, numerous publications from industrial and academic labs have consistently demonstrated characteristic performance of high selectivity at low conversion of methane, or low selectivity at high conversion (J. A. Labinger, Cat. Lett., 1:371, 1988). Limited by this conversion/selectivity threshold, no OCM catalyst has been able to exceed 20-25% combined $C_2$ yield (i.e., ethane and ethylene), and more importantly, all such reported yields required extremely high reactor inlet temperatures (>800° C.). Novel catalysts and processes have been described for use in performing OCM in the production of ethylene from methane at substantially more practicable temperatures, pressures and catalyst activities. These are described in U.S. patent application Ser. Nos. 13/115,082, 13/479,767, 13/689,611, 13/689,514, 13/901,319, 14/212,435, and 14/701,963, the full disclosures of each of which are incorporated herein by reference in its entirety for all purposes.

An OCM reactor can include a catalyst that facilitates an OCM process. The catalyst may include a compound including at least one of an alkali metal, an alkaline earth metal, a transition metal, and a rare-earth metal. The catalyst may be in the form of a honeycomb, packed bed, or fluidized bed. In some embodiments, at least a portion of the OCM catalyst in at least a portion of the OCM reactor can include one or more OCM catalysts and/or nanostructure-based OCM catalyst compositions, forms and formulations. Examples of OCM reactors, separations for OCM, and OCM process designs are described in U.S. patent application Ser. Nos. 13/739,954, 13/900,898, 13/936,783, 14/553,795, and 14/592,688, the full disclosures of each of which are incorporated herein by reference in its entirety for all purposes. An OCM reactor can be adiabatic or substantially adiabatic (including, for example, a post-bed cracking unit). An OCM reactor can be isothermal or substantially isothermal.

With reference to FIG. 1A, natural gas 100 and ethane 102 can enter the process through a de-sulfurization module 104, which can flow into a process gas compression module 106 where water can be removed. OCM product gas can be added to the process gas compression module 106 as well. A process gas cleanup module 108 can remove carbon dioxide ($CO_2$), some or all which can be taken to a methanation module 110. Following cleanup, the process gas can flow into a first separations module 112 that removes $C_{2+}$ compounds from the process gas stream. The remaining process gas can flow to the methanation module 110 and/or a fired heater (e.g., to heat incoming OCM gas streams 114).

The $C_{2+}$ compounds can be fractionated in a second separations module 116 to produce ethylene ($C_2H_4$) 118, $C_3$ compounds 120, and $C_{4+}$ compounds 122 for example. The second separations module 116 can produce an ethane ($C_2H_6$) stream 126 that is returned to the OCM reactor 128. At the OCM reactor 128, oxygen 130 can be reacted with methane from the methanation module 132. Outside boundary limits (OSBL) systems include a steam system, a boiler feed water system and a cooling water system.

Figure 2:
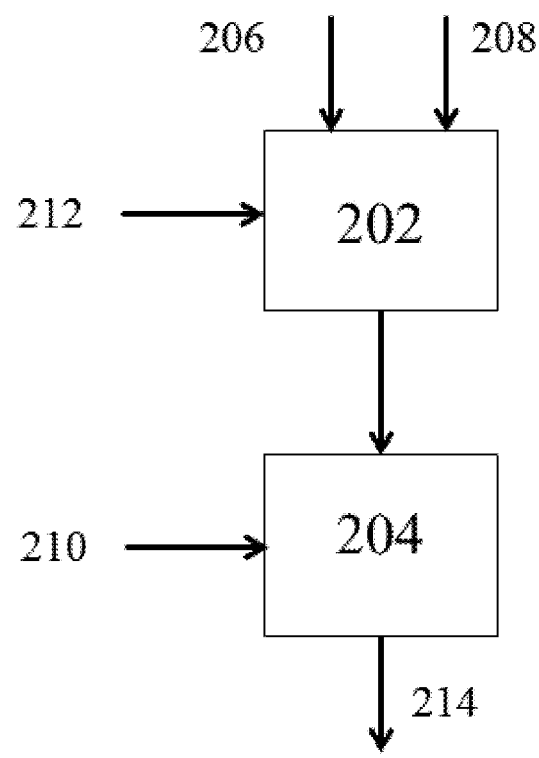
FIG. 2 is a schematic illustration of addition of ethane to an OCM reactor.

The OCM reactor can perform the OCM reaction and post-bed cracking (PBC), as described in U.S. patent application Ser. No. 14/553,795, which is incorporated herein by reference in its entirety. With reference to FIG. 2, the OCM reactor 200 can have an OCM reaction section 202 and a PBC section 204. Methane 206 (e.g., natural gas) and oxygen 208 can be injected (via a mixer) in to the OCM reaction region (which comprises an OCM catalyst). The OCM reaction is exothermic and the heat of reaction can be used to crack additional ethane 210 that can be injected into the PBC region 204. In some cases, yet more ethane 212 is also injected into the OCM reaction region 202 and/or the methane feed is supplemented with ethane or other $C_{2+}$ alkanes (e.g., propane or butane). The OCM reactor produces an OCM effluent 214.

The relative amounts of supplemental ethane 210 and 212 can be varied to achieve a range of product outcomes from the system. In some cases, no ethane is injected into the OCM reaction region 202 (referred to herein as Case-1). Another case presented herein has 3.5 mol % ethane injected into the OCM region (referred to herein as Case-2). Some process design results are presented in Table 1.

TABLE 1

Examples of various amounts of ethane in OCM feed

|  | Case-1 | Case-2 |
| --- | --- | --- |
| Natural gas consumed (MMSCFD) | 15.5 | 16 |
| Ethane consumed (MMSCFD) | 2.2 | 8.3 |
| [Ethane] at inlet (mol %) | 0.07 | 3.5 |
| [Ethylene] at outlet (mol %) | 3.6 | 4.9 |
| $C_2$ products (kTa) | 85 | 115 |
| $C_3$ products (kTa) | 10.3 | 21.1 |
| $C_{4+}$ products (kTa) | 2.7 | 2.5 |
| $O_2$ consumed (ton/ton ethylene) | 2.2 | 1.8 |
| $CO_2$ produced from OCM (ton/ton ethylene) | 0.9 | 0.7 |
| $CO_2$ produced from fired heater (ton/ton ethylene) | 0.6 | 0.4 |

In some cases, the amount of hydrogen ($H_2$) exiting the OCM reactor is relatively higher for cases having relatively more ethane injection (e.g., 8% $H_2$ for Case-1 and about $H_2$ 10% for Case-2). The amount of ethane that can be injected can be limited by the desired temperature exiting the OCM reaction region 202 or the OCM reactor 214.

In some cases, the process equipment is sized to accommodate a range of amounts of additional ethane such that the process is flexible. For example, more ethane can be injected into the process when the price of ethane is relatively cheap in comparison to the price of natural gas (e.g., low frac spread).

Figure 1B:
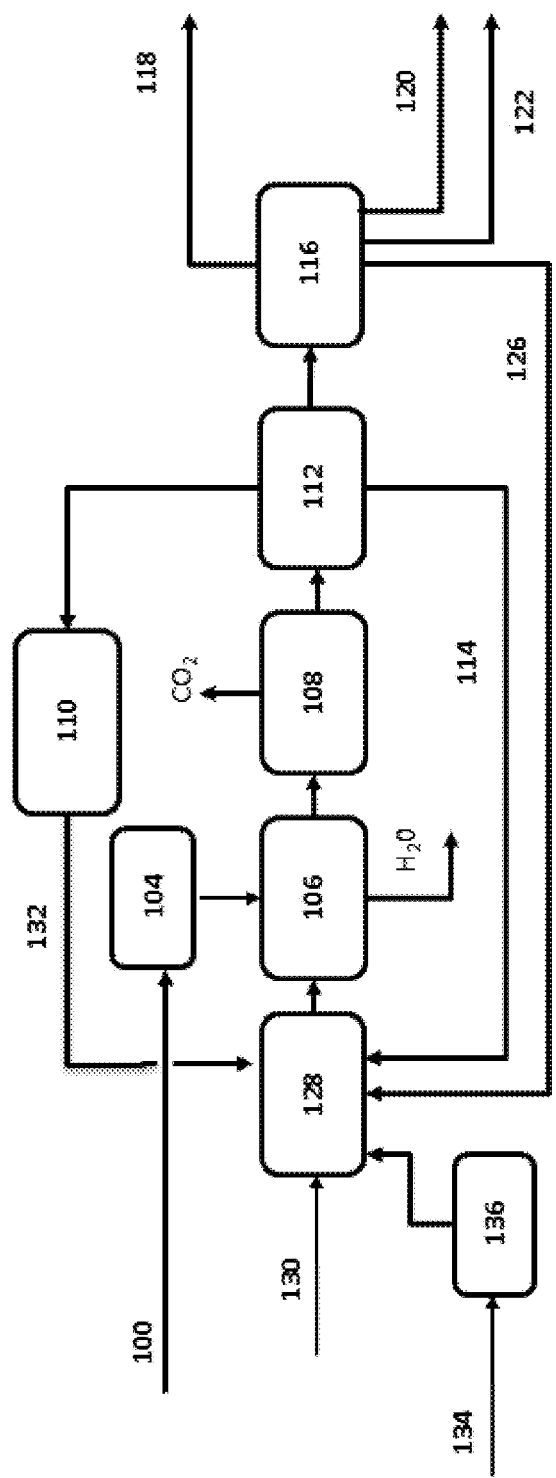
FIG. 1B is a schematic illustration of an oxidative coupling of methane (OCM) process with separate addition of ethane.

The ethane can be mixed with the natural gas and recycled to the OCM unit (as shown in FIG. 1A). In some cases, with reference to FIG. 1B, the ethane 134 can go straight to the OCM reactor, optionally through a separate de-sulfurization module 136. Injection of ethane through a separate de-sulfurization module can reduce the load in the recycle loop of the process and/or give additional production capacity keeping the same recirculation rate. The purge gas from the process can be used for fuel gas to the fired heater or sales gas.

The concentration of ethane in the feed to the OCM reactor can be any suitable value, including about 0.0 mol %, about 0.25 mol %, about 0.5 mol %, about 0.75 mol %, about 1.0 mol %, about 1.25 mol %, about 1.5 mol %, about 1.75 mol %, about 2.0 mol %, about 2.25 mol %, about 2.5 mol %, about 2.75 mol %, about 3.0 mol %, about 3.25 mol %, about 3.5 mol %, about 3.75 mol %, about 4.0 mol %, about 4.25 mol %, about 4.5 mol %, about 4.75 mol %, about 5.0 mol %, about 5.25 mol %, about 5.5 mol %, about 5.75 mol %, about 6.0 mol %, or more. In some cases, the concentration of ethane in the feed to the OCM reactor is at least about 0.0 mol %, at least about 0.25 mol %, at least about 0.5 mol %, at least about 0.75 mol %, at least about 1.0 mol %, at least about 1.25 mol %, at least about 1.5 mol %, at least about 1.75 mol %, at least about 2.0 mol %, at least about 2.25 mol %, at least about 2.5 mol %, at least about 2.75 mol %, at least about 3.0 mol %, at least about 3.25 mol %, at least about 3.5 mol %, at least about 3.75 mol %, at least about 4.0 mol %, at least about 4.25 mol %, at least about 4.5 mol %, at least about 4.75 mol %, at least about 5.0 mol %, at least about 5.25 mol %, at least about 5.5 mol %, at least about 5.75 mol %, at least about 6.0 mol %, or more. In some cases, the concentration of ethane in the feed to the OCM reactor is at most about 0.0 mol %, at most about 0.25 mol %, at most about 0.5 mol %, at most about 0.75 mol %, at most about 1.0 mol %, at most about 1.25 mol %, at most about 1.5 mol %, at most about 1.75 mol %, at most about 2.0 mol %, at most about 2.25 mol %, at most about 2.5 mol %, at most about 2.75 mol %, at most about 3.0 mol %, at most about 3.25 mol %, at most about 3.5 mol %, at most about 3.75 mol %, at most about 4.0 mol %, at most about 4.25 mol %, at most about 4.5 mol %, at most about 4.75 mol %, at most about 5.0 mol %, at most about 5.25 mol %, at most about 5.5 mol %, at most about 5.75 mol %, or at most about 6.0 mol %.

The systems and methods of the present disclosure can be carbon-efficient and/or energy-efficient. In some cases, the systems or methods of the present disclosure have a carbon efficiency of at least about 50%, at least about 55%, at least about 60%, at least about 65%, at least about 70%, at least about 75%, at least about 80%, at least about 85%, or at least about 90%. In some cases, a system of the present disclosure or method for use thereof has a ratio of all carbon atoms output from the system as hydrocarbons to all carbon atoms input to the system of at least about 0.4, at least about 0.50, at least about 0.55, at least about 0.60, at least about 0.65, at least about 0.70, at least about 0.75, at least about 0.80, at least about 0.85, at least about 0.90, or at least about 0.95.

In some cases, the systems or methods of the present disclosure have a carbon efficiency of between about 50% and about 85%, between about 55% and about 80%, between about 60% and about 80%, between about 65% and about 85%, between about 65% and about 80%, or between about 70% and about 80%. In some cases, a system of the present disclosure or method for use thereof has a ratio of all carbon atoms output from the system as hydrocarbons to all carbon atoms input to the system of between about 0.50 and about 0.85, between about 0.55 and about 0.80, between about 0.60 and about 0.80, between about 0.65 and about 0.85, between about 0.65 and about 0.80, or between about 0.70 and about 0.80.

In some instances, the carbon efficiency is at least about 50%, at least about 55%, at least about 60%, at least about 65%, at least about 70%, at least about 75%, at least about 80%, at least about 85% or at least about 90%. In some instances, the carbon efficiency is between about 50% and about 85%, between about 55% and about 80%, between about 60% and about 80%, between about 65% and about 85%, between about 65% and about 80%, or between about 70% and about 80%. In some instances, a system of the present disclosure or method for use thereof has a ratio of all carbon atoms output from the system as hydrocarbons to all carbon atoms input to the system of at least about 0.60, at least about 0.65, at least about 0.70, at least about 0.75, at least about 0.80, at least about 0.85 or at least about 0.90. In some instances, a system of the present disclosure or method for use thereof has a ratio of all carbon atoms output from the system as hydrocarbons to all carbon atoms input to the system of between about 0.50 and about 0.85, between about 0.55 and about 0.80, between about 0.60 and about 0.80, between about 0.65 and about 0.85, between about 0.65 and about 0.80, or between about 0.70 and about 0.80.

In some cases, the systems and methods combine OCM reaction, post-bed cracking (PBC), separations and methanation. The separations can include oligomerization of ethylene to $C_{3+}$ compounds, which are more easily separated as described in PCT Patent Application No. PCT/US2015/010525, which is incorporated herein by reference in its entirety. Additional details of OCM reactor and process design can be found in PCT Patent Application No. PCT/US2014/057465 and PCT Patent Application No. PCT/US2015/010688, each of which are incorporated herein by reference in their entirety.

In an aspect, provided herein is a method for performing oxidative coupling of methane (OCM). The method can comprise (a) reacting oxygen ($O_2$) with methane ($CH_4$) to form heat, ethylene ($C_2H_4$) and optionally ethane ($C_2H_6$), hydrogen ($H_2$), carbon monoxide (CO) or carbon dioxide ($CO_2$); (b) reacting the heat produced in (a) with ethane ($C_2H_6$) to form ethylene ($C_2H_4$) and hydrogen ($H_2$); (c) performing at least one of (i) enriching the ethylene ($C_2H_4$) produced in (a) and (b) or (ii) oligomerizing the ethylene ($C_2H_4$) produced in (a) and (b) to produce $C_{3+}$ compounds and enriching the $C_{3+}$ compounds; and (d) reacting the hydrogen ($H_2$) produced in (a) and (b) with carbon monoxide (CO) and/or carbon dioxide ($CO_2$) to form methane ($CH_4$).

In another aspect, provided herein is a system for performing oxidative coupling of methane (OCM). The system comprises an OCM reactor that reacts oxygen ($O_2$) with methane ($CH_4$) to form heat, ethylene ($C_2H_4$) and optionally ethane ($C_2H_6$), hydrogen ($H_2$), carbon monoxide (CO) or carbon dioxide ($CO_2$). The system further comprises a cracking vessel in fluid communication with the OCM reactor, which cracking vessel reacts the heat produced in the OCM reactor with ethane ($C_2H_6$) to form ethylene ($C_2H_4$) and hydrogen ($H_2$). The system further comprises a separations module in fluid communication with the cracking vessel, which separation module (i) enriches the ethylene ($C_2H_4$) produced in the OCM reactor and the cracking vessel or (ii) oligomerizes the ethylene ($C_2H_4$) produced in the OCM reactor and the cracking vessel to produce $C_{3+}$ compounds and enriches the $C_{3+}$ compounds. The system further comprises a methanation reactor in fluid communication with the separations module, which methanation reactor reacts the hydrogen ($H_2$) produced in the OCM reactor and the cracking vessel with carbon monoxide (CO) and/or carbon dioxide ($CO_2$) to form methane ($CH_4$).

In some cases, the ethane ($C_2H_6$) that is cracked in the cracking vessel was produced in the OCM reactor. In some instances, at least some of the ethane ($C_2H_6$) that is cracked is in addition to the ethane ($C_2H_6$) that was produced in the OCM reactor. In some cases, the OCM reactor produces ethane ($C_2H_6$), hydrogen ($H_2$), carbon monoxide (CO) and carbon dioxide ($CO_2$). In some cases, the carbon monoxide (CO) and carbon dioxide ($CO_2$) produced in the OCM reactor is methanated. The separations module can separate ethylene ($C_2H_4$) or $C_{3+}$ compounds from methane ($CH_4$), ethane ($C_2H_6$), hydrogen ($H_2$), carbon monoxide (CO) or carbon dioxide ($CO_2$). In some instances, the cracking vessel is a portion of the OCM reactor.

The methane formed in the methanation reactor can be returned to the OCM reactor or sold as sales gas. In some embodiments, the OCM reactor has an OCM catalyst. In some embodiments, the methanation reactor has a methanation catalyst. In some embodiments, the separations module comprises an ethylene-to-liquids (ETL) reactor comprising an oligomerization catalyst. At least some of the heat produced in the OCM reactor can be converted to power.

In another aspect, described herein is a method for producing $C_{2+}$ compounds from methane ($CH_4$). The method can comprise: (a) performing an oxidative coupling of methane (OCM) reaction which converts methane ($CH_4$) and oxygen ($O_2$) into ethylene ($C_2H_4$) and optionally ethane ($C_2H_6$); (b) optionally oligomerizing the ethylene ($C_2H_4$) to produce $C_{3+}$ compounds; and (c) isolating the $C_{2+}$ compounds, wherein the $C_{2+}$ compounds comprise the ethylene ($C_2H_4$), the ethane ($C_2H_6$) and/or the $C_{3+}$ compounds, where the method has a carbon efficiency of at least about 50%. In some cases, the isolated the $C_{2+}$ compounds are not pure. In some cases, the isolated the $C_{2+}$ compounds comprise methane, CO, $H_2$, $CO_2$ and/or water.

In some cases, the systems or methods of the present disclosure consume less than about 150, less than about 140, less than about 130, less than about 120, less than about 110, less than about 100, less than about 95, less than about 90, less than about 85, less than about 80, less than about 75, less than about 70, less than about 65, less than about 60, less than about 55, or less than about 50 million British Thermal Units (MMBtu) of energy per ton of ethylene ($C_2H_4$) or $C_{3+}$ compounds enriched. In some cases, the amount of energy consumed by the system includes the energy content of the feedstock used to make the ethylene ($C_2H_4$) or $C_{3+}$ compounds.

In some cases, the systems or methods of the present disclosure have consume between about 65 and about 100, between about 70 and about 110, between about 75 and about 120, between about 85 and about 130, between about 40 and about 80, or between about 50 and about 80 MMBtu of energy per ton of ethylene ($C_2H_4$) or $C_{3+}$ compounds enriched. In some cases, the amount of energy consumed by the system includes the energy content of the feedstock used to make the ethylene ($C_2H_4$) or $C_{3+}$ compounds.

In some embodiments, the systems or methods of the present disclosure have a specific oxygen consumption of about 1.2, about 1.3, about 1.4, about 1.5, about 1.6, about 1.7, about 1.8, about 1.9, about 2.0, about 2.1, about 2.2, about 2.3, about 2.4, about 2.5, about 2.6 about 2.7, about 2.8, about 2.9, about 3, about 3.2, about 3.4, about 3.6, about 3.8, or about 4.0.

In some embodiments, the systems or methods of the present disclosure have a specific oxygen consumption of between about 1.2 and about 2.7, between about 1.5 and about 2.5, between about 1.7 and about 2.3 or between about 1.9 and about 2.1.

In some embodiments, the systems or methods of the present disclosure have a specific $CO_2$ emission of about 0.5, about 0.6, about 0.7, about 0.8, about 0.9, about 1.0, about 1.1, about 1.2, about 1.3, about 1.4, about 1.5, about 1.6, about 2.0, about 2.2, about 2.4, about 2.6, about 2.8, about 3.0, about 3.2, about 3.4, or about 3.6.

In some embodiments, the systems or methods of the present disclosure have a specific $CO_2$ emission of between about 0.5 and about 1.7, between about 0.7 and about 1.4, between about 0.8 and about 1.3 or between about 0.9 and about 1.1.

In some embodiments, the systems or methods of the present disclosure produces $C_{2+}$ products, and the $C_{2+}$ products comprise at least about 2.5%, at least about 2.5%, at least about 5%, at least about 7.5%, at least about 10%, at least about 12.5% or at least about 15% $C_{3+}$ hydrocarbons.

In some embodiments, the systems or methods of the present disclosure produces $C_2$ products and $C_{3+}$ products, and the ratio of the $C_2$ products to the $C_{3+}$ products is about 20, about 15, about 10, about 8, about 6 or about 5.

In some embodiments, the systems or methods of the present disclosure produces $C_2$ products and $C_{3+}$ products, and the ratio of the $C_2$ products to the $C_{3+}$ products is between about 5 and about 20, between about 6 and about 10, or between about 8 and about 10.

In another aspect, provided herein is a method for producing $C_{2+}$ compounds from methane ($CH_4$), the method comprising: (a) performing an oxidative coupling of methane (OCM) reaction which converts methane ($CH_4$) and oxygen ($O_2$) into ethylene ($C_2H_4$) and optionally ethane ($C_2H_6$); (b) optionally oligomerizing the ethylene ($C_2H_6$) to produce $C_{3+}$ compounds; and (c) isolating the $C_{2+}$ compounds, wherein the $C_{2+}$ compounds comprise the ethylene ($C_2H_4$), the ethane ($C_2H_6$) and/or the $C_{3+}$ compounds, where the method consumes less than about 100 MMBtu of energy per ton of the $C_{2+}$ compounds isolated. In some cases, the amount of energy consumed by the system includes the energy content of the feedstock used to make the isolated $C_{2+}$ compounds. In some cases, the isolated the $C_{2+}$ compounds are not pure. In some cases, the isolated the $C_{2+}$ compounds comprise methane, CO, Hz, $CO_2$ and/or water.

In some cases, the method consumes less than about 150, less than about 140, less than about 130, less than about 120, less than about 110, less than about 100, less than about 95, less than about 90, less than about 85, less than about 80, less than about 75, less than about 70, less than about 65, less than about 60, less than about 55, or less than about 50 MMBtu of energy per ton of $C_{2+}$ compounds isolated. In some cases, the method consumes between about 65 and about 100, between about 70 and about 110, between about 75 and about 120, between about 85 and about 130, between about 40 and about 80, or between about 50 and about 80 MMBtu of energy per ton of $C_{2+}$ compounds isolated.

In another aspect, provided herein is a method for producing $C_{2+}$ compounds from methane ($CH_4$), the method comprising performing an oxidative coupling of methane (OCM) reaction using an OCM catalyst at a set of reaction conditions to convert a quantity of methane ($CH_4$) into ethylene ($C_2H_4$) at a carbon efficiency, where the OCM catalyst has a $C_{2+}$ selectivity at the set of reaction conditions that is less than the carbon efficiency at the set of reaction conditions. The set of reaction conditions can include a temperature, a pressure, a methane to oxygen ratio and a gas hourly space velocity (GHSV).

In another aspect, provided herein is a method for producing $C_{2+}$ compounds from methane ($CH_4$), the method comprising: (a) performing an oxidative coupling of methane (OCM) reaction using an OCM catalyst at a set of reaction conditions to convert a quantity of methane ($CH_4$) into ethylene ($C_2H_4$) and ethane ($C_2H_6$); and (b) cracking the ethane ($C_2H_6$) to produce additional ethylene ($C_2H_4$), where the combined carbon efficiency of (a) and (b) is greater than the $C_{2+}$ selectivity of the OCM catalyst at the set of reaction conditions. The set of reaction conditions can include a temperature, a pressure, a methane to oxygen ratio and a gas hourly space velocity (GHSV).

In some instances, the $C_{2+}$ selectivity is at most about 70%, at most about 65%, at most about 60%, at most about 55%, at most about 50%, at most about 45%, at most about 40%, or at most about 35%. In some instances, the $C_{2+}$ selectivity is at least about 70%, at least about 65%, at least about 60%, at least about 55%, at least about 50%, at least about 45%, at least about 40%, or at least about 35%.

In another aspect, provided herein is a method for producing $C_{2+}$ compounds, the method comprising: (a) providing a first feedstock comprising methane ($CH_4$) and optionally a first amount of ethane ($C_2H_6$); (b) performing an OCM reaction on the first feedstock to produce an OCM product comprising a first amount of ethylene ($C_2H_4$); (c) combining the OCM product with a second feedstock comprising a second amount of ethane ($C_2H_6$) to produce a third feedstock; and (d) cracking the third feedstock to produce a second amount of ethylene ($C_2H_4$), where the second amount of ethylene includes ethylene produced in (b) and (d).

In some cases, the fraction of the second amount of ethylene ($C_2H_4$) that is derived from the first or the second amounts of ethane ($C_2H_6$) is at least about 1%, at least about 3%, at least about 5%, at least about 7%, at least about 10%, at least about 15%, at least about 20%, at least about 25%, at least about 30%, at least about 35%, at least about 40%, at least about 45%, at least about 50%, or at least about 55%.

In some cases, the combined moles of the first amount and second amount of ethane ($C_2H_6$) divided by the combined moles of the first feedstock and the second feedstock is about 1%, about 3%, about 5%, about 7%, about 10%, about 15%, about 20%, about 25%, about 30%, about 35%, about 40%, about 45%, about 50%, about 55%, or about 60%.

In some cases, the combined moles of the first amount and second amount of ethane ($C_2H_6$) divided by the combined moles of the first feedstock and the second feedstock is between about 1% and about 50%, between about 1% and about 40%, between about 1% and about 30%, between about 1% and about 20%, between about 1% and about 15%, between about 1% and about 10%, or between about 10% and about 50%.

In some cases, the first feedstock is natural gas. In some cases, the first feedstock is natural gas supplemented with the first amount of ethane ($C_2H_6$). In some cases, the first feedstock is natural gas having passed through a separations system to substantially remove the hydrocarbons other than methane.

In some cases, the molar percent of ethane ($C_2H_6$) in methane ($CH_4$) in the first feedstock is about 1%, about 3%, about 5%, about 7%, about 10%, about 15% or about 20%.

In some cases, some or all of a methane-containing feed stream (e.g., natural gas) can be processed in a separation system prior to being directed into an OCM reactor. Directing a methane-containing feed stream into an OCM reactor via a separation system or subsystem rather than into an OCM reactor directly can provide advantages, including but not limited to increasing the carbon efficiency of the process, optimizing the OCM process for methane processing, and optimizing the post-bed cracking (PBC) process for ethane processing. Such a configuration can result in higher back-end sizing for the system; however, in some cases (e.g., when using high pressure pipeline natural gas as a feedstock, high recycle ratio), the back-end sizing increase can be reduced or moderated. The separation system or subsystem can comprise a variety of operations including any discussed in the present disclosure, such as $CO_2$ removal via an amine system, caustic wash, dryers, de-methanizers, de-ethanizers, and $C_2$ splitters. In some cases, all of the methane and ethane in the methane-containing feed stream (e.g., natural gas) passes through a separations system or separations subsystem prior to passing through an OCM reactor. Some or all of the ethane from the feed stream can be directed from the separation system or subsystem into the inlet of an OCM reactor or into a post-bed cracking (PBC) unit.

Figure 1C:
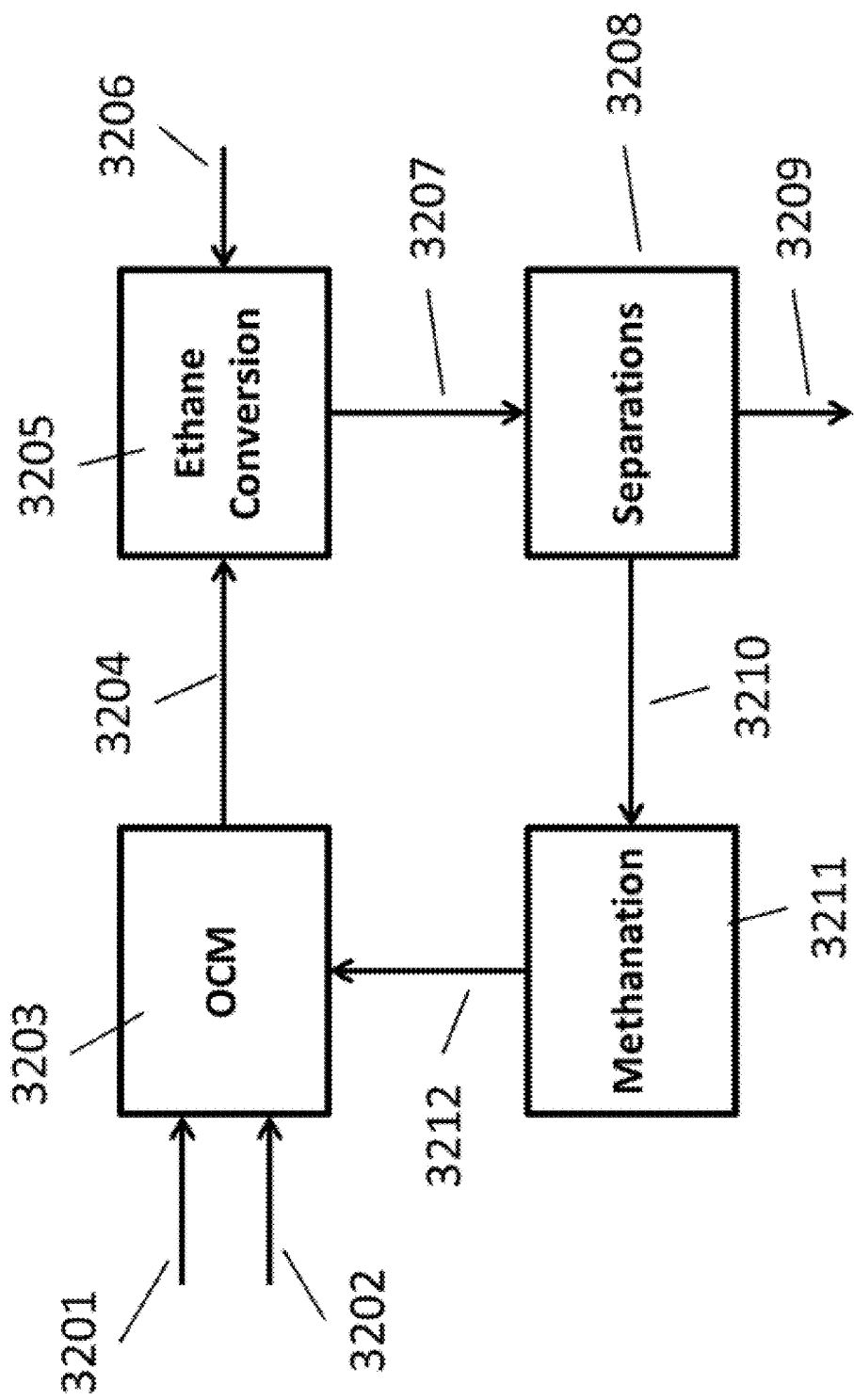
FIG. 1C shows a block flow diagram of an OCM process that includes ethane conversion, separations and methanation.

In some configurations, an OCM system can be operated in a cycle, with at least some of the products from one unit or subsystem being processed or reacted in the next unit or subsystem (see, e.g., FIG. 1C). For example, oxygen ($O_2$) 3201 and methane ($CH_4$) feed 3202 can be provided to an OCM reactor 3203, which produces an OCM product stream 3204 comprising ethane ($C_2H_6$), ethylene ($C_2H_4$), carbon monoxide (CO) and/or carbon dioxide ($CO_2$), and heat. The OCM product stream can then be fed into an ethane conversion subsystem 3205 (e.g., a cracking vessel or an ethane cracker) in fluid communication with the OCM reactor. The ethane conversion subsystem can also receive an additional $C_2H_6$ stream 3206. The ethane conversion subsystem can convert $C_2H_6$ (e.g., crack $C_2H_6$ to $C_2H_4$) with the aid of the heat liberated by the OCM reaction; this heat can also be used to crack the $C_2H_6$ in the additional $C_2H_6$ stream. A $C_2H_4$ product stream 3207 can then be directed from the ethane conversion subsystem into a separations module 3208 in fluid communication with the ethane conversion subsystem. The separations module can enrich products such as $C_2H_4$ in the product stream. The separations module can also oligomerize $C_2H_4$ to form compounds comprising three or more carbon atoms ($C_{3+}$ compounds). An enriched product stream 3209 enriched in $C_2H_4$ and/or $C_{3+}$ compounds can be recovered from the separations module. A lights stream 3210 comprising components such as hydrogen ($H_2$) (e.g., hydrogen generated from the cracking of $C_2H_6$) and CO and/or $CO_2$ can be recovered from the separations module and directed into a methanation reactor 3211 in fluid communication with the separations module. The methanation reactor can react $H_2$ with CO and/or $CO_2$ to form a methanated stream 3212 comprising $CH_4$. The methanated stream can then be directed into the OCM reactor to provide additional methane for the OCM process. In some cases, energy generated in the methane conversion section in the form of high pressure steam, high temperature steam, heat, electricity, heat transferred via gas-gas heat exchanger, heat transferred via gas-liquid heat exchanger, or other forms, can be used to provide all of the energy and power required to run the entire plant or system. In some cases, a cyclical system or process can operate with a carbon efficiency such as those discussed in this disclosure. For example, such a system or process can operate with a carbon efficiency of at least about 50%, at least about 55%, at least about 60%, at least about 65%, at least about 70%, at least about 75%, at least about 80%, at least about 85%, or at least about 90%. In some cases, such a system or process can operate with a carbon efficiency of between about 50% and about 85%, between about 55% and about 80%, between about 60% and about 80%, between about 65% and about 85%, between about 65% and about 80%, or between about 70% and about 80%. In some cases, such a system or process (or method) can operate such that a ratio of all carbon atoms output from the system as hydrocarbons to all carbon atoms input to the system is at least about 0.50, at least about 0.55, at least about 0.60, at least about 0.65, at least about 0.70, at least about 0.75, at least about 0.80, at least about 0.85, or at least about 0.90. In some cases, such a system or process can operate such that a ratio of all carbon atoms output from the system as hydrocarbons to all carbon atoms input to the system is between about 0.50 and about 0.85, between about 0.55 and about 0.80, between about 0.60 and about 0.80, between about 0.65 and about 0.85, between about 0.65 and about 0.80, or between about 0.70 and about 0.80.

Figure 1D:
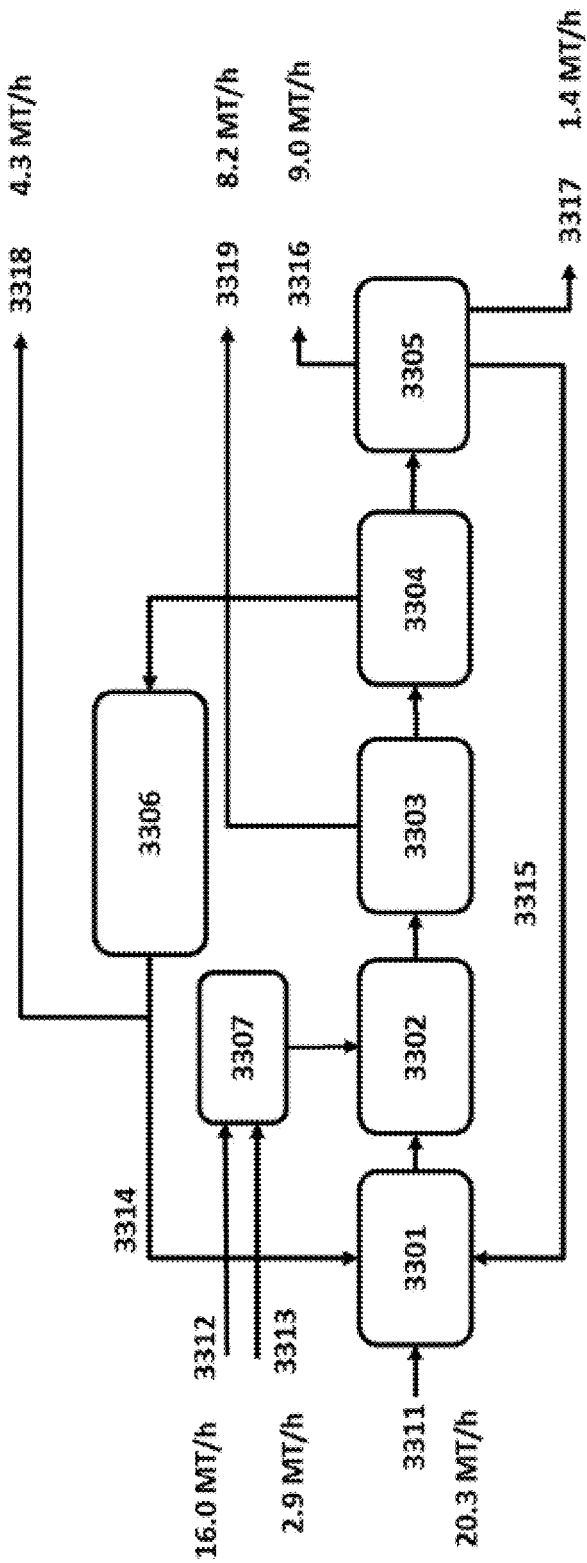
FIG. 1D shows a process block flow diagram with feeds and products.
Figure 1E:
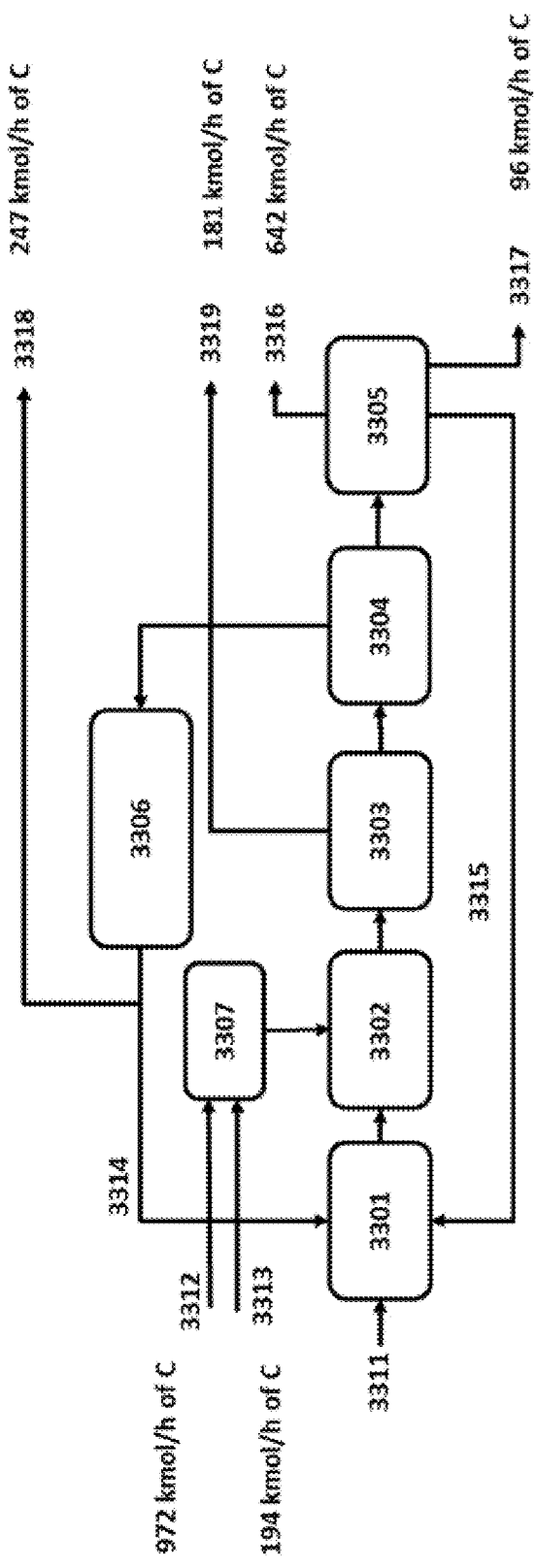
FIG. 1E shows a process block flow diagram with carbon utilization.

FIG. 1D and FIG. 1E show an exemplary process comprising an OCM unit 3301, a process gas compressor 3302, a process gas cleanup unit 3303, a cryogenic separations unit 3304, a fractionation unit 3305, a methanation unit 3306, and a sulfur-removal unit 3307. An oxygen stream 3311 is fed into the OCM unit, along with a $C_1$ recycle stream 3314 from the methanation unit and a $C_2$ recycle stream 3315 from the fractionation unit. A natural gas stream 3312 and an ethane stream 3313 are fed into the sulfur removal unit. Output from the OCM unit and the sulfur removal unit are directed into the process gas compressor, and then into the process gas cleanup unit, which removes a $CO_2$ stream 3319. The remaining product stream is directed into the cryogenic separations unit, where light components including $H_2$ and CO or $CO_2$ are directed into the methanation unit, and the remaining product stream, including ethylene and other $C_{2+}$ compounds, is directed into the fractionation unit. The fractionation unit separates an ethylene stream 3316 and a $C_{3+}$ compound stream 3317 comprising $C_3$ compounds, $C_4$ compounds, and $C_{5+}$ compounds, as well as the $C_2$ recycle 3315 which is directed back to the OCM unit. The methanation unit converts the light components into methane, a first portion of which is recycled 3314 to the OCM unit and a second portion of which is output as sales gas 3318. The operating flow rates for the input streams are as follows: 20.3 MT/h of oxygen 3311, 16.0 MT/h of natural gas 3312, and 2.9 MT/h of ethane 3313. The operating flow rates for the output streams are as follows: 9.0 MT/h of ethylene 3316, 1.4 MT/h of $C_{3+}$ compounds 3317, 4.3 MT/h of sales gas 3318, and 8.2 MT/h of $CO_2$ 3319. The corresponding carbon content of the input streams are 972 kmol/h of carbon in the natural gas stream 3312, and 194 kmol/h of carbon in the ethane stream 3313. The corresponding carbon content of the output streams are 642 kmol/h of carbon in the ethylene stream 3316, 96 kmol/h of carbon in the $C_{3+}$ compounds stream 3317, 247 kmol/h of carbon in the sales gas stream 3318, and 181 kmol/h of carbon in the $CO_2$ stream 3319. Therefore, the amount of carbon input to the system is 1166 kmol/h, and the amount of carbon output from the system in hydrocarbon products (e.g., excluding $CO_2$) is 985 kmol/h, for a resulting carbon efficiency of 84.5%.

Reaction heat (e.g., OCM reaction heat) can be used to supply some, most, or all of the energy used to operate systems and perform processes of the present disclosure. In some examples, reaction heat can be used to supply at least about 50%, 55%, 60%, 65%, 70%, 75%, 80%, 85%, 90%, 95%, 96%, 97%, 98%, 99%, or 100% of energy for operating systems and performing processes of the present disclosure. For example, the reaction heat can be used to supply at least about 80% or 90% of all of the energy for operating systems or processes of the present disclosure. This can provide for an efficient, substantially self-contained system with reduced or even minimum external energy input.

Integration of OCM Processes with Other Chemical Processes

There exists an infrastructure for chemical production throughout the world. This infrastructure is deployed on virtually every continent, addresses wide ranging industries, and employs a wide variety of different implementations of similar or widely differing technologies.

The present disclosure provides systems and methods for integrating OCM systems and methods with various chemical processes, such as methanol (MeOH) production, chlorine ($Cl_2$) and sodium hydroxide (NaOH) production (e.g., chloralkali process), vinylchloride monomer (VCM) production, ammonia ($NH_3$) production, processes having syngas (e.g., mixtures of hydrogen ($H_2$) and carbon monoxide (CO) in any proportion), or olefin derivative production.

As will be appreciated, the capital costs associated with each of the facility types described above can run from tens of millions to hundreds of millions of dollars each. Additionally, there are inputs and outputs, of these facilities, in terms of both energy and materials, which have additional costs associated with them, both financial and otherwise that may be further optimized in terms of cost and efficiency. Further, because different facilities tend to be optimized for the particularities (e.g., products, processing conditions) of the market in which they exist, they tend to be operated in an inflexible manner, in some cases without the flexibility or option to optimize for their given market. The present inventors have recognized surprising synergies when integrating OCM with the aforementioned chemical processes which can result in improved economics and/or operational flexibility.

In some cases, the OCM processes described herein are integrated with an olefin oligomerization process, such as an ethylene-to-liquids ("ETL") process as described in U.S. patent Ser. Nos. 14/099,614, and 14/591,850, the full disclosures of each of which are incorporated herein by reference in its entirety for all purposes.

In some instances, the OCM process can be sized to fit the needs of an ethylene derivatives plant. Such a synergy can liberate the derivatives producer from being a merchant buyer of ethylene, allowing the producer more ethylene cost and supply certainty. Examples of ethylene derivatives include polyethylene, including low-density polyethylene (LDPE), linear low-density polyethylene (LLDPE), and high-density polyethylene (HDPE). Additional ethylene derivatives include ethylbenzene, styrene, acetic acid, vinylacetate monomer, ethylene dichloride, vinylchloride monomer, ethylene oxide and alpha olefins.

Integration of OCM Processes with Methanol Processes

The OCM processes can be integrated with methanol production processes to realize unexpected synergies potentially including, but not limited to (a) additional methanol capacity with minimal or no modification to the methanol plant and (b) additional ethylene capacity with low investment and environmental footprint.

Figure 3:
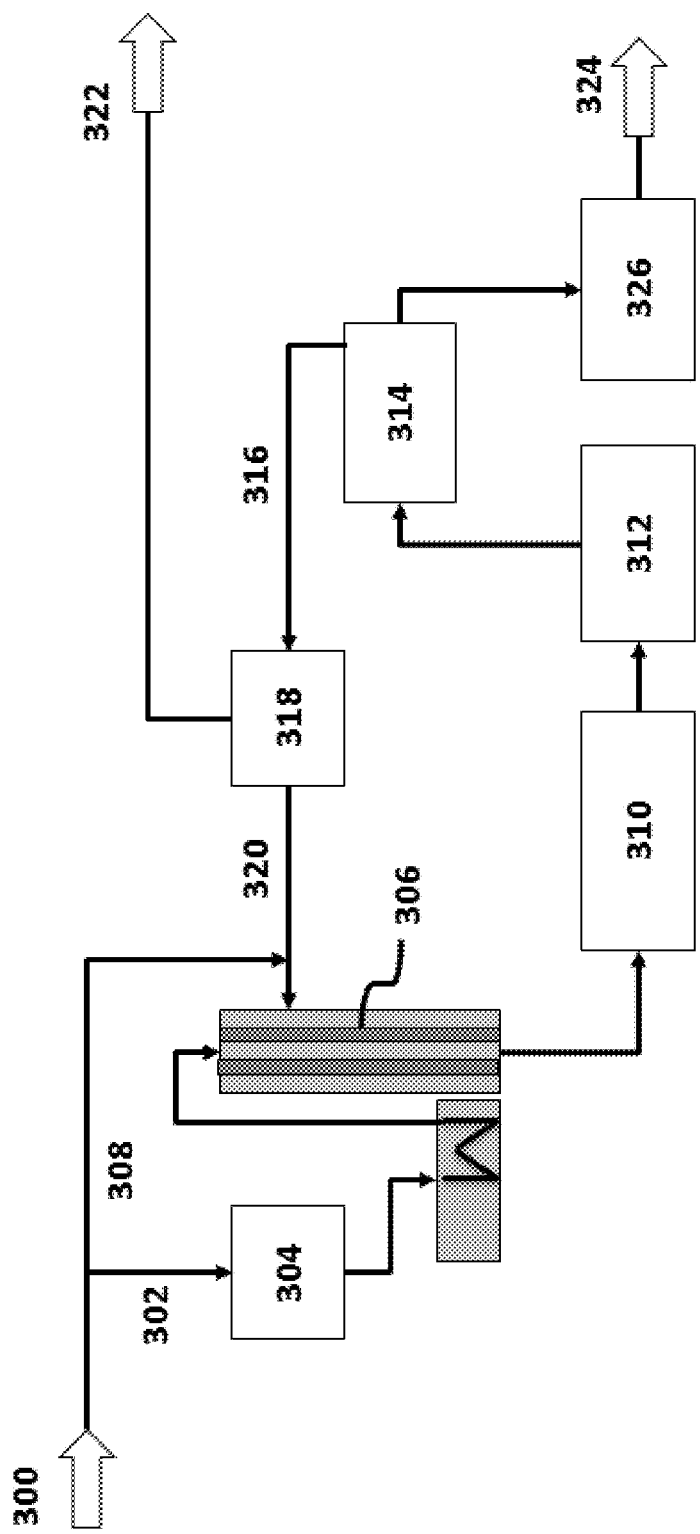
FIG. 3 is a schematic illustration of a methanol production process.

FIG. 3 shows an example of a block flow diagram of a methanol plant (e.g., a traditional methanol process, recognizing that alternate embodiments are allowed and details have been emitted for clarity). As shown, natural gas 300 can be used for feed and fuel for the process. The feed 302 (e.g., natural gas providing the carbon atoms for the methanol product) can have sulfur-containing compounds removed in a de-sulfurization module 304 before being fed into a steam methane reformer (SMR, entire gray shaded unit) 306. The SMR can also accept natural gas as fuel 308 (e.g., natural gas providing energy for the methanol plant), which does not necessarily have to be de-sulfurized. The effluent of the steam methane reformer is syngas, which can have heat recovered in a heat recovery module 310 and compressed in a compression module 312. Compressed syngas can be feed into the synthesis module 314 where conversion to methanol occurs. One suitable methanol synthesis module can have a catalyst that is a mixture of copper, zinc, and alumina, and operates at a pressure between about 50 and about 100 atmospheres and a temperature of about 250° C. The production of syngas produces 3 moles of $H_2$ per mol of $CH_4$, while the stoichiometry of methanol formation from syngas consumes only 2 moles of $H_2$. Thus, excess $H_2$ (and un-reacted $CH_4$) can be purged 316 from the synthesis module and separated in a gas separation module 318 (e.g., a pressure swing adsorber). The separation module can produce additional fuel 320 for the SMR and a $H_2$ co-product 322. The methanol product 324 can be enriched (e.g., by a distillation module 326). In some cases, the excess $H_2$ is used as fuel (not shown).

Figure 4:
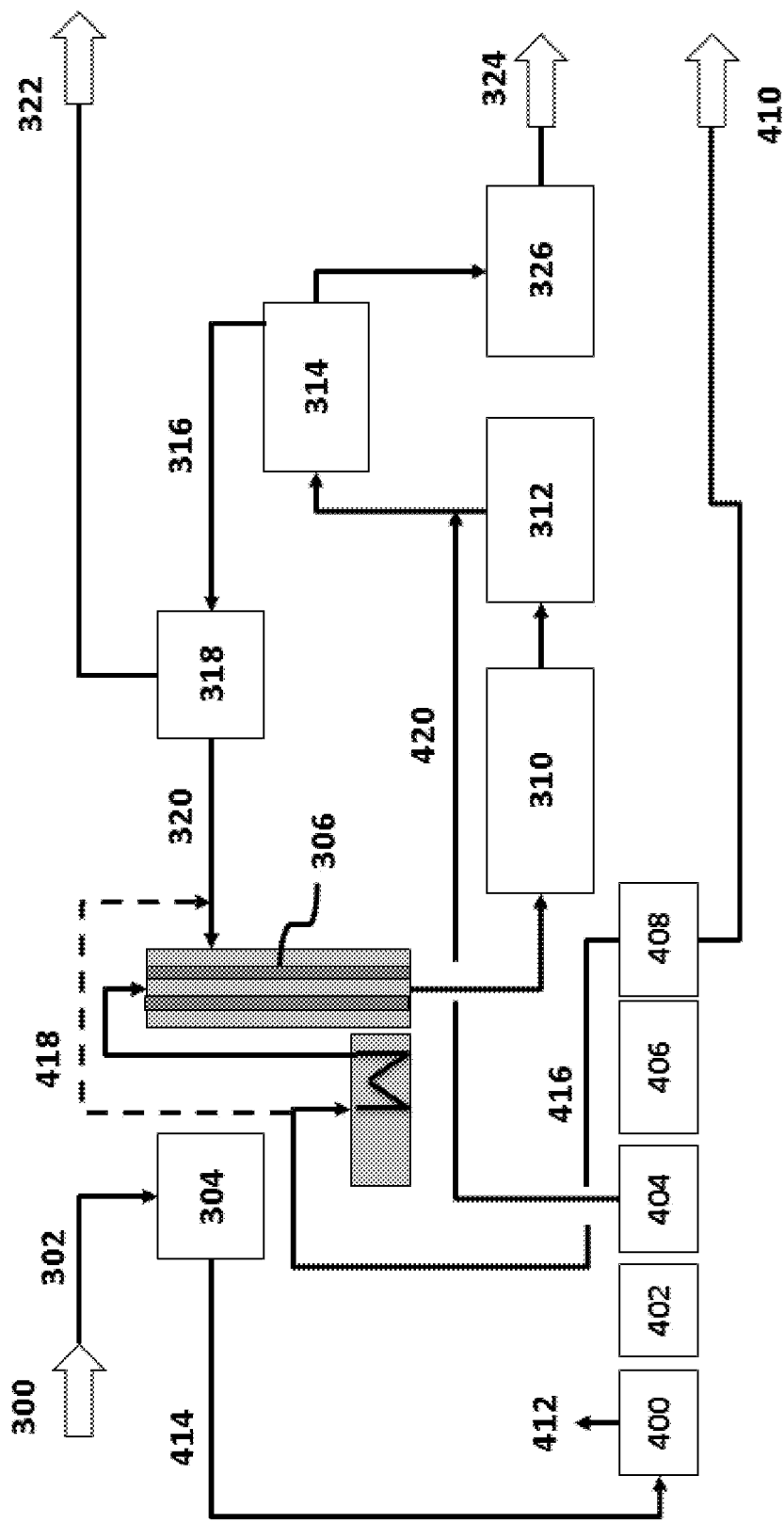
FIG. 4 is a schematic illustration of OCM integrated with a methanol production process.

A combined process that integrates OCM with methanol production is shown in FIG. 4, where like numerals represent like elements. The OCM portion of the combined process can accept the de-sulfurized natural gas feedstock 414 and include an OCM reaction module 400, a process gas compression module 402, a $CO_2$ removal module (e.g., process gas cleanup) 404, a drying module 406 and a separations module (e.g., a cryogenic de-methanizer) 408. In some cases, the separation module produces the $C_{2+}$ compounds 410. The $C_{2+}$ compounds can be further refined, and/or sent to a cracker (e.g., to the separation section of a cracker). Note that the OCM process does not require a methanation module. The OCM reaction can produce high-pressure super-heated (HPSH) steam 412 that can be used in the process and/or to produce power using a steam turbine.

Continuing with FIG. 4, the OCM portion of the process can produce a stream of methane that was not converted to $C_{2+}$ compounds 416 in the OCM reaction. This stream 416 can have $H_2$ and CO in addition to methane and can be used as the feed to the methanol production process (e.g., at the SMR) and/or as fuel to the process (dashed line) 418. The stream of $CO_2$ 420 from the OCM process can also be used in the methanol synthesis module 314 to produce one mole of methanol and one mole of water from one mole of $CO_2$ and 3 moles of $H_2$. The water co-product can be removed in the distillation module 326.

The combined OCM-methanol process has considerable economic and environmental benefits. In some cases, $CO_2$ from OCM 420 can be used to re-balance the make-up gas to the synthesis module and convert some or all of the excess $H_2$ to methanol (e.g., the flow-rate of stream 322 can be zero or very small in comparison to the flow rate without OCM integration). Furthermore, the reformer 306 capacity can be automatically increased due to the "pre-formed" nature of the OCM de-methanizer overhead 416 stream (e.g., already contains some $H_2$ and CO). This can be useful for replacing a mixed feed coil. In some instances, the only cost associated with the production of extra methanol due to OCM integration is the loss in value of the $H_2$ co-product 322 in situations where that stream is actually monetized or monetizable. Such integration schemes can result in improved efficiency of an existing methanol system, for example by using excess $H_2$ by reacting it with $CO_2$ produced from an OCM unit to produce a more valuable methanol product. Depending on the capacity of the OCM process, an integrated OCM-methanol system can be pushed to a low emission, high carbon efficiency process.

When retrofitting an existing methanol plant, the OCM process can be sized to the desired amount of extra methanol production. From the OCM perspective, building an OCM process to be integrated with a methanol plant can require significantly less capital than building a stand-alone OCM process, e.g., due to reducing or eliminating the need for fractionation and methanation equipment. The OCM process can also use the utilities of the existing methanol plants, such as steam. In some cases, the combined process produces zero or a minimal amount of $NO_x$ and $SO_x$ compounds.

The combined OCM-methanol process can be about 100% carbon efficient (e.g., with reference to FIG. 4, all of the carbon atoms input to the process 300 end up in the methanol 324 or the $C_{2+}$ compounds 410). In some cases, the combined process is less than 100% carbon efficient, e.g., greater than or equal to about 99%, greater than or equal to about 98%, greater than or equal to about 97%, greater than or equal to about 96%, greater than or equal to about 95%, greater than or equal to about 93%, greater than or equal to about 90%, greater than or equal to about 85%, greater than or equal to about 80%, or greater than or equal to about 75% carbon efficient.

Figure 5:
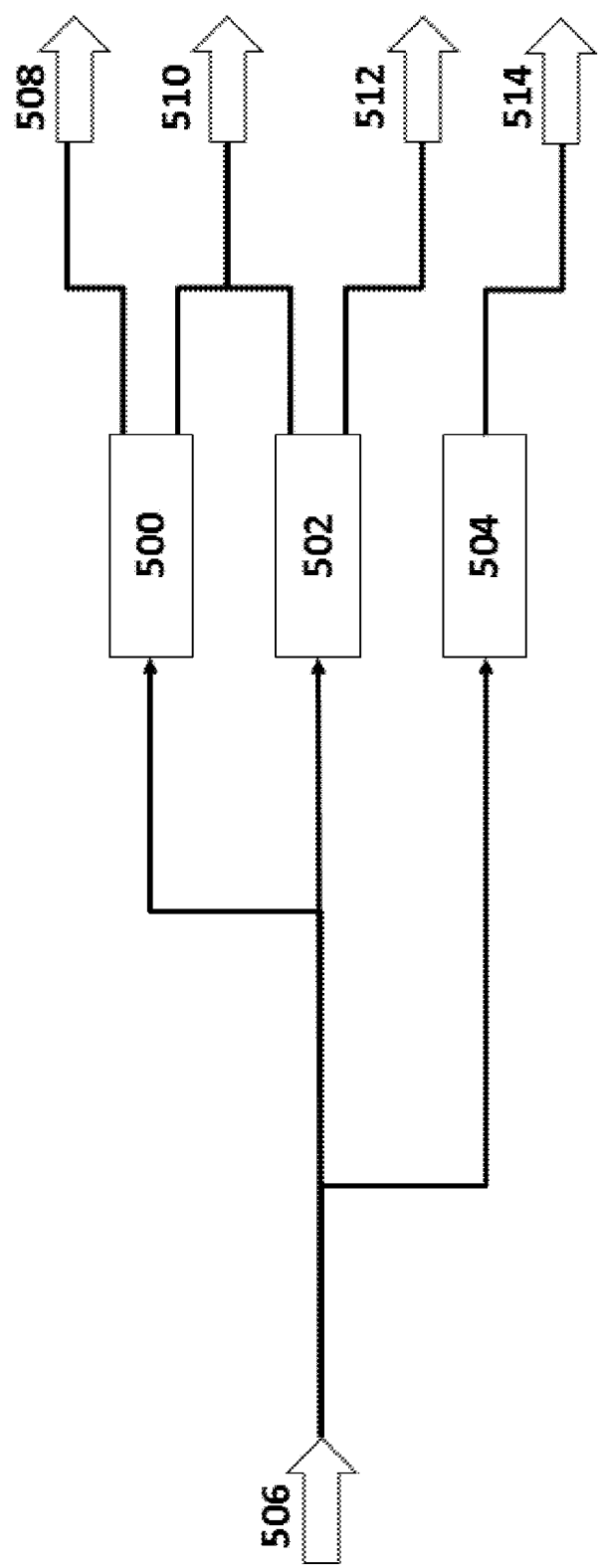
FIG. 5 is a schematic illustration of a petrochemical complex with a methanol production process and a cracker.

In some cases, with reference to FIG. 5, methanol plants 500 are located in proximity to crackers 502 and/or other processes 504 that use natural gas (e.g., within 1, 5, 10, 20, 50, 100, 200 miles or more). In some cases, these processes share a piping infrastructure and/or can access a piping infrastructure for transporting natural gas, ethylene, hydrogen and other chemicals. These processes can convert the natural gas 506 into a combination of methanol 508, hydrogen 510, ethylene 512, and other products 514. OCM can be integrated with any combination of these processes (e.g., 500, 502 and 504) in a number of ways as shown in FIG. 6, FIG. 7 and FIG. 8.

Figure 6:
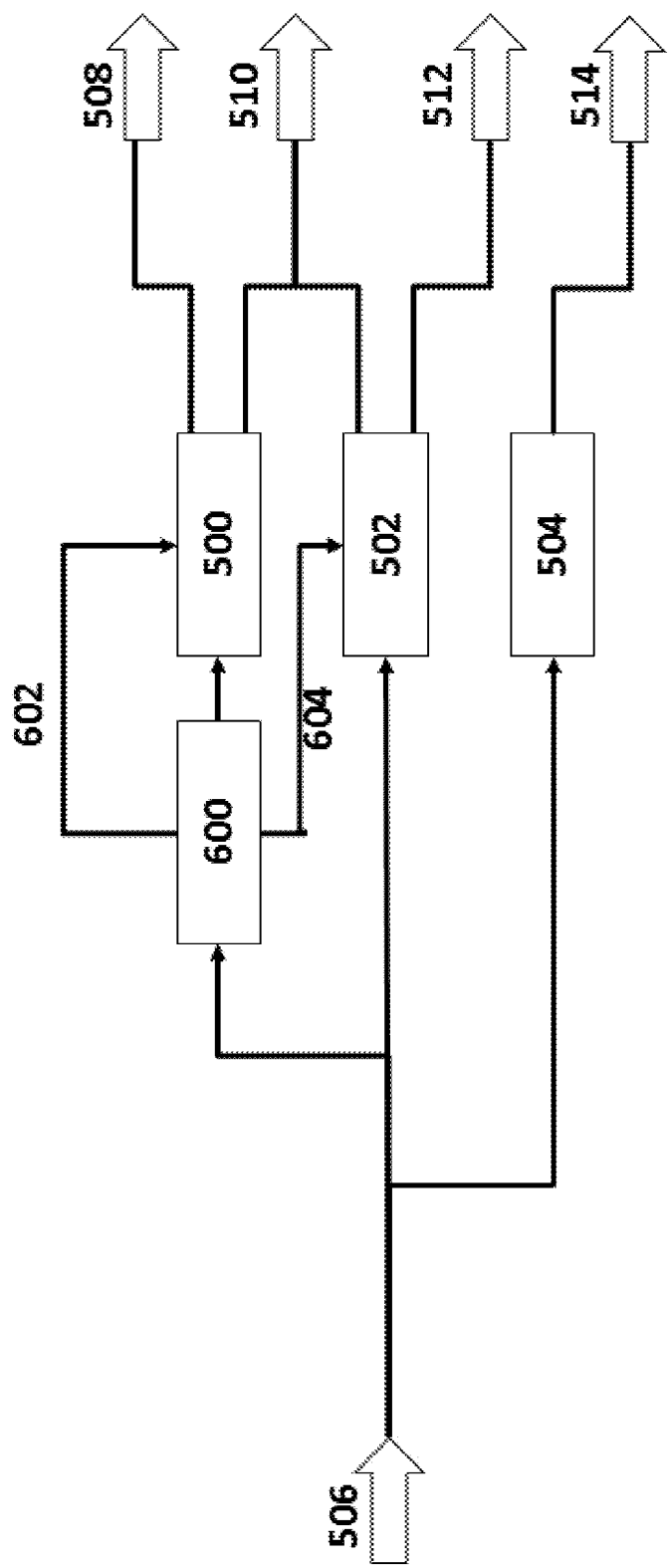
FIG. 6 is a schematic illustration of the integration of OCM with a methanol production process and a cracker.

FIG. 6 shows a "minimum revamp case" where an OCM process 600 accepts natural gas 506 and provides $CO_2$ 602 to a methanol process 500 and crude ethylene 604 to a cracker 502. The ethylene can be refined to a finished product (e.g., polymer grade ethylene) 512 using the fractionation capacity of the cracker. In this case, the OCM process can be sized to accept an amount of natural gas that is substantially equivalent to the methanol plant natural gas input (e.g., about 60 to 70 MMSCFD). This OCM capacity can result in about 25-30 kTa additional ethylene and about 15% to 20% additional methanol produced. In some cases, for the minimum revamp case, the only capital investment is for the OCM unit 600 and in some cases mixed feed coil replacement in the SMR.

Figure 7:
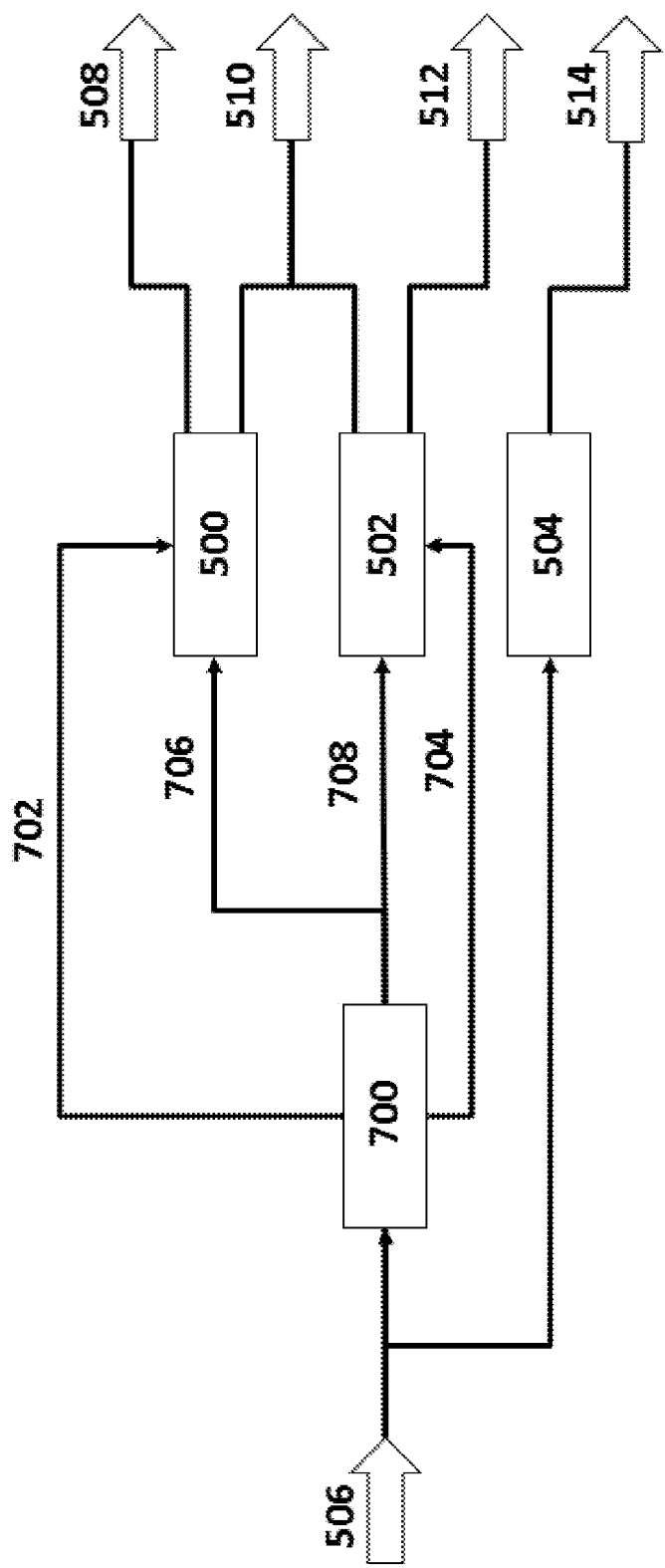
FIG. 7 is a schematic illustration of the integration of OCM with a methanol production process and a cracker.

FIG. 7 shows a "medium revamp case" where an OCM process 700 accepts natural gas 506 and provides $CO_2$ 702 to a methanol process 500 and crude ethylene 704 to a cracker 502. In this case, the OCM process can be sized to accept an amount of natural gas that is substantially equivalent to the methanol plant natural gas input 706 and cracker fuel input 708 (e.g., about 140 to 150 MMSCFD). This OCM capacity can result in about 60-80 kTa additional ethylene and about 30% to 40% additional methanol produced. In some cases, for the medium revamp case, capital investment is needed for the OCM unit 700 and methanol debottlenecking (e.g., reformer, syngas compressor, synthesis module and topping column).

Figure 8:
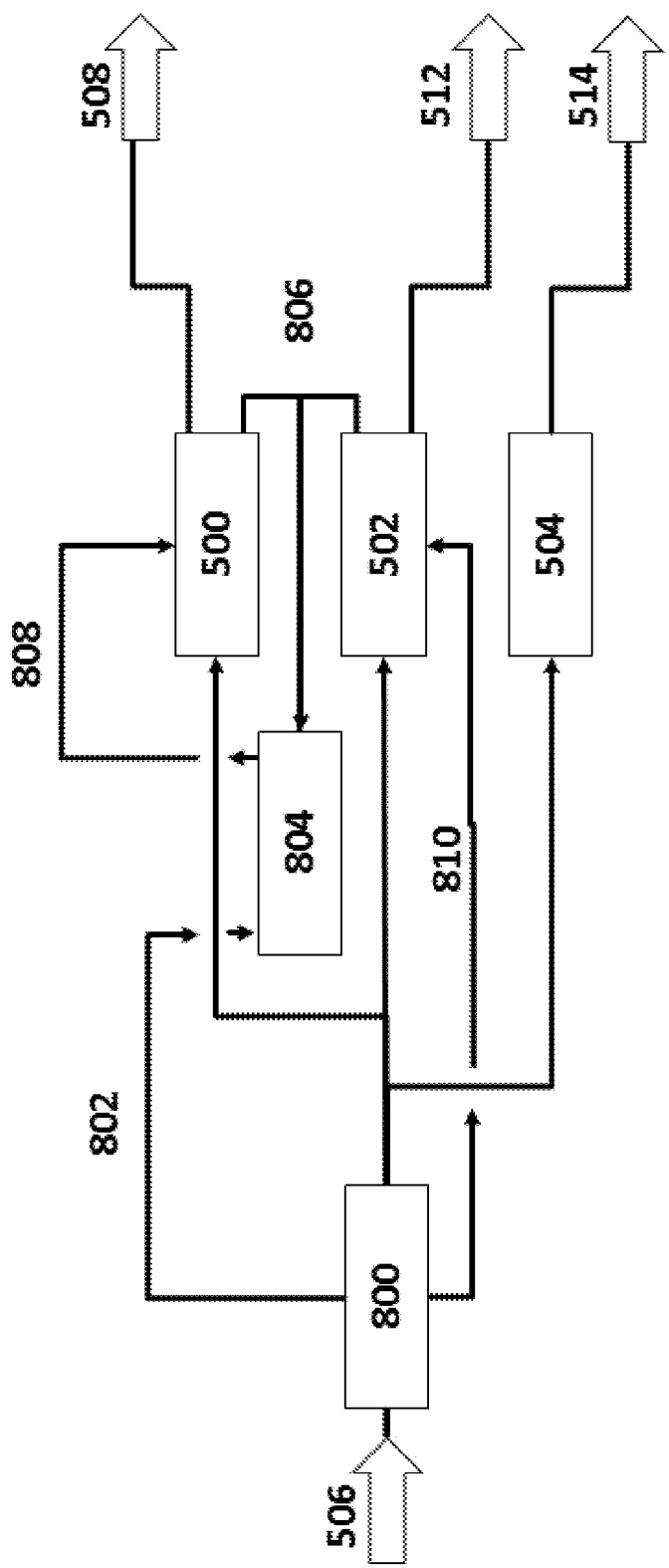
FIG. 8 is a schematic illustration of the integration of OCM with a methanol production process and a cracker.

FIG. 8 shows a "maximum efficiency revamp case" where the size of the OCM process is not constrained. For example, all of the natural gas entering an entire petrochemical complex can be skimmed. An OCM process 800 accepts natural gas 506 and provides $CO_2$ 802 to a new methanol synthesis module 804. In some cases, the new methanol synthesis module 804 accepts $H_2$ 806 from various sources including an existing methanol process 500 and/or a cracker 502. The new methanol synthesis module 804 can provide crude methanol 808 to the existing methanol process for refining to a methanol product 508. As in the other revamp scenarios, crude ethylene 810 can be refined in a cracker 502. In some cases, the OCM results in about 150-200 kTa additional ethylene, the integration results in about 60% to 70% additional methanol produced. In some cases, for the maximum efficiency revamp case, capital investment is needed for the OCM unit, a new methanol synthesis module (fed with the excess $H_2$ across the entire complex and $CO_2$ from OCM) and in some cases debottlenecking of methanol distillation. The various revamp cases are not mutually exclusive and can be designed as successive project phases. In addition, larger capacity plants can be combined with larger methanol production plants.

Integration of OCM Processes with Chloralkali Processes

Figure 9:
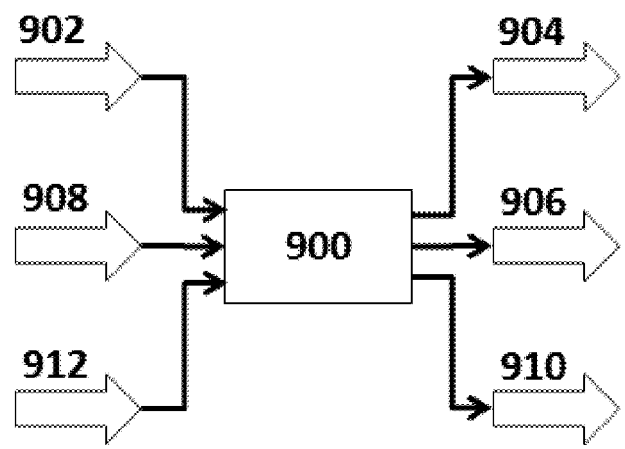
FIG. 9 is a schematic illustration of a chloralkali process.

With reference to FIG. 9, the chloralkali process 900 is an industrial process for the electrolysis of sodium chloride (NaCl) 902 to produce chlorine gas ($Cl_2$) 904 and sodium hydroxide (NaOH) 906. The process is typically conducted with an aqueous solution of sodium chloride (NaCl) (e.g., the process uses water 908) and produces a hydrogen ($H_2$) 910 co-product. Other chloride compounds can be used, such as lithium chloride (LiCl), potassium chloride (KCl), calcium chloride ($CaCl_2$), and magnesium chloride ($MgCl_2$), and hydrates thereof. The chloralkali process consumes a considerable amount of electrical power 912. There are three chloralkali methods currently used in industry, referred to as membrane plants, diaphragm plants, and mercury plants. New electrochemical cells and processes are being developed that, for example, use a metal chloride intermediate, such as described in U.S. patent application Ser. Nos. 12/989,785, 12/721,545, 12/375,632, and 12/541,055, each of which is incorporated herein by reference in its entirety. Each type of chloralkali process can be integrated with OCM to realize surprising synergies described herein.

Figure 10:
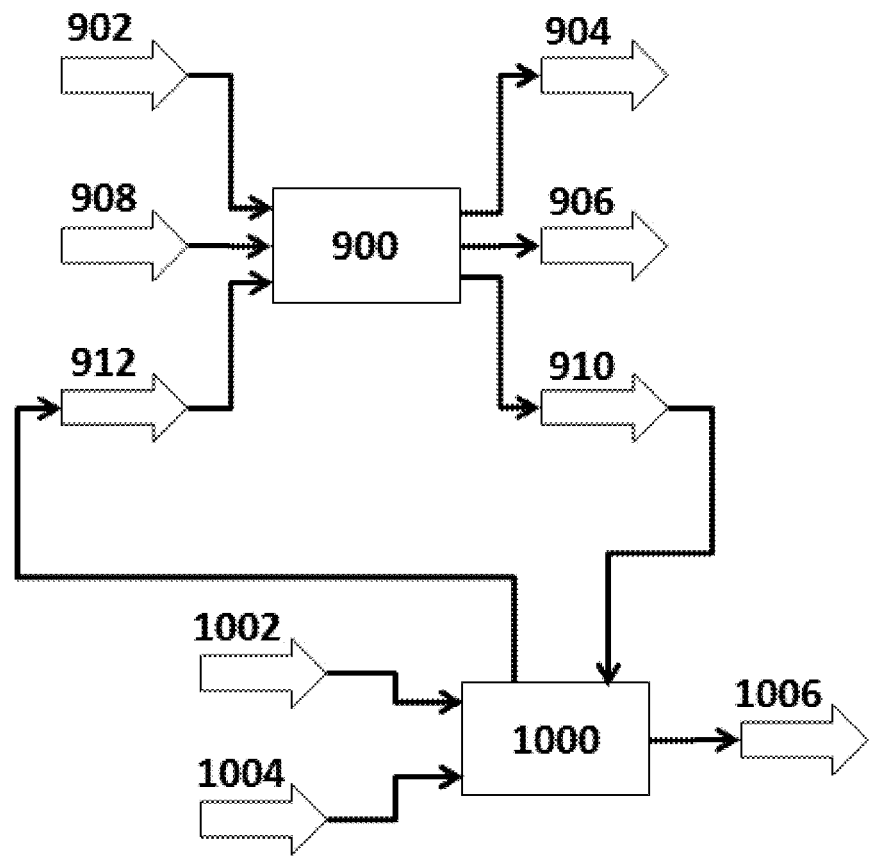
FIG. 10 is a schematic illustration of OCM integrated with a chloralkali process.

FIG. 10 shows a schematic illustration of an OCM process 1000 integrated with a chloralkali process 900. The OCM process, consumes oxygen ($O_2$) 1002 and methane 1004 (e.g., natural gas) and produces $C_{2+}$ compounds such as ethylene 1006. The OCM process can accept $H_2$ 910 from the chloralkali process (e.g., at the methanation module 110 as shown in FIG. 1A) for conversion of CO and/or $CO_2$ to additional methane for recycle to the OCM reactor. The OCM process is exothermic and the heat of reaction can be converted to electricity 912 (e.g., cogeneration) for use in the chloralkali process.

Integration of OCM Processes with EDC and/or VCM Process

The present disclosure recognizes certain unexpected synergies that can be achieved by integrating OCM with the production of vinylchloride monomer (VCM) and/or ethylene dichloride (EDC) (e.g., EDC/VCM process). This is because the EDC/VCM process uses ethylene as a feedstock, but does not require polymer-grade ethylene. Therefore, the OCM process does not require significant capital and operating expense associated with purifying ethylene.

Figure 11:
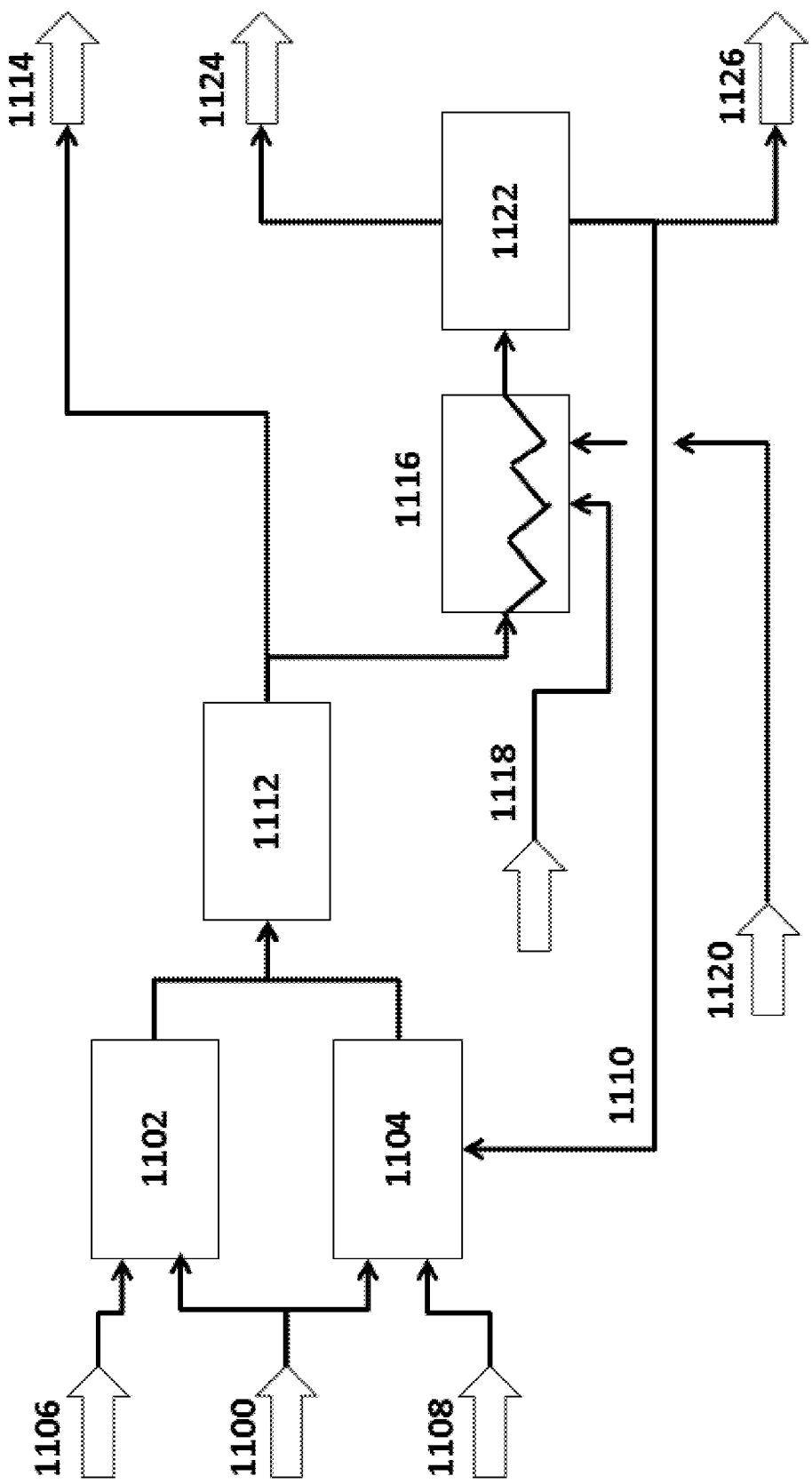
FIG. 11 is a schematic illustration of an ethylene dichloride (EDC) and vinylchloride monomer (VCM) production process.

With reference to FIG. 11, the ethylene 1100 can be provided by OCM (not shown). The ethylene can be about 99.99%, about 99.95%, about 99.9%, about 99.5%, about 99%, about 97%, about 95%, about 93%, about 90%, about 85%, about 80%, about 75%, or about 70% pure on a mass basis. In some cases, the ethylene is less than about 99.99%, less than about 99.95%, less than about 99.9%, less than about 99.5%, less than about 99%, less than about 97%, less than about 95%, less than about 93%, less than about 90%, less than about 85%, less than about 80%, less than about 75%, or less than about 70% pure on a mass basis. In some cases, the ethylene is greater than about 70%, greater than about 75%, greater than about 80%, greater than about 85%, greater than about 90%, greater than about 93%, greater than about 95%, greater than about 97%, greater than about 99%, greater than about 99.5%, greater than about 99.9%, greater than about 99.95%, or greater than about 99.99% pure on a mass basis.

Continuing with FIG. 11, the ethylene 1100 can be added to a direct chlorination reactor 1102 and/or an oxy-chlorination reactor 1104. The direct chlorination reactor 1102 uses chlorine gas ($Cl_2$) 1106 as a reactant and the oxy-chlorination reactor 1104 uses oxygen ($O_2$) 1108 and hydrochloric acid (HCl) 1110 as reactants. The HCl can be produced in the process and recycled to the oxy-chlorination reactor 1104. A first separations module 1112 can be used to enrich an EDC product 1114. A portion of the EDC can be cracked in a furnace 1116 using, for example, energy derived from natural gas 1118 and/or $H_2$ 1120. The cracked EDC can be separated in a second separations module 1122 to provide a VCM product stream 1124 and HCl 1126, which can be recycled 1110 to the oxy-chlorination reactor 1104.

Figure 12:
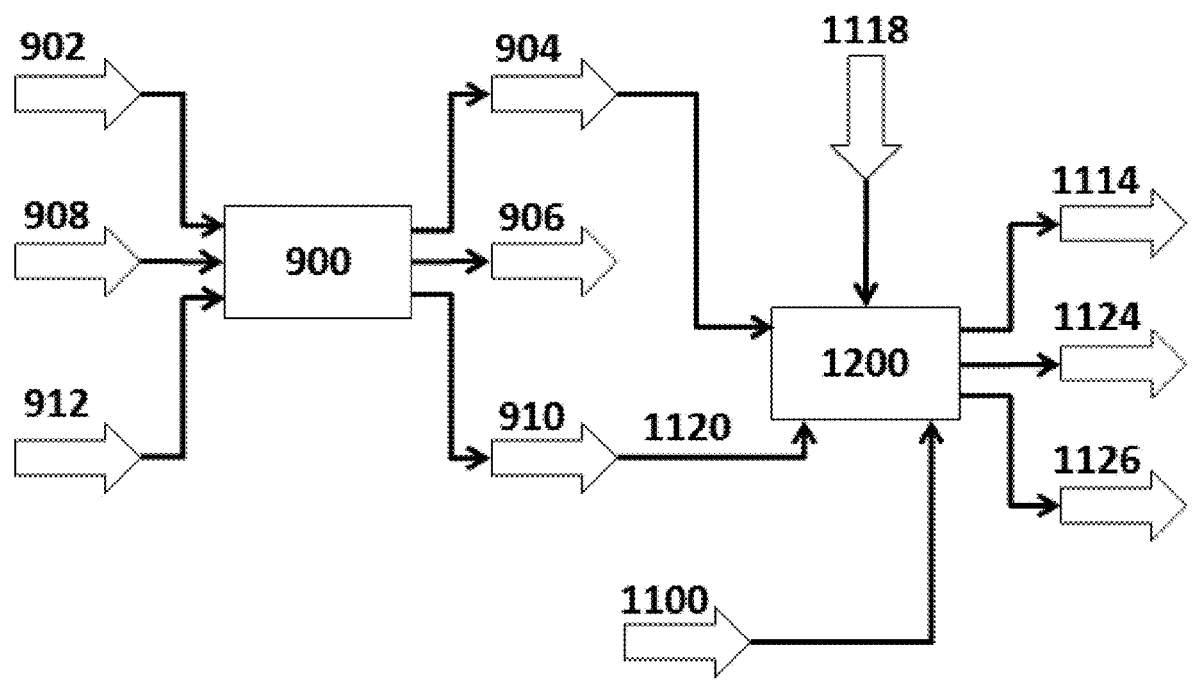
FIG. 12 is a schematic illustration of an EDC/VCM process integrated with a chloralkali process.

Some chloralkali process are integrated with the production of vinylchloride monomer (VCM) and/or ethylene dichloride (EDC). As shown in FIG. 12, some of the $Cl_2$ 904 produced by the chloralkali process 900 can be used in the EDC/VCM process 1200 (e.g., in the direct chlorination reactor 1102). Also, some or all of the $H_2$ 910 produced by the chloralkali process 900 can be used in the EDC/VCM process 1200 (e.g., as fuel 1120 for the EDC cracking furnace 1116). Additional fuel for the EDC cracking furnace can be derived from natural gas 1118. The process consumes ethylene 1100 and some of the products of the combined chloralkali and EDC/VCM process include EDC product 1114, VCM 1124 and HCl 1126.

Figure 13:
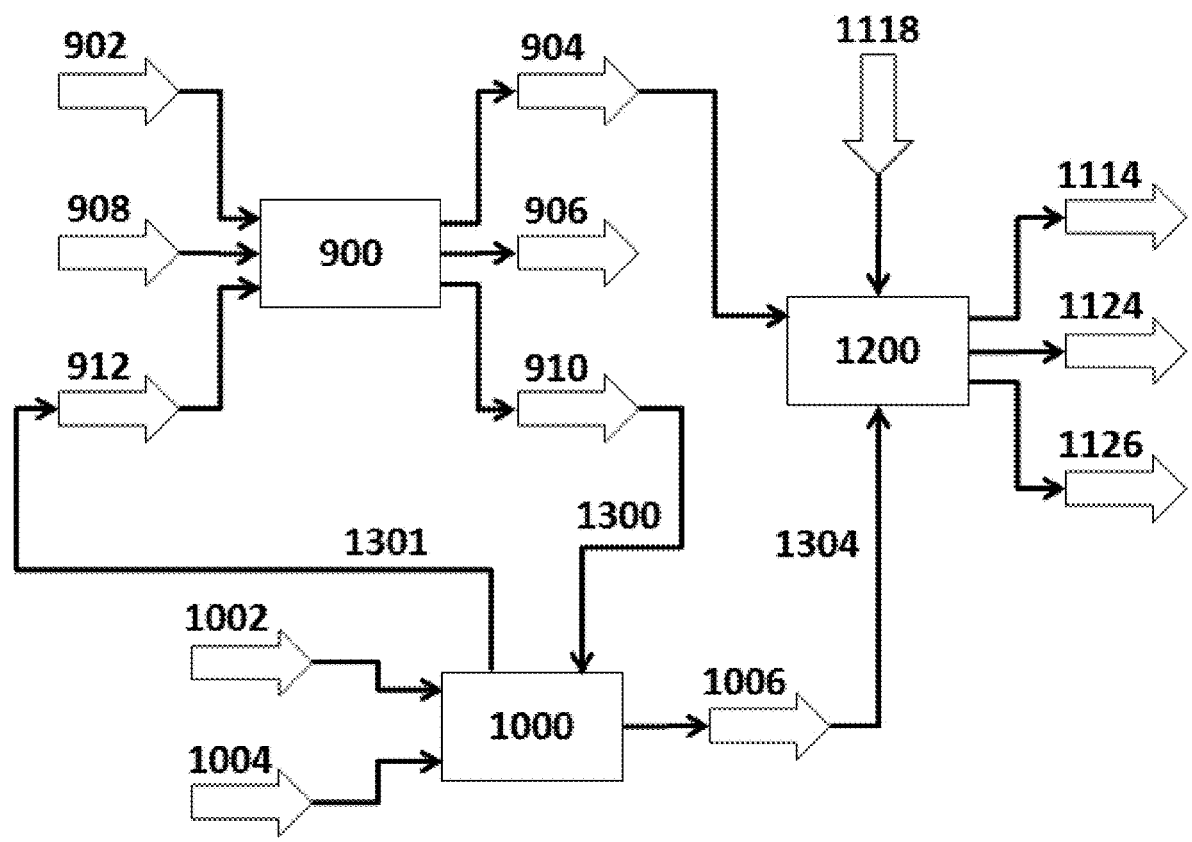
FIG. 13 is a schematic illustration of OCM integrated with an EDC/VCM process and a chloralkali process.

In some instances, as shown in FIG. 13, OCM can be integrated with both an EDC/VCM process and a chloralkali process. In this case, the chloralkali process 900 provides $H_2$ 1300 to the OCM process, the OCM process provides electrical power 1302 to the chloralkali process, and the OCM process provides ethylene 1304 to the EDC/VCM process 1200.

In some cases, a modified chloralkali process is integrated with a modified EDC production process in which $Cl_2$ is not produced as an intermediate. Instead, a metal chloride solution can be produced (e.g., $CuCl_2$) as the intermediate, for example as described in U.S. patent application Ser. No. 14/446,791, which is incorporated herein by reference in its entirety. OCM can also be integrated with these facilities as described herein.

The processes of the present disclosure can take advantage of the synergies made possible by OCM integration to chloralkali, EDC, or VCM producing units. An OCM unit can be a good fit between inputs and outputs of the two processes; OCM can produce ethylene and power, which can be the main inputs to chloralkali, EDC, or VCM processes. Chloralkali processes can produce hydrogen as a main co-product, which can be utilized in an OCM unit (rather than being combusted or vented) to reduce or eliminate $CO_2$ emissions and push carbon efficiency towards or up to 100%. EDC processes can operate with non-polymer-grade ethylene (alkanes are inert in EDC processes), so the separations unit of an OCM unit can produce chemical grade ethylene, which can result in a reduced capital expenditure (capex). Additionally, typical EDC scale can match small scale OCM implementations.

Figure 14:
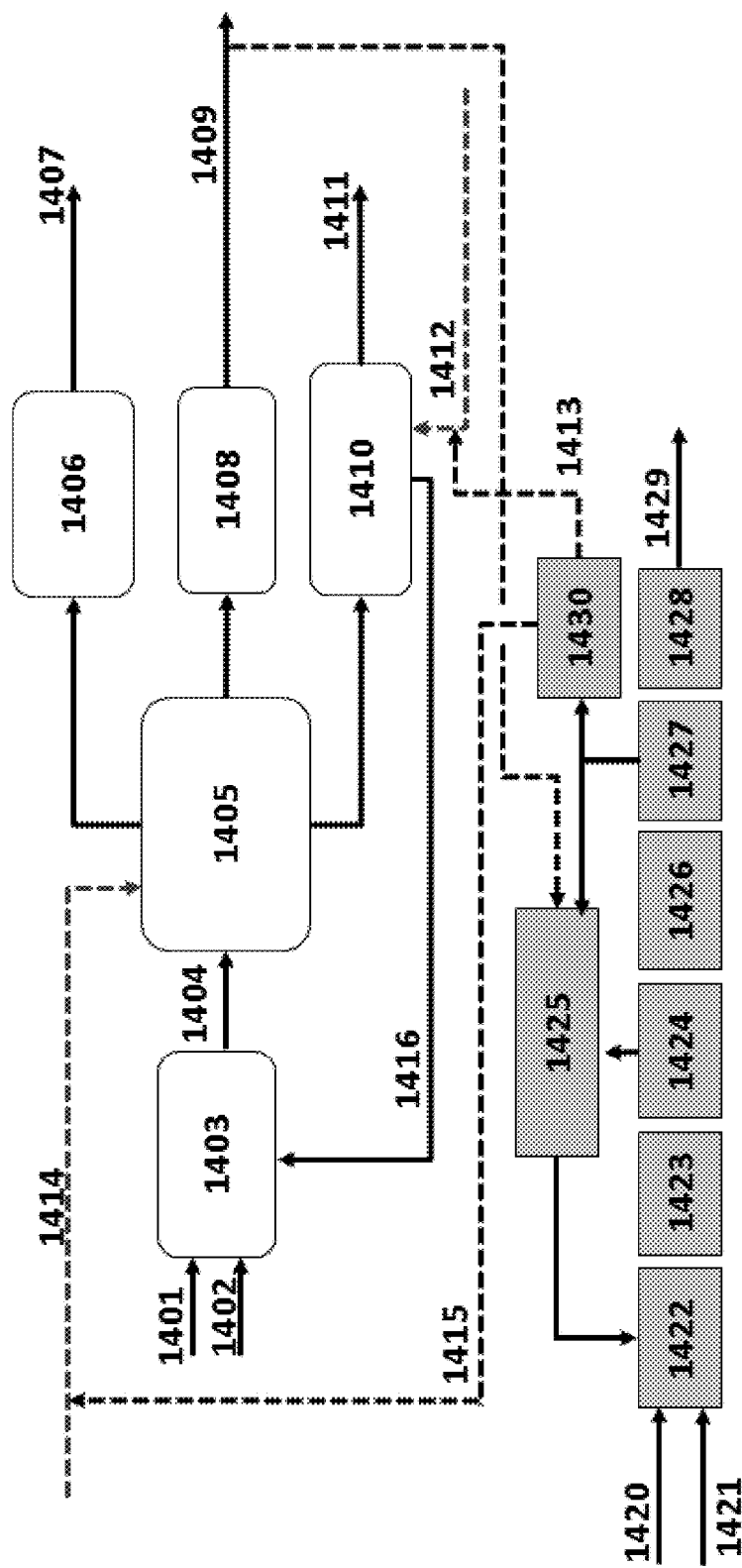
FIG. 14 shows an example of a process integrating OCM with a diaphragm-type chloralkali process.

FIG. 14 shows an example of a process integrating OCM with a diaphragm-type chloralkali process. The production capacity of the chloralkali process is at least about 300,000 tons per year (300 kTa) of chlorine. The production capacity of the OCM process is at least about 100,000 tons per year (100 kTa) of ethylene. Co-generation with the OCM process can produce about 100-120 ton/hr of steam and about 80-120 MW of power.

Salt 1401 and water 1402 are fed to a brine saturation unit 1403, and purified brine 1404 is then fed into an electrolysis unit 1405. The electrolysis of purified brine in the chloralkali process uses power 1414 (e.g., up to about 2970 kWh per ton of $Cl_2$ produced); at least a portion of this power can be provided 1415 from co-generation with the OCM process (e.g., about 80-120 MW). A chlorine product stream can be subjected to treatment and liquefaction 1406 before being output as chlorine product 1407 (e.g., at least about 300 kTa). A hydrogen stream can be subjected to cooling and oxygen removal 1408 before further use; hydrogen 1409 (e.g., at least about 8400 kTa or at least about 950 kg/hr) can be directed into a methanation unit in the OCM process, for example. A caustic soda product stream 1411 (e.g., 50% caustic soda) can be produced (e.g., about 338.4 kTa) after concentration and cooling 1410. A reclaimed salt stream 1416 can be recycled to the brine saturation unit. The cooling process can use steam 1412 (e.g., up to about 610 kWh per ton of $Cl_2$), at least a portion of which can be provided 1413 from co-generation 1430 with the OCM process (e.g., about 100-120 ton/hr). It is assumed that 1 ton of steam is 250 kWh at 19 bar. The processes are integrated with respect to electrical power, hydrogen and steam. Natural gas 1420 and ethane 1421 can be fed into an OCM reactor 1422 with other reagents and reacted in an OCM process. Post-bed cracking 1423 can be employed to produce additional ethylene. $CO_2$ can be removed in a $CO_2$ removal unit 1424 and fed into a methanation unit 1425. The OCM product stream can be further processed in a drying unit 1426, a de-methanizer unit 1427, and a $C_2$ hydrogenation unit 1428, producing an ethylene stream 1429.

Figure 15:
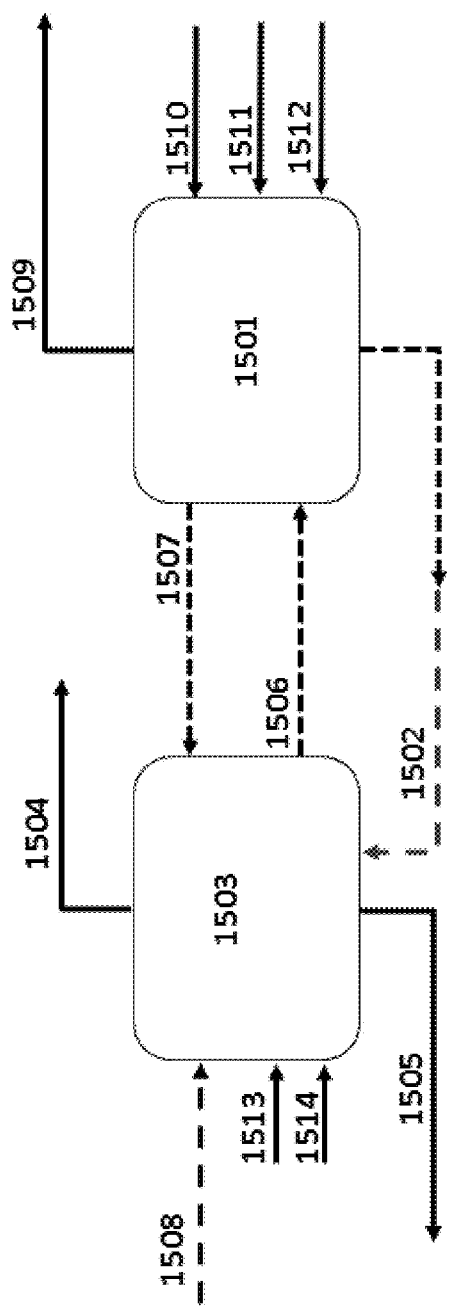
FIG. 15 shows a material and energy balance for the process shown in FIG. 14.

FIG. 15 shows a material and energy balance for the process shown in FIG. 14. All of the electrolytic hydrogen is used in the OCM unit 1501. The OCM process provides a portion of the steam 1502 used by the electrolysis unit 1503 (e.g., chloralkali process). The electrolysis unit produces at least about 300 kTa of chlorine 1504 and at least about 338.4 kTa of caustic soda 1505, as well as at least about 950 kg/hr of hydrogen 1506 which is fed into the OCM unit. The chloralkali process receives about 80-120 MW of power 1507 from the OCM process, and additional power 1508 of at least about 104 MW from other sources. The chloralkali process also receives salt 1513 and water 1514. The OCM unit produces at least about 100 kTa ethylene 1509 (e.g., at least about 0.3 tons of ethylene per ton of $Cl_2$ produced by the chloralkali process), as well as at least about 85 ton/hr steam (e.g., up to about 610 kWh per ton of $Cl_2$) which is fed into the electrolysis unit. The OCM unit consumes about 40-50 MMSCFD of natural gas 1510, about 15-18 MMSCFD of oxygen 1511, and about 6-9 MMSCFD of ethane 1512.

Integration of OCM Processes with an Ammonia Process

The present disclosure provides techniques that can advantageously employ certain unexpected synergies that can be achieved by integrating OCM with the production of ammonia ($NH_3$). In some cases, an existing ammonia process is retrofitted with an OCM process. These synergies can include increasing the capacity of a reforming portion of an ammonia process, in some cases without modification of the steam methane reformer and/or secondary reformer. In some cases, such reforming capacity expansion can be achieved without over-burdening other unit operations leading up to the ammonia synthesis module (e.g., the "synloop"). Therefore, the addition of an OCM process to an ammonia production process can be performed without the significant capital and operating expense that can be associated with purifying ethylene.

Figure 16:
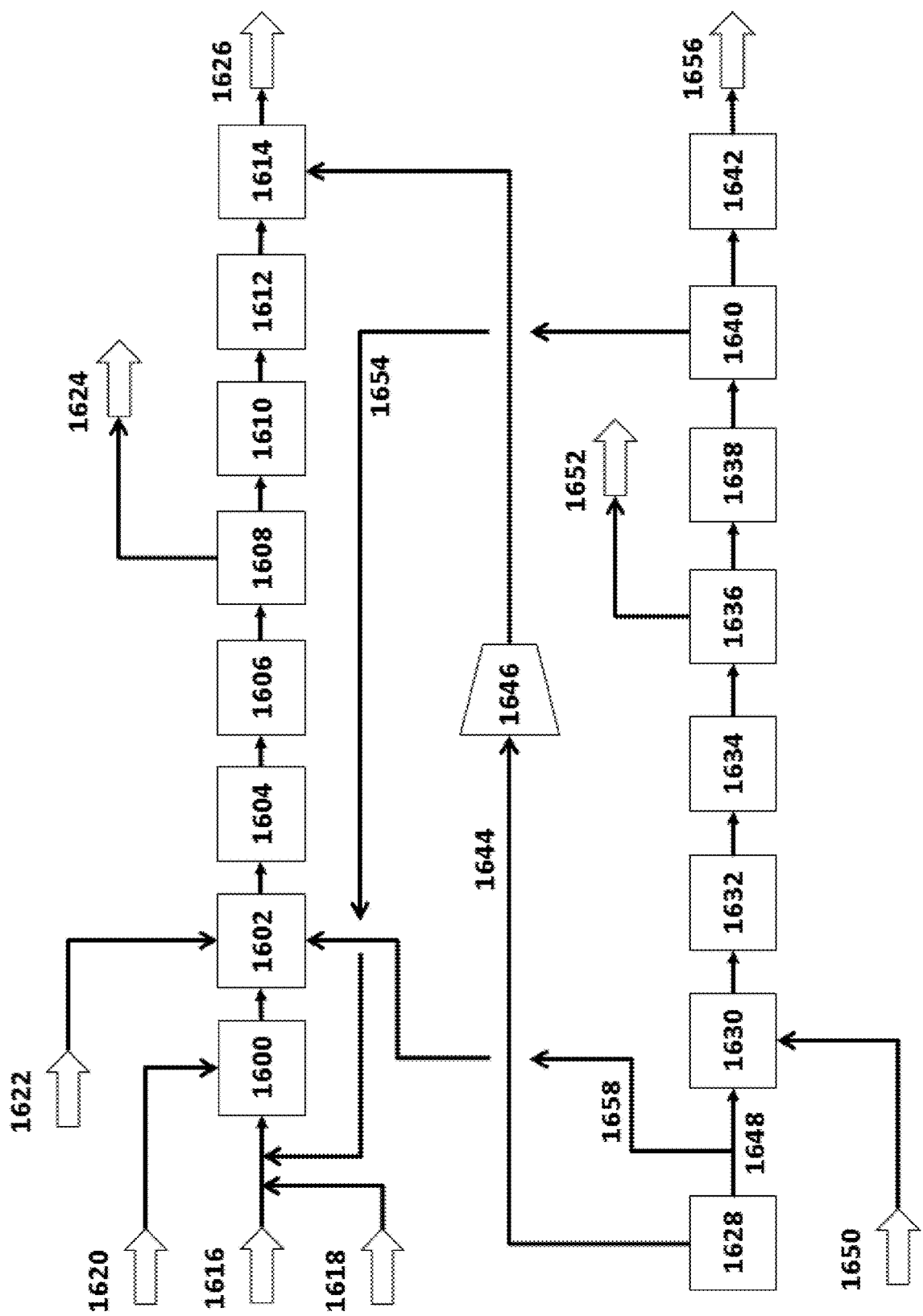
FIG. 16 is a schematic illustration of OCM integrated with an ammonia process.

With reference to FIG. 16, an ammonia process can comprise a steam methane reformer 1600, a secondary reformer 1602, a heat recovery module 1604, a water-gas shift conversion unit 1606, a $CO_2$ separation module 1608, a methanation reactor 1610, a syngas compressor 1612 and an ammonia synthesis and separation module 1614. The ammonia synthesis module can be an implementation of the Haber-Bosch catalytic process.

Following the ammonia process, the steam methane reformer 1600 can accept natural gas (e.g., as feedstock) 1616 and combine it with steam 1618. The feedstock can enter the tubeside of the SMR, for example at a temperature of about 500° C. A large amount of heat can be supplied to the tubes of the SMR, for example via combustion of natural gas fuel 1620 in the radiation section of the SMR, in order to heat up the reacting feed (e.g., to a temperature from about 740 to about 800° C.) and sustain an endothermic reforming reaction that produces syngas (e.g., via the reaction $CH_4 + H_2O \leftrightarrow CO + 3H_2$, which heat of reaction can also be supplied by the natural gas fuel 1620). Because reforming is an equilibrium reaction, a certain portion of the methane may not be converted to syngas in the SMR (e.g., about 8-15%). The SMR effluent can be directed to a secondary reformer 1602 where air 1622 is added to reduce the methane ($CH_4$) concentration to about 0.3-1.2%, such as via a combination of combustion and reforming reactions. At this point, the temperature of the stream can be as high as about 900-1000° C.; a heat recovery module 1604 can be used to lower the temperature and recover energy, such as via generation of high pressure superheated steam. The cooled product then can then be directed to a water-gas shift reactor 1606 to produce more hydrogen (e.g., via the reaction $CO + H_2O \leftrightarrow CO_2 + H_2$). At this point, the ratio of $H_2$ to $N_2$ can be about 3, which can match the reaction stoichiometry for ammonia production. $CO_2$ can then be removed 1624 in a separation module 1608, leaving about 5-50 ppm $CO_2$ and about 0.1-0.4% CO. $CO_2$ and CO can be strong poisons to ammonia synthesis catalysts, so residual amounts of $CO_2$ and CO can be converted to methane (which is inert in the ammonia synthesis reaction) in a methanation reactor 1610. A syngas compressor 1612 and an ammonia synthesis and separation module 1614 can be used to complete the process and produce ammonia 1626. Note that for clarity, various streams and units, such as ammonia purification, may not have been shown or described.

In an ammonia process, the extent of reaction in the secondary reformer 1602 can be limited by the amount of air 1622, as the nitrogen ($N_2$) from this air stream can be the source of $N_2$ for the production of ammonia. However, integrating and/or retrofitting an ammonia process with an OCM process can obviate this limitation, along with providing additional benefits, including those discussed herein.

With reference to FIG. 16, the OCM process can comprise an air separation unit (ASU) 1628, an OCM reactor 1630, a heat recovery module 1632, a compression module 1634, a $CO_2$ removal unit 1636, a dryer module 1638, a de-methanizer module 1640, and a fractionation module 1642. Following the OCM process, the ASU can separate air into a nitrogen stream 1644, which can be fed to the ammonia process to provide a source of clean $N_2$ reactant (e.g., not having oxygenated compounds such as CO or $CO_2$). In some cases, other processes (e.g., separations) can be used to provide air and nitrogen. For example, a pressure swing adsorption (PSA) unit can be used to provide $O_2$ and $N_2$. The ammonia synthesis module 1614 can operates at about 80 to 200 bar pressure. The nitrogen stream 1644 can be compressed to operating pressure in an auxiliary compressor 1646 or in the syngas compressor of the ammonia process 1612. The oxygen ($O_2$) 1648 produced by the ASU 1628 can be supplied to both the OCM reactor 1630 and the secondary reformer of the ammonia process 1602 (e.g., offsetting or supplementing $O_2$ from air 1622). Continuing with the OCM process, the oxygen can be reacted with methane 1650 (e.g., from natural gas) to produce ethylene. Pressure can increase, and heat, $CO_2$ and water can be recovered in a series of units (e.g., 1632, 1634, 1636 and 1638 in any order). In some cases, $CO_2$ from the ammonia process 1624 and/or OCM process 1652 can be used in processes including but not limited to methanol, chloralkali, urea, and combinations thereof. The overhead stream 1654 from the de-methanizer 1640 can comprise un-converted methane from the OCM process which can be used to supplement and/or offset natural gas to the SMR of the ammonia process 1600. Since this overhead stream 1654 can have $H_2$ (e.g., about 10%) and CO (e.g., about 1.5%), the stream is already partially reformed. The bottoms from the de-methanizer 1640 can be sent to the fractionation module 1642 to produce ethylene product 1656.

Integrating and/or retrofitting an ammonia process with an OCM process can result in additional $H_2$ and/or $NH_3$ produced (e.g., at least about 5%, at least about 10%, at least about 15%, at least about 20%, at least about 25%, at least about 30%, at least about 35%, or at least about 40% additional $H_2$ and/or $NH_3$ compared to an ammonia process without OCM). This capacity expansion can emerge from any combination of a number of effects, such as: (a) the OCM process can supply the ammonia process with some partially reformed material (i.e., about 10% $H_2$ and about 1.5% CO in the de-methanizer overhead 1654); (b) in contrast to natural gas, the de-methanizer overhead 1654 can lack "superior hydrocarbons" (e.g., $C_{2+}$ alkanes), therefore the temperature threshold at which coking may occur can be higher and accordingly the SMR inlet temperature can be raised (e.g., raised from about 500° C. to about 550° C. or about 600° C.), allowing the heat supplied in the SMR radiation section to go toward the heat of reaction rather than providing a temperature increase, and thus increasing the syngas production performed by the SMR unit itself; and/or (c) supplying clean nitrogen ($N_2$) 1644 can break the stoichiometric limit of air 1622 as the sole nitrogen source, this coupled with $O_2$ supplementation 1658 can allow relatively more reforming to be carried out in the secondary reformer 1602, allowing a higher amount of $CH_4$ slippage from the SMR (e.g., about 15-25% rather than 8-15% of un-converted methane).

In some cases, the process units between reforming and ammonia synthesis do not need to be de-bottlenecked or capacity expanded because, while extra $H_2$ is produced, the $N_2$ enters the process after these steps (i.e., at 1644 rather than with the air 1622), so the total process flow is relatively unchanged.

In some cases, the ammonia synloop 1614 requires expansion in a revamp, however this is a relatively low capital item in comparison to the rest of the ammonia process units and such revamp results in increased ammonia product 1626.

The systems and methods of the present disclosure can be nitrogen-efficient and/or energy-efficient. In some cases, the systems or methods of the present disclosure have a nitrogen efficiency of at least about 50%, at least about 55%, at least about 60%, at least about 65%, at least about 70%, at least about 75%, at least about 80%, at least about 85%, or at least about 90%. In some cases, a system of the present disclosure or method for use thereof has a ratio of all nitrogen atoms output from the system as nitrogen products to all nitrogen atoms input to the system of at least about 0.4, at least about 0.50, at least about 0.55, at least about 0.60, at least about 0.65, at least about 0.70, at least about 0.75, at least about 0.80, at least about 0.85, at least about 0.90, or at least about 0.95.

In some cases, the systems or methods of the present disclosure have a nitrogen efficiency of between about 50% and about 85%, between about 55% and about 80%, between about 60% and about 80%, between about 65% and about 85%, between about 65% and about 80%, or between about 70% and about 80%. In some cases, a system of the present disclosure or method for use thereof has a ratio of all nitrogen atoms output from the system as nitrogen products to all nitrogen atoms input to the system of between about 0.50 and about 0.85, between about 0.55 and about 0.80, between about 0.60 and about 0.80, between about 0.65 and about 0.85, between about 0.65 and about 0.80, or between about 0.70 and about 0.80.

In some instances, the nitrogen efficiency is at least about 50%, at least about 55%, at least about 60%, at least about 65%, at least about 70%, at least about 75%, at least about 80%, at least about 85% or at least about 90%. In some instances, the nitrogen efficiency is between about 50% and about 85%, between about 55% and about 80%, between about 60% and about 80%, between about 65% and about 85%, between about 65% and about 80%, or between about 70% and about 80%. In some instances, a system of the present disclosure or method for use thereof has a ratio of all nitrogen atoms output from the system as nitrogen products to all nitrogen atoms input to the system of at least about 0.60, at least about 0.65, at least about 0.70, at least about 0.75, at least about 0.80, at least about 0.85 or at least about 0.90. In some instances, a system of the present disclosure or method for use thereof has a ratio of all nitrogen atoms output from the system as nitrogen products to all nitrogen atoms input to the system of between about 0.50 and about 0.85, between about 0.55 and about 0.80, between about 0.60 and about 0.80, between about 0.65 and about 0.85, between about 0.65 and about 0.80, or between about 0.70 and about 0.80.

Integration of OCM Processes with a Methanol to Propylene (MTP) Process

Figure 17:
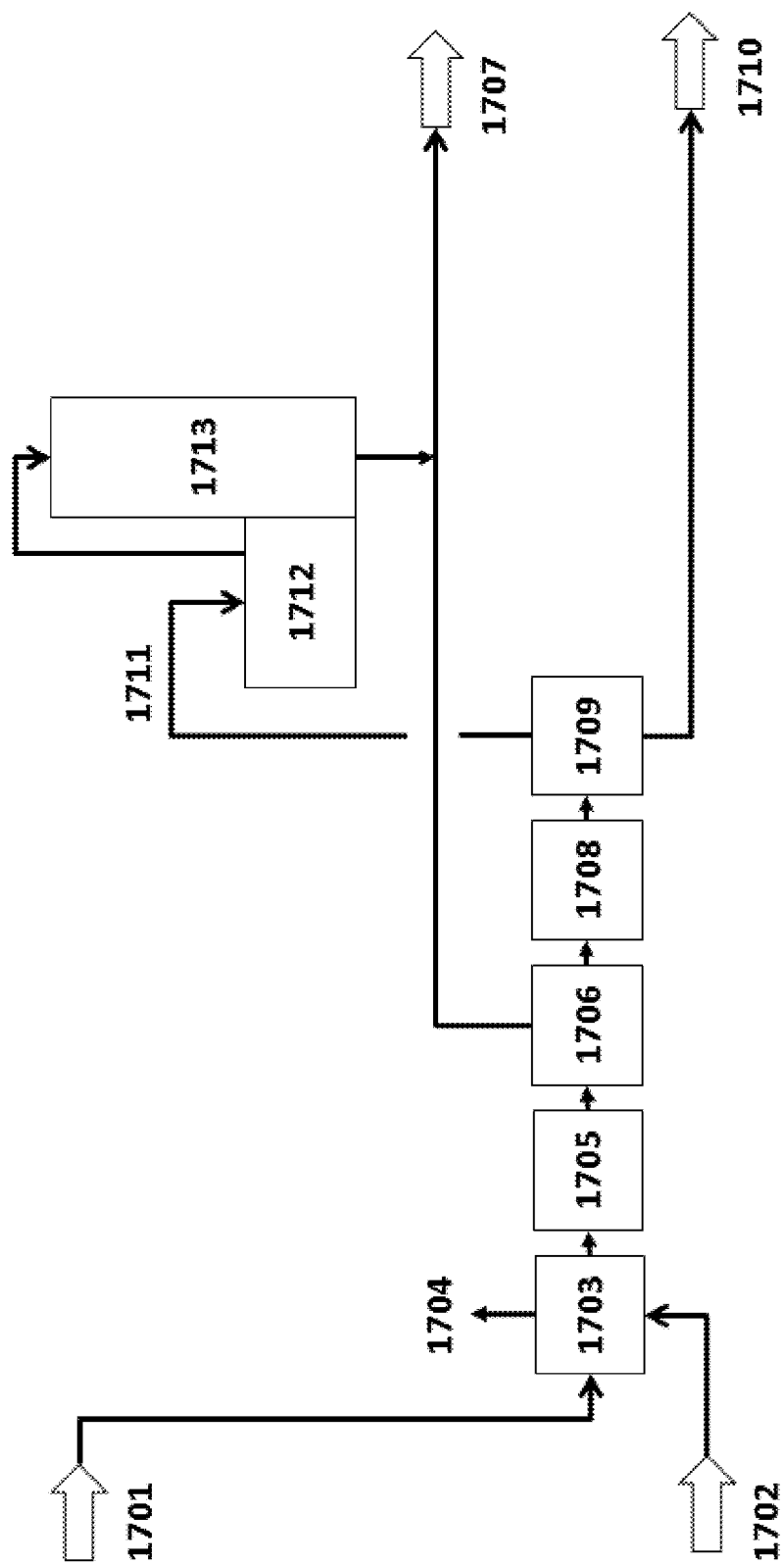
FIG. 17 shows a schematic illustration of OCM integrated with a methanol-to-propylene (MTP) process.

FIG. 17 shows an exemplary OCM process for integration with a methanol to propylene (MTP) process. Natural gas 1701 and oxygen 1702 are fed into an OCM reactor 1703. High pressure superheated (HPSH) steam 1704 is produced from the OCM unit. The OCM product stream is fed into a post-bed cracking unit 1705, and then into a $CO_2$ removal unit 1706. Recovered $CO_2$ is directed for use in a balanced syngas stream 1707. The OCM product stream is further directed through a drying unit 1708 and a de-methanizer unit 1709. $C_{2+}$ compounds 1710 are recovered from the de-methanizer, while unconverted methane and other light components including $H_2$ and CO 1711 can be directed to a reformer (e.g., a steam methane reformer) 1712 and 1713. The components are then added to the balanced syngas stream.

Figure 18:
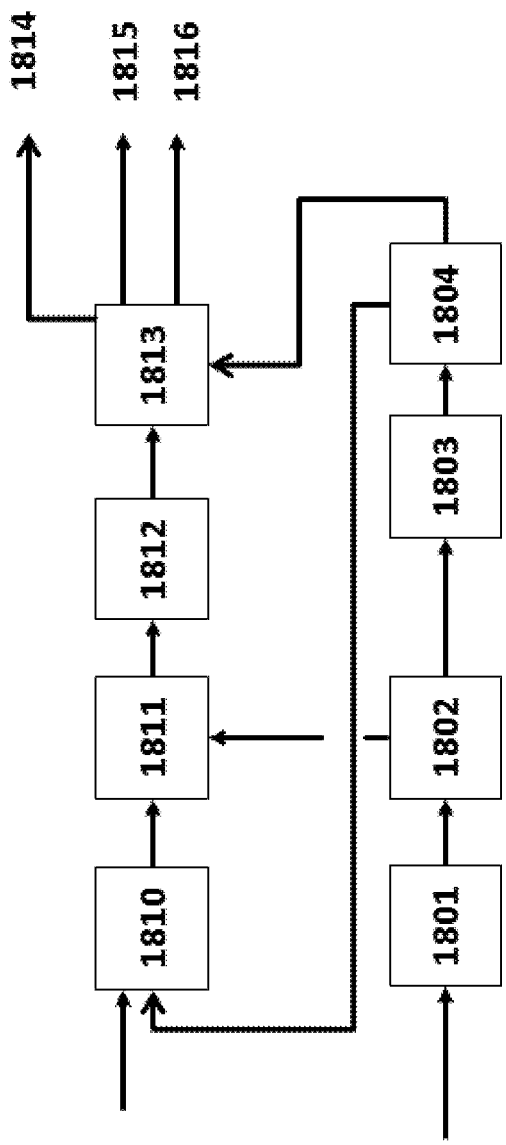
FIG. 18 shows a schematic illustration of an OCM process integrated with an MTP process.

FIG. 18 shows an exemplary integration scheme for an OCM process and an MTP process. Natural gas and oxygen are fed into an OCM unit 1801 with a post-bed cracking region. The OCM product stream is then processed in a $CO_2$ removal unit 1802, a drying unit 1803, and a de-methanizer unit 1804. In parallel, a methane stream (e.g., natural gas) is fed into a syngas unit 1810, along with a methane stream from the de-methanizer unit. The syngas stream is fed into a methanol synthesis unit 1811, along with $CO_2$ from the $CO_2$ removal unit. Methanol from the methanol synthesis unit is then fed into a methanol-to-propylene synthesis unit 1812, and the MTP product stream is fed into a recovery unit 1813. The $C_{2+}$ product stream from the de-methanizer unit is also fed into the recovery unit. An ethylene stream 1814, a propylene stream 1815, and a $C_{4+}$ compounds stream 1816 are recovered from the recovery unit.

Integration of OCM Processes with a Liquid Natural Gas (LNG) Process

OCM and/or ETL processes can be integrated with liquid natural gas (LNG) processes.

For example, an LNG process can be integrated with OCM and ETL processes for fuel production. Such a process can convert methane, ethane, and optionally propane into fuel such as high-octane gasoline. Capital expenditure (CapEx) can be reduced due to synergies and overlap in needed equipment, such as product separations equipment. A fuel product, such as gasoline, can be mixed with condensate from the LNG process or separated via a dedicated column.

Figure 19:
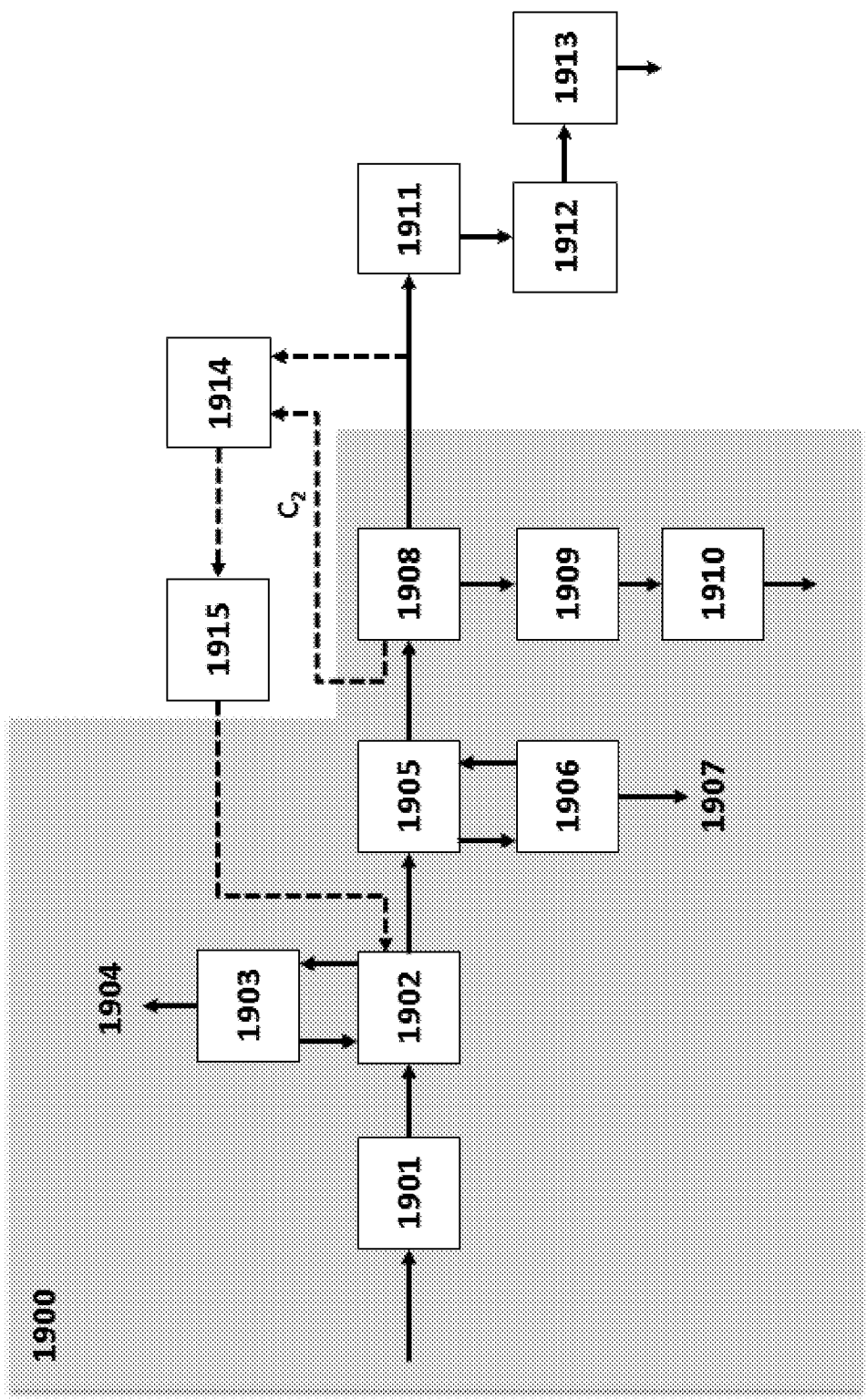
FIG. 19 shows a schematic illustration of an OCM process and an ETL process integrated with a liquid natural gas (LNG) process.

FIG. 19 shows an integration of OCM and ETL processes with an LNG process for fuel production. A feed gas preparation system 1900 (e.g., of a gas processing plant) receives gas into its inlet gas facilities 1901. The stream is then directed into a gas treating unit 1902 with a solvent regeneration unit 1903, from which $CO_2$ and $H_2S$ 1904 are recovered. The stream is then directed into a dehydration unit 1905 with a regeneration unit 1906, from which water 1907 is recovered. The stream is then directed to a liquid petroleum gas (LPG) extraction unit 1908, from which condensate is recovered and sent to storage 1909 (e.g., $LPG/C_{5+}$ storage) and offloading 1910 for transportation (e.g., on ships). Dry gas from the LPG extraction unit is directed to an LNG liquefaction unit 1911, from which LNG product is directed to storage 1912 and offloading 1913 for transportation (e.g., on ships). At least a portion of the dry gas and $C_2$ from the LPG extraction unit can be directed to an OCM unit 1914. The OCM product stream can be directed to an ETL unit 1915, with fuel products (e.g., high octane gasoline) mixed with condensate from the LNG process or separated via a dedicated column. Light products and unreacted methane, for example, can be directed back into the gas treatment unit.

LNG processes can also be integrated with OCM processes for polymer production. For example, methane and ethane can be converted to a polymer (e.g., polyethylene). Capital expenditure (CapEx) can be reduced due to synergies and overlap in needed equipment, such as product separations equipment. The value of the polymer produced can be used to pay for the OCM processes, the polymerization process, and to offset the cost of an LNG process, for example.

Figure 20:
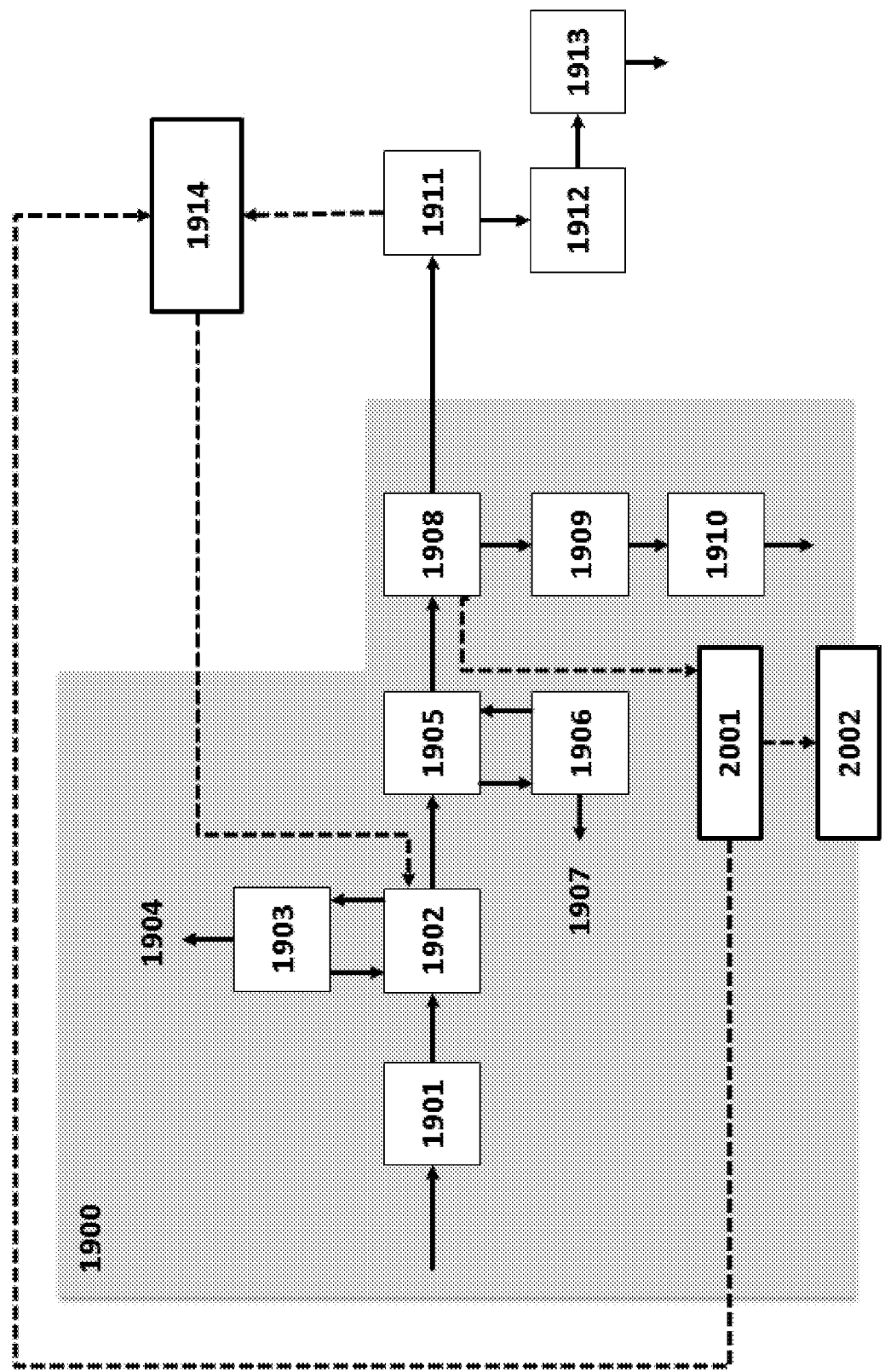
FIG. 20 shows a schematic illustration of OCM and ETL processes integrated with an LNG process for polymer production.

FIG. 20 shows an integration of an OCM process with an LNG process for polymer production. $C_2$ compounds from the LPG extraction unit are directed to a $C_2$ splitter 2001. Ethylene from the $C_2$ splitter is directed into a polyethylene unit 2002, while ethane from the $C_2$ splitter is directed to the OCM unit.

Integration of OCM Processes with an Oxalic Acid/Oxalate Process

An OCM process can be integrated with production of oxalic acid, oxalates, or derivatives thereof. For example, $CO_2$ produced in an OCM process can be directed to a reactor (e.g., an electrochemical reactor) for use in oxalic acid or oxalate production. Clean $CO_2$ from OCM can be converted to oxalate or oxalic acid, and optionally further to derivatives including glycolic acid, ethylene glycol, diglycolic acid, nitriloacetic acid, glyoxylic acid, and acetic acid.

Figure 21:
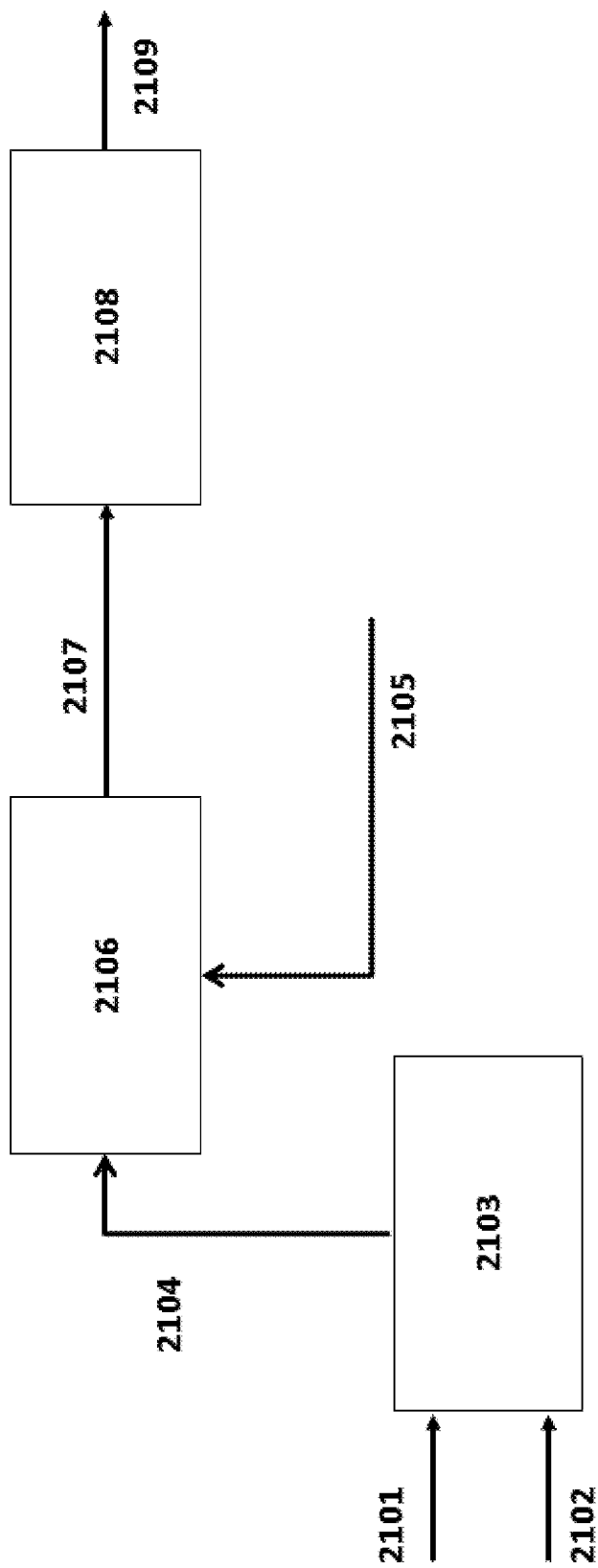
FIG. 21 shows a schematic illustration of an OCM process integrated with an oxalic acid/oxalate production process.

FIG. 21 shows an exemplary schematic for integration of OCM with oxalic acid or oxalate production. Methane (e.g., natural gas) 2101 and oxygen 2102 are directed into an OCM unit 2103. $CO_2$ 2104 from the OCM unit and hydrogen 2105 are directed into a reactor (e.g., electrocatalytic/electrochemical reductive coupling of $CO_2$ reactor) to produce oxalic acid and/or oxalates 2107. The oxalic acid and/or oxalates can be directed into a hydrogenation reactor 2108 to produce other derivative products 2109.

Integration of OCM Processes with an Ethylene Glycol Process

An OCM process can be integrated with production of ethylene glycol. For example, ethylene produced in an OCM process can be directed to a reactor (e.g., an oxidation reactor) for use in ethylene oxide production. Ethylene oxide can then be converted further to derivatives including ethylene glycol.

Figure 22:
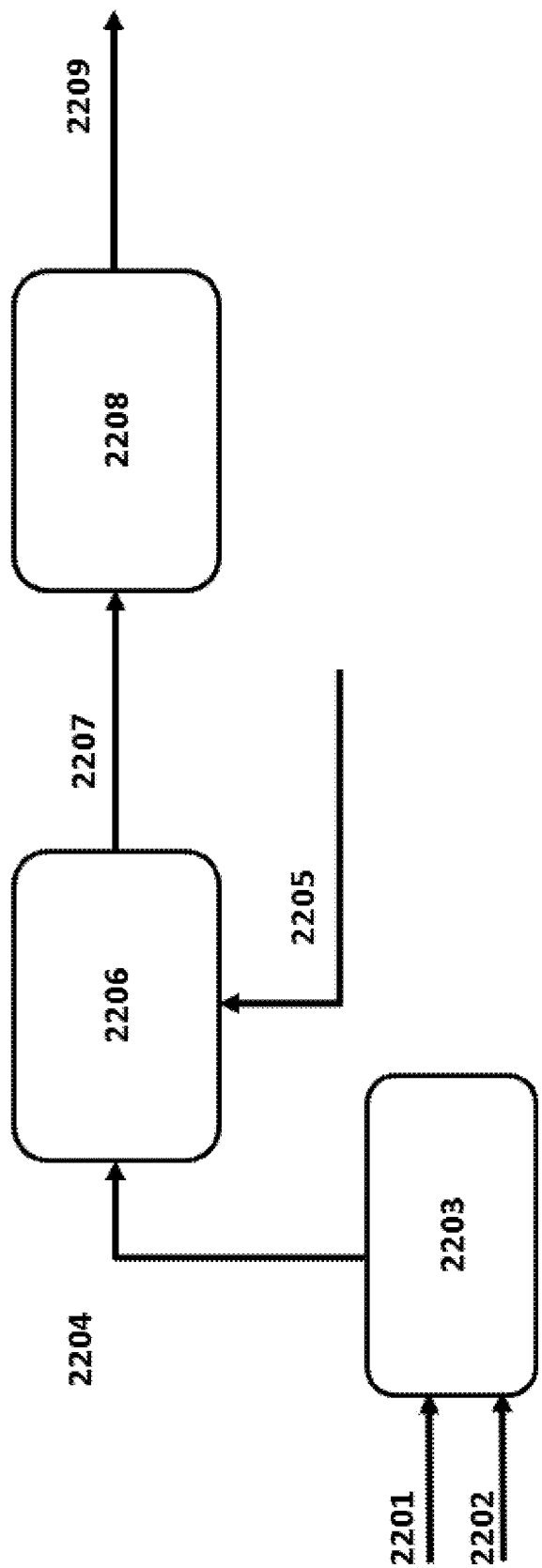
FIG. 22 shows a schematic illustration of an OCM process integrated with an ethylene glycol production process.

FIG. 22 shows an exemplary schematic for integration of OCM with ethylene glycol production. Methane (e.g., natural gas) 2201 and oxygen 2202 are directed into an OCM unit 2203 to produce ethylene 2204. The ethylene and oxygen 2205 (e.g., air or pure oxygen) are directed into an oxidation reactor 2206, which produces ethylene oxide 2207. The ethylene oxide is then directed into a hydration reactor 2208 to produce ethylene glycol 2209.

Integration of OCM Processes with a Propylene Process

OCM processes can be integrated with processes for the production of propylene, such as metathesis processes. Metathesis units can convert butene-2 and ethylene into propylene. The propylene produced can be of polymer grade and used as a feedstock to produce polypropylene.

The metathesis reaction can utilize an ethylene feed and a $C_4$ olefinic feed to produce propylene via a disproportionation reaction. In the absence of a $C_4$ feed, ethylene can be dimerized to produce the $C_4$ olefins used for metathesis. The $C_4$ olefin can be a butene-2 rich stream where the butene-2 content can be greater than about 90%, greater than about 93%, greater than about 95%, greater than about 97% or greater than about 99%. An OCM module can provide ethylene (e.g., polymer grade) to a dimerization unit, and/or to a metathesis unit. The metathesis reactor may contain a section for isomerization of butene-1 to butene-2. The product from the metathesis unit can contain predominantly propylene (and varying amounts of unreacted ethylene and butenes), along with some heavy $C_{5+}$ components. Conventional metathesis units can include $C_2$ separation, $C_3$ separation and a de-oiler ($C_{5+}$ removal). A metathesis unit integrated with an OCM system can have a common separations and purification system where the product stream from the metathesis unit is routed to the $C_2$ separations section of the OCM module (de-ethanizer). The de-ethanizer overhead can be sent to the $C_2$ splitter to generate polymer grade ethylene and an ethane product. The ethane product can be recycled to the OCM reactor. A part of the ethylene produced can be sent to the dimerization reactor and the remaining ethylene is sent to the metathesis unit. The de-ethanizer bottoms stream can be sent to a de-propanizer, followed by a $C_3$ splitter to produce (polymer grade) propylene. The de-propanizer bottoms can be sent to a de-butanizer or a de-pentanizer to recover a $C_4$ raffinate. In some embodiments, the butene rich stream from dimerization reactor can be isomerized in a reactive distillation section to convert butene-1 to butene-2 and separate the butene-2 for the metathesis reactor.

In some embodiments, the $C_4$ rich stream can be sourced from a refinery or a steam cracker. The refinery or steam cracker $C_4$ stream can be sufficient to provide for the metathesis unit with no dimerization required. In some cases, the $C_4$ stream can be mixed with the $C_4$ stream from the dimerization reactor. In either case (i.e., dimerization alone, dimerization plus off gas recovery or only off gas processing), the $C_4$ processing can also include either a selective hydrogenation unit (SHU) to hydrogenate any $C_4$ dienes to olefins, or a butadiene recovery unit or a total hydrogenation unit to hydrogenate the remaining $C_4$s after butene-2 has been utilized. In some cases, the final product is a $C_4$ LPG/$C_4$ raffinate containing butanes, and unreacted butenes.

The integrations described herein (e.g., OCM+metathesis+ polypropylene) can yield many advantages from a process and economic standpoint. The combined system can have a common separations and recovery system, a common refrigeration system, and take advantage of an integrated site with respect to utilities and off-sites. Additionally, the OCM system can generate excess steam for the entire system.

Additionally, ethylene from an OCM process can be supplied as a co-monomer for polypropylene production (e.g., 8-15% ethylene co-monomer). A separations section of an OCM process can handle the recycle streams from a metathesis unit and a polypropylene unit in addition to the separations for the OCM process itself.

Figure 23:
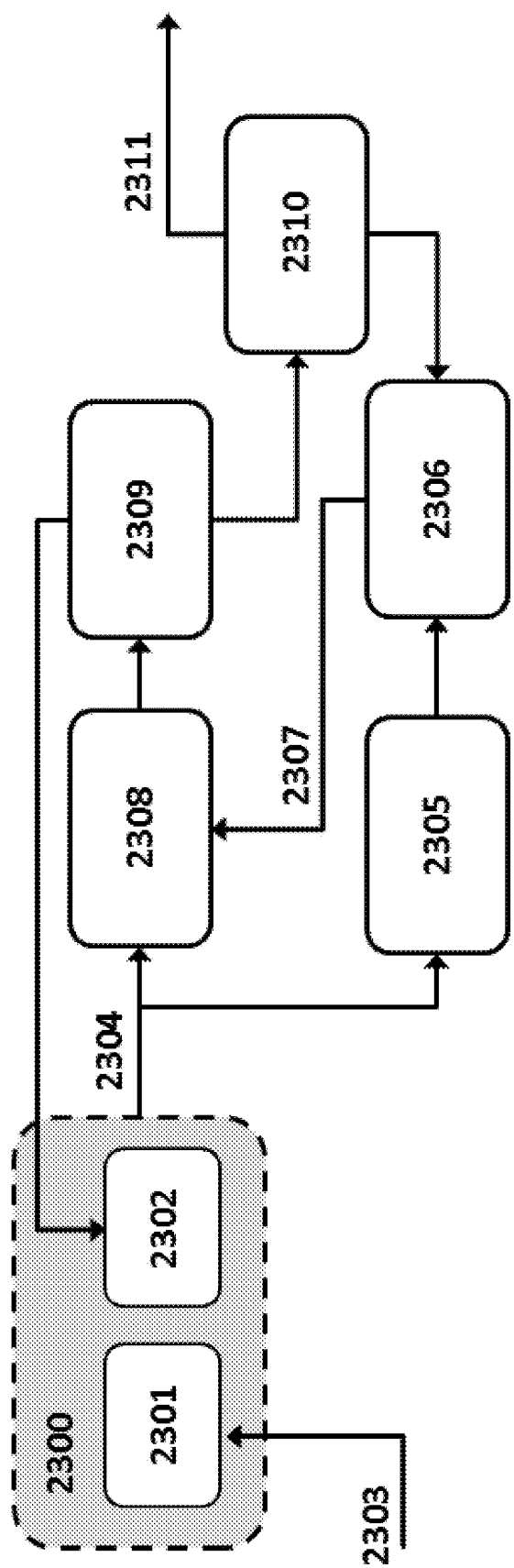
FIG. 23 shows a schematic illustration of an OCM process integrated with a metathesis-based propylene production process.

For example, FIG. 23 shows an exemplary schematic for integration of OCM with metathesis for propylene production. An OCM unit 2300 with an OCM reactor 2301 and a separations section 2302 receives a methane stream 2303 (e.g., natural gas) and produces an ethylene product stream 2304 (e.g., polymer-grade ethylene). A portion of the ethylene stream can be directed into a dimerization reactor 2305 to produce $C_4$ products, which can then be separated in a $C_4$ separation unit 2306. Butene-2 2307 from the $C_4$ separation unit can be directed into a metathesis reactor 2308 along with ethylene from the OCM unit. The metathesis product stream can be directed to a $C_2$ separation unit 2309, with $C_2$ compounds being sent as a recycle stream to the OCM unit separations section. $C_{3+}$ compounds can be directed from the $C_2$ separations unit to a $C_3$ separations unit 2310. Propylene 2311 can be recovered from the $C_3$ separations unit, with $C_{4+}$ compounds directed to the $C_4$ separation unit.

Figure 24:
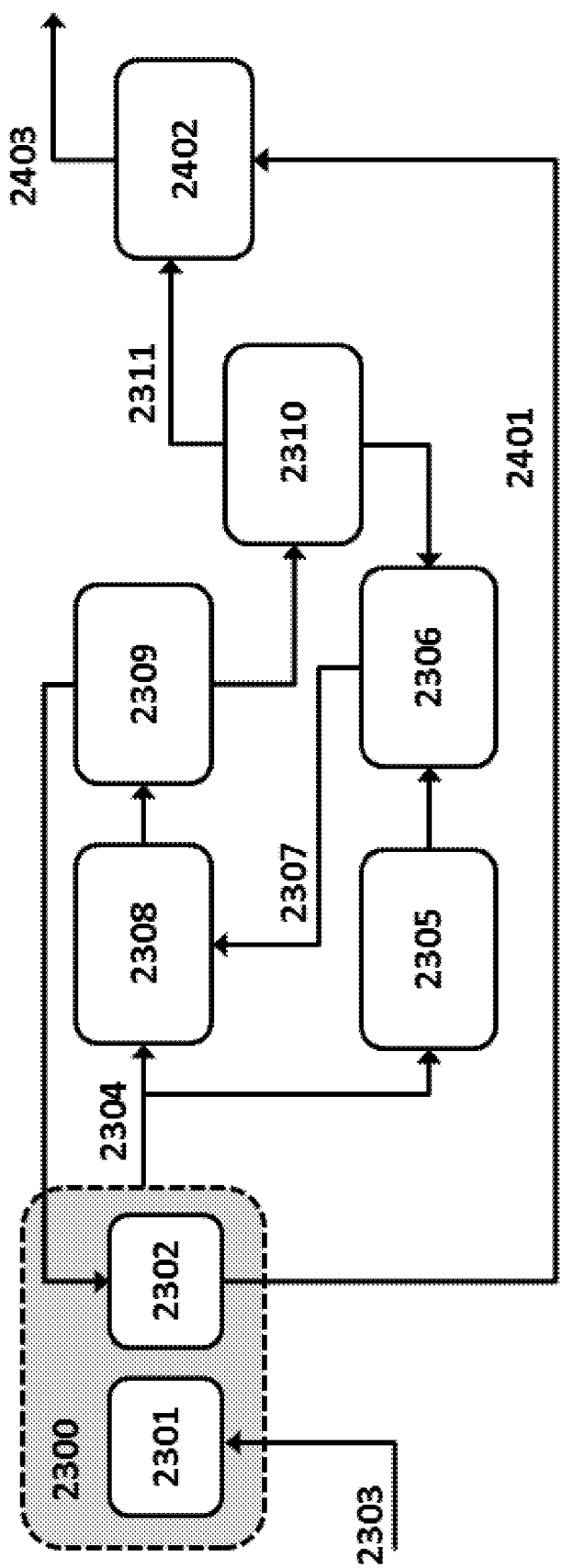
FIG. 24 shows a schematic illustration of an OCM process integrated with a metathesis-based propylene production process with polypropylene production.

Propylene can be further processed into polypropylene. For example, FIG. 24 shows the propylene 2311 being directed, along with ethylene co-monomer 2401 from the OCM unit, into a polypropylene unit 2402 to produce polypropylene 2403.

Metathesis can be conducted as a vapor phase equilibrium reaction. Metathesis can achieve n-butene conversion of about 72% single pass and about 90%-95% overall conversion. The reaction can be conducted at isothermal or nearly isothermal conditions, and can be energy neutral. The presence of iso-butene can lead to more side reactions producing 2,3-dimethylbutene and isoamylene.

In some cases, the recovery systems are integrated. For example, with reference to FIG. 25A, a case is shown having a $C_2$ splitter 2500 that produces enriched ethylene 2501 for the metathesis unit 2502 and/or the dimerization unit 2504. In some cases, the enriched ethylene is polymer-grade ethylene (which can also be used as a co-monomer in the production of polypropylene). In some instances, the $C_2$ splitter 2500 is not operated at conditions that result in polymer-grade ethylene. The enriched ethylene stream can be about 60%, about 70%, about 80%, about 90%, about 95%, or about 99% ethylene by mass. In some cases, the enriched ethylene stream is at least about 60%, at least about 70%, at least about 80%, at least about 90%, at least about 95%, or at least about 99% ethylene by mass.

Figure 25A:
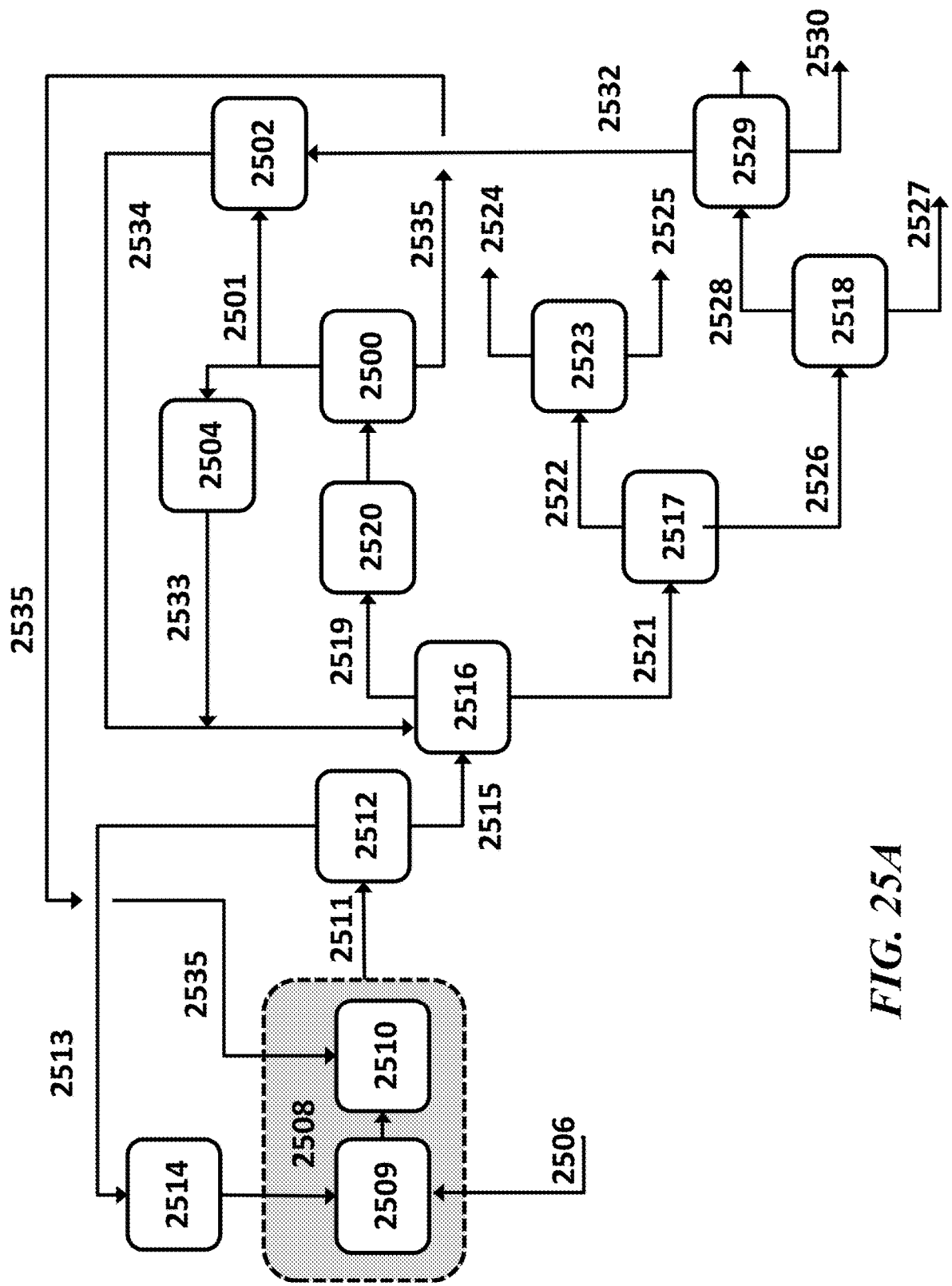
FIG. 25A shows a schematic illustration of an OCM process integrated with a metathesis-based propylene production process having a $C_2$ splitter.

Continuing with FIG. 25A, reactants 2506 (i.e., methane and $O_2$) can be fed into an OCM reactor 2508 having a catalyst bed 2509 and an ethane conversion section 2510. The OCM reactor can produce an OCM effluent 2511 that goes to a de-methanizer 2512. In some cases, there are additional units in the OCM process that are not shown, such as compressors, $CO_2$ removal units, drying units, desulfurization units, quenchers and heat exchangers. The de-methanizer overhead 2513 can contain $C_1$ compounds and go to a methanation unit 2514 for conversion into methane and recycle to the OCM reactor 2508. As used herein, the terms "overhead" and "bottoms" do not limit the portion or section of the separation column from which the stream emerges (e.g., in some cases, the "bottoms" can come out of the middle or top of the separation column).

Figure 25B:
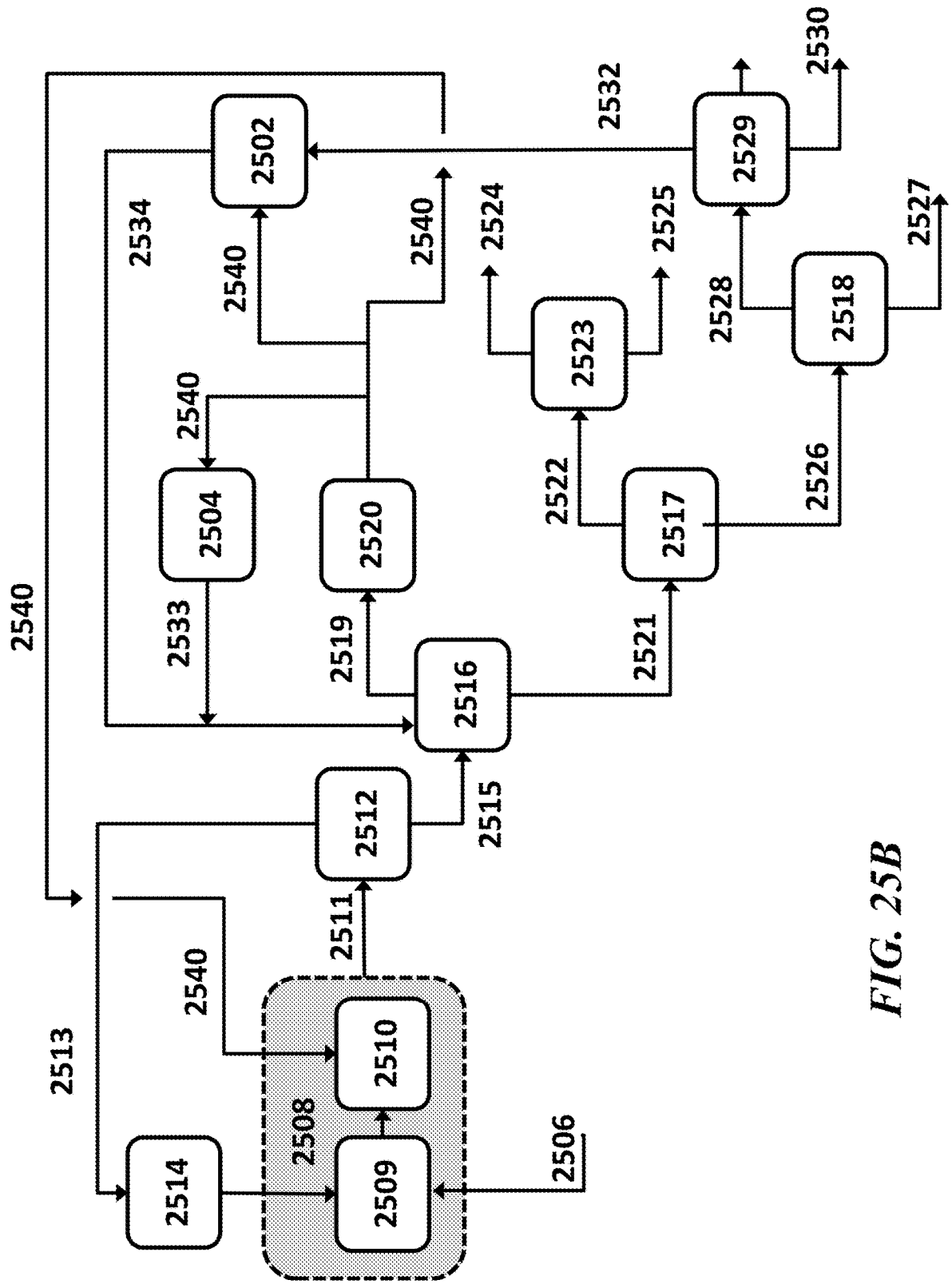
FIG. 25B shows a shows a schematic illustration of an OCM process integrated with a metathesis-based propylene production process without a $C_2$ splitter.

The de-methanizer bottoms 2515 can include $C_{2+}$ compounds and continue into a fractionation train including a de-ethanizer 2516, a de-propanizer 2517 and a de-butanizer 2518. The de-ethanizer overhead 2519 can contain $C_2$ compounds and go to a hydrogenation unit 2520, which hydrogenation unit can (selectively) hydrogenate acetylene. As described herein, the $C_2$ compounds can be separated into an enriched ethylene stream (i.e., using the $C_2$ splitter 2500), or not separated as shown in FIG. 25B.

The de-ethanizer bottoms 2521 can contain $C_{3+}$ compounds and be taken to the de-propanizer 2517. The de-propanizer overhead 2522 can contain $C_3$ compounds that can be split in a $C_3$ splitter 2523 into propane 2524 and propylene 2525. In some cases, the propylene is polymer-grade. In some cases, the propylene is used to make polypropylene (optionally with an ethylene co-monomer, such as derived from the present process, i.e., from the $C_2$ splitter 2500). In some embodiments, the propylene 2525 is about 85%, about 90%, about 95%, about 99%, about 99.5%, about 99.9%, or about 99.95% pure. In some instances, the propylene 2525 is at least about 85%, at least about 90%, at least about 95%, at least about 99%, at least about 99.5%, at least about 99.9%, or at least about 99.95% pure.

The de-propanizer bottoms 2526 can contain $C_{4+}$ compounds and be directed to a de-butanizer 2518. The de-butanizer can produce a bottoms stream 2527 that includes $C_{5+}$ compounds and an overhead stream 2528 comprising $C_4$ compounds, which $C_4$ compounds can be sent to a $C_4$ splitter 2529. The $C_4$ splitter can produce a plurality of streams (i.e., 2530, 2531 and 2532) including a stream enriched in butene-2 2532. In some embodiments, the butene-2 2532 is about 85%, about 90%, about 95%, about 99%, about 99.5%, about 99.9%, or about 99.95% pure. In some instances, the butene-2 2532 is at least about 85%, at least about 90%, at least about 95%, at least about 99%, at least about 99.5%, at least about 99.9%, or at least about 99.95% pure. The butene-2 2532 can go to the metathesis unit 2502.

Additional butene-2 2533 can be produced from the dimerization module 2504 (i.e., from ethylene). The additional butene-2 2533 can be used directly in the metathesis reactor 2502 in some cases. However, as shown here, the additional butene-2 can be recycled to the fractionation train (e.g., to the de-ethanizer 2516) to enrich the concentration of butene-2 prior to metathesis.

The metathesis unit can produce a propylene stream 2534 that can be utilized directly or enriched (e.g., to polymer grade propylene) by recycling the dilute propylene stream 2534 to the fractionation train (e.g., to the de-ethanizer 2516).

The process can produce a number of additional streams that can be utilized directly or recycled in the process, such as an ethane stream 2535 coming from the $C_2$ splitter that can be recycled to the catalyst bed 2509 and/or ethane conversion section 2510 of the OCM reactor 2508.

In some cases, the $C_2$ compounds are not split into enriched ethylene or enriched ethane streams. With reference to FIG. 25B, the de-ethanizer overhead 2519 can be used in the metathesis module 2502, in the dimerization module 2504, and/or can be recycled to the OCM reactor 2508 directly (e.g., without first being separated in a $C_2$ splitter). In some cases, the $C_2$ stream 2519 can go through a hydrogenation unit 2520 (e.g., that hydrogenates acetylene) to produce a hydrogenated $C_2$ stream 2540, which hydrogenated $C_2$ stream 2540 can be used in the metathesis module 2502, in the dimerization module 2504. In some embodiments, the hydrogenated $C_2$ stream 2540 can contain about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, or about 95% compounds other than ethylene. In some cases, the hydrogenated $C_2$ stream 2540 can contain at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, or at least about 95% compounds other than ethylene.

It should be understood from the foregoing that, while particular implementations have been illustrated and described, various modifications can be made thereto and are contemplated herein. It is also not intended that the invention be limited by the specific examples provided within the specification. While the invention has been described with reference to the aforementioned specification, the descriptions and illustrations of the preferable embodiments herein are not meant to be construed in a limiting sense. Furthermore, it shall be understood that all aspects of the invention are not limited to the specific depictions, configurations or relative proportions set forth herein which depend upon a variety of conditions and variables. Various modifications in form and detail of the embodiments of the invention will be apparent to a person skilled in the art. It is therefore contemplated that the invention shall also cover any such modifications, variations and equivalents. It is intended that the following claims define the scope of the invention and that methods and structures within the scope of these claims and their equivalents be covered thereby.

What is claimed is:

1. An oxidative coupling of methane (OCM) method to generate hydrocarbon compounds containing at least two carbon atoms ($C_{2+}$ compounds), the method comprising:
   (a) injecting oxygen ($O_2$), methane ($CH_4$), and ethane ($C_2H_6$) into an adiabatic OCM reactor, wherein the adiabatic OCM reactor comprises an adiabatic OCM reaction section comprising an OCM catalyst bed for facilitating an OCM reaction and an adiabatic post-bed cracking (PBC) section for facilitating conversion of $C_2H_6$ to ethylene ($C_2H_4$) with the aid of heat liberated by the OCM reaction, and wherein the $C_2H_6$ has a concentration of at least 3 mol % at an inlet of the adiabatic OCM reactor and wherein the concentration of $C_2H_6$ at the inlet of the adiabatic OCM reactor is maintained within +/−0.2 mol %;
   (b) with the aid of the OCM catalyst in the adiabatic OCM reaction section, performing an OCM reaction to convert the $CH_4$ into $C_{2+}$ compounds as part of a product stream;
   (c) in the adiabatic PBC section of the adiabatic OCM reactor and with the aid of heat liberated by the OCM reaction, converting $C_2H_6$ in the product stream into $C_2H_4$ as part of an OCM effluent;
   (d) separating the OCM effluent to produce at least an ethane stream and a stream enriched in $C_2H_4$;
   (e) recycling a portion of the ethane stream to an inlet of the adiabatic OCM reaction section; and
   (f) recycling a portion of the ethane stream to the adiabatic PBC section, wherein the method has a carbon efficiency of at least 60%.

2. The method of claim 1, wherein the concentration of $C_2H_6$ at an inlet of the OCM catalyst bed is at least 3.5 mol %.

3. The method of claim 1, wherein at least a portion of the $C_2H_6$ is injected into the adiabatic OCM reactor separately from the $CH_4$.

4. The method of claim 1, further comprising increasing or decreasing an amount of $CH_4$ injected in (a) to maintain the concentration of $C_2H_6$ during the injecting.

5. The method of claim 1, wherein the concentration of $C_2H_6$ at the inlet of the OCM reactor is from 3 mol % to 6 mol %.

6. The method of claim 1, wherein the carbon efficiency is from 60% to 85%.

7. The method of claim 1, wherein at least a portion of the $C_2H_6$ injected into the adiabatic OCM reactor is injected into a sulfur removal unit prior to being injected into the adiabatic OCM reactor.

8. The method of claim 1, wherein the methane injected into the adiabatic OCM reactor is provided by a methanated stream comprising methane produced by a methanation reactor.

9. The method of claim 8, wherein a natural gas stream comprising methane is combined with the OCM effluent prior to separating the OCM effluent.

10. An oxidative coupling of methane (OCM) method to generate hydrocarbon compounds containing at least two carbon atoms ($C_{2+}$ compounds), the method comprising:
   (a) injecting oxygen ($O_2$), methane ($CH_4$), and ethane ($C_2H_6$) into an adiabatic OCM reactor, wherein the adiabatic OCM reactor comprises an OCM reaction section comprising an OCM catalyst bed for facilitating an OCM reaction and an adiabatic post-bed cracking (PBC) section for facilitating conversion of $C_2H_6$ to ethylene with the aid of heat liberated by the OCM reaction, and wherein the $C_2H_6$ has a concentration of at least 3 mol % within the OCM catalyst bed and wherein a concentration of $C_2H_6$ at an inlet of the adiabatic OCM reactor is maintained within +/−0.2 mol %; and
   (b) with the aid of the OCM catalyst bed in the OCM reaction section, performing an OCM reaction to convert $CH_4$ into $C_2$+ compounds as part of a product stream;
   (c) in the adiabatic PBC section of the adiabatic OCM reactor and with the aid of heat liberated by the OCM reaction, converting $C_2H_6$ in the product stream into ethylene ($C_2H_4$) as part of an OCM effluent;

(d) separating the OCM effluent to produce at least an ethane stream and a stream enriched in $C_2H_4$;

(e) recycling a portion of the ethane stream to the OCM reaction section; and (f) recycling a portion of the ethane stream to the adiabatic PBC section, wherein the method has a carbon efficiency of at least 60%.

11. The method of claim 10, wherein at least a portion of the $C_2H_6$ is injected into the adiabatic OCM reactor separately from the $CH_4$.

12. The method of claim 10, further comprising increasing or decreasing an amount of $CH_4$ injected in (a) to maintain the concentration of $C_2H_6$ at the inlet of the adiabatic OCM reactor.

13. The method of claim 10, wherein the concentration of $C_2H_6$ at the inlet of the adiabatic OCM reactor is from 3 mol % to 6 mol %.

14. The method of claim 10, wherein the carbon efficiency is from 60% to 85%.

15. The method of claim 10, wherein at least a portion of the $C_2H_6$ injected into the adiabatic OCM reactor is injected into a sulfur removal unit prior to being injected into the adiabatic OCM reactor.

16. The method of claim 10, wherein at least a portion of the methane injected into the adiabatic OCM reactor is provided by a methanated stream comprising methane produced by a methanation reactor.

17. The method of claim 16, wherein a natural gas stream comprising methane is combined with the OCM effluent prior to separating the OCM effluent.

* * * * *